United States Patent
Austin et al.

(10) Patent No.: US 7,585,463 B2
(45) Date of Patent: Sep. 8, 2009

(54) APPARATUS AND METHOD FOR DISPENSING FLUID, SEMI-SOLID AND SOLID SAMPLES

(75) Inventors: John Austin, Lexington, MA (US); Peter D. Honkanen, Lexington, MA (US)

(73) Assignee: Aushon BioSystems, Inc., Billerica, MA (US)

(*) Notice: Subject to any disclaimer, the term of this patent is extended or adjusted under 35 U.S.C. 154(b) by 677 days.

(21) Appl. No.: 10/972,792

(22) Filed: Oct. 25, 2004

(65) Prior Publication Data

US 2005/0136534 A1    Jun. 23, 2005

Related U.S. Application Data

(60) Provisional application No. 60/514,285, filed on Oct. 24, 2003.

(51) Int. Cl.
*B01L 3/02* (2006.01)
*G01N 1/10* (2006.01)

(52) U.S. Cl. .................. 422/63; 422/100; 422/64; 422/65; 422/66; 422/68.1; 436/180

(58) Field of Classification Search .................. 422/100, 422/63–67, 68.1; 436/180
See application file for complete search history.

(56) References Cited

U.S. PATENT DOCUMENTS

| | | | |
|---|---|---|---|
| 4,426,548 A | 1/1984 | Oritsuki et al. | |
| 4,626,509 A * | 12/1986 | Lyman | 435/283.1 |
| 5,046,539 A * | 9/1991 | MacLeish et al. | 141/234 |
| 5,104,621 A * | 4/1992 | Pfost et al. | 422/67 |
| 5,585,639 A | 12/1996 | Dorsel et al. | |
| 5,592,289 A | 1/1997 | Norris et al. | |
| 5,678,944 A | 10/1997 | Slocum et al. | |
| 5,700,637 A | 12/1997 | Southern | |
| 5,769,554 A | 6/1998 | Slocum | |
| 5,770,151 A | 6/1998 | Roach et al. | |
| 5,807,522 A | 9/1998 | Brown et al. | |

(Continued)

FOREIGN PATENT DOCUMENTS

EP    1132136    9/2001

(Continued)

OTHER PUBLICATIONS

MiraiBio, *Microarray Product Line*, 2002 (6 pgs.).

(Continued)

*Primary Examiner*—Brian R. Gordon
(74) *Attorney, Agent, or Firm*—Goodwin Procter LLP

(57) ABSTRACT

The invention relates generally to the field of automated collection and deposition of fluid, semi-solid, and solid samples of biological or chemical materials. More specifically, the invention relates to the field of microarrayers, which are devices for autonomously depositing minute droplets of biological or chemical fluid samples in ordered arrays onto substrates. The invention also relates to tissue arrayers, which are devices for the collection and deposition of solid and semi-solid tissue samples in ordered arrays. Other aspects of the invention relate to fluidics robots, which are devices for the autonomous collection, dispensing and processing of biological or chemical fluid samples. The invention improves the throughput of microarrayers, tissue arrayers, and fluidics robots by providing methods and apparatuses to precisely and repeatably load supplies into the machines.

68 Claims, 22 Drawing Sheets

U.S. PATENT DOCUMENTS

| | | | |
|---|---|---|---|
| 5,895,915 | A | 4/1999 | DeWeerd et al. |
| 5,897,837 | A * | 4/1999 | Mizuno .................. 422/100 |
| 6,027,890 | A | 2/2000 | Ness et al. |
| 6,043,481 | A | 3/2000 | Tan et al. |
| 6,048,695 | A | 4/2000 | Bradley et al. |
| 6,075,613 | A | 6/2000 | Schermer et al. |
| 6,078,390 | A | 6/2000 | Bengtsson |
| 6,101,946 | A | 8/2000 | Martinsky |
| 6,103,518 | A | 8/2000 | Leighton |
| 6,132,997 | A | 10/2000 | Shannon |
| 6,177,248 | B1 | 1/2001 | Oliner et al. |
| 6,185,561 | B1 | 2/2001 | Balaban et al. |
| 6,190,616 | B1 | 2/2001 | Jovanovich et al. |
| 6,193,102 | B1 | 2/2001 | Bevirt et al. |
| 6,218,803 | B1 | 4/2001 | Montagu et al. |
| 6,228,659 | B1 | 5/2001 | Kowallis et al. |
| 6,235,483 | B1 | 5/2001 | Wolber et al. |
| 6,238,910 | B1 | 5/2001 | Custance et al. |
| 6,240,790 | B1 | 6/2001 | Swedberg et al. |
| 6,245,297 | B1 | 6/2001 | Kowallis |
| 6,255,116 | B1 * | 7/2001 | Leber et al. .................. 436/54 |
| 6,269,846 | B1 | 8/2001 | Overbeck et al. |
| 6,287,778 | B1 | 9/2001 | Huang et al. |
| 6,303,301 | B1 | 10/2001 | Mack |
| 6,308,750 | B1 | 10/2001 | Burke |
| 6,309,822 | B1 | 10/2001 | Fodor et al. |
| 6,333,155 | B1 | 12/2001 | Lockhart et al. |
| 6,340,565 | B1 | 1/2002 | Oliner et al. |
| 6,353,774 | B1 | 3/2002 | Goldenberg et al. |
| 6,355,487 | B2 | 3/2002 | Kowallis |
| 6,361,745 | B1 | 3/2002 | Regan et al. |
| 6,361,947 | B1 | 3/2002 | Dong et al. |
| 6,365,349 | B1 | 4/2002 | Moynihan et al. |
| 6,383,801 | B1 | 5/2002 | Leighton |
| 6,386,219 | B1 | 5/2002 | Barth et al. |
| 6,395,554 | B1 | 5/2002 | Regan et al. |
| 6,399,299 | B1 | 6/2002 | Bobrow et al. |
| 6,399,364 | B1 | 6/2002 | Reeve et al. |
| 6,407,858 | B1 | 6/2002 | Montagu |
| 6,416,719 | B1 * | 7/2002 | Fawcett et al. ............... 422/104 |
| 6,423,536 | B1 | 7/2002 | Jovanovich et al. |
| 6,428,752 | B1 | 8/2002 | Montagu |
| 6,429,016 | B1 | 8/2002 | McNeil |
| 6,432,696 | B2 | 8/2002 | Custance et al. |
| 6,447,723 | B1 | 9/2002 | Schermer et al. |
| 6,448,010 | B1 | 9/2002 | Zhao |
| 6,450,047 | B2 | 9/2002 | Swedberg et al. |
| 6,453,243 | B1 | 9/2002 | Watanabe et al. |
| 6,468,783 | B1 | 10/2002 | Leighton |
| 6,471,916 | B1 | 10/2002 | Noblett |
| 6,472,671 | B1 | 10/2002 | Montagu |
| 6,485,913 | B1 | 11/2002 | Becker et al. |
| 6,489,112 | B1 | 12/2002 | Hadd et al. |
| 6,490,533 | B2 | 12/2002 | Weiner et al. |
| 6,495,106 | B1 * | 12/2002 | Kalra et al. .................. 422/100 |
| 6,495,369 | B1 | 12/2002 | Kercso et al. |
| 6,496,309 | B1 | 12/2002 | Bliton et al. |
| 6,500,921 | B1 | 12/2002 | Fuller et al. |
| 6,510,391 | B2 | 1/2003 | Balaban |
| 6,524,800 | B2 | 2/2003 | Lockhart et al. |
| 6,551,557 | B1 | 4/2003 | Rose et al. |
| 6,558,907 | B2 | 5/2003 | Koroulis et al. |
| 6,579,367 | B2 | 6/2003 | Vann et al. |
| 6,696,271 | B2 | 2/2004 | Slamon et al. |
| 6,722,395 | B2 | 4/2004 | Overbeck et al. |
| 6,755,131 | B2 * | 6/2004 | Dannoux et al. ............ 101/485 |
| 6,759,012 | B2 | 7/2004 | Haslam et al. |
| 6,813,567 | B2 | 11/2004 | Weiner et al. |
| 6,868,875 | B2 * | 3/2005 | De Beukeleer et al. ...... 141/130 |
| 6,874,699 | B2 * | 4/2005 | Larson et al. ............. 239/102.1 |
| 6,878,554 | B1 * | 4/2005 | Schermer et al. ............ 436/180 |
| 6,943,036 | B2 * | 9/2005 | Bass ......................... 436/180 |
| 7,294,309 | B1 * | 11/2007 | Goldberg et al. ............ 422/100 |
| 7,312,068 | B2 * | 12/2007 | Pinkel et al. ............. 435/287.2 |
| 2001/0005489 | A1 * | 6/2001 | Roach et al. .................. 422/99 |
| 2002/0064482 | A1 * | 5/2002 | Tisone et al. ................ 422/100 |
| 2002/0085960 | A1 | 7/2002 | Henninger et al. |
| 2002/0104389 | A1 * | 8/2002 | Hovey .................... 73/864.17 |
| 2002/0142483 | A1 * | 10/2002 | Yao et al. .................... 436/180 |
| 2002/0159919 | A1 * | 10/2002 | Churchill et al. ............. 422/100 |
| 2003/0002962 | A1 | 1/2003 | Atkinson et al. |
| 2003/0003025 | A1 * | 1/2003 | MacAulay et al. .......... 422/100 |
| 2003/0008310 | A1 | 1/2003 | Williams et al. |
| 2004/0022689 | A1 * | 2/2004 | Wulf et al. .................. 422/100 |
| 2005/0054116 | A1 * | 3/2005 | Potyrailo et al. ............ 436/180 |
| 2005/0220675 | A1 * | 10/2005 | Reed et al. .................. 422/100 |
| 2005/0271551 | A1 * | 12/2005 | Shumate et al. ............. 422/100 |
| 2006/0002824 | A1 * | 1/2006 | Chang et al. ................ 422/100 |
| 2006/0057029 | A1 * | 3/2006 | Coassin et al. .............. 422/100 |
| 2006/0057031 | A1 * | 3/2006 | Hantschel et al. ........... 422/100 |

FOREIGN PATENT DOCUMENTS

| | | |
|---|---|---|
| EP | 1203945 | 5/2002 |
| GB | 922868 | 4/1963 |
| JP | 2002 204693 | 7/2002 |
| WO | WO 98/33052 | 7/1998 |
| WO | WO 00/48936 | 8/2000 |
| WO | WO 00/66269 | 11/2000 |
| WO | WO 00/73504 | 12/2000 |
| WO | WO 00/79251 | 12/2000 |
| WO | WO 00/79326 | 12/2000 |
| WO | WO 01/01143 | 1/2001 |
| WO | WO 01/07898 | 2/2001 |
| WO | WO 01/35074 | 5/2001 |
| WO | WO 01/57254 | 8/2001 |
| WO | WO 01/68255 | 9/2001 |
| WO | WO 02/04123 | 1/2002 |
| WO | WO 02/051549 | 7/2002 |
| WO | WO 02/055199 | 7/2002 |
| WO | WO 02/097111 | 12/2002 |

OTHER PUBLICATIONS

MiraiBio, *CRBIO IIe Scanner*, 2002 (2 pgs.).
MiraiBio, *SPBIO II Spotter*, 2002 (2 pgs.).
MiraiBio, *SPBIO II SpotterApplication*, Mar. 16, 2003 (2 pgs.).
HSG-IMIT, *TopSpot Micro-Arrayer Family (Entry Arrayer—TopSpot /E)*, undated (1 pg.).
HSG-IMIT, *TopSpot Micro-Arrayer Family (Modular Arrayer—TopSpot /M)*, undated (1 pg.).
GeneScan Europe AG, *GeneScan (TopSpot M)*, undated (1 pg.).
Prof. Dr. G. Gauglitz, *DNA Microarrays on Plastic Surfaces*, undated (1 pg.).
Genetix Ltd, *Genomics*, May 2002 (8 pgs.).
Genetix Ltd, *aQu High Precision Microarray Pins*, undated (2 pgs.).
Genetix Ltd, *QArray$^{max}$*, undated (1 pg.).
Genetix Ltd, *QArray$^2$*, May 2003 (4 pgs.).
Genetix Ltd, *QArray$^{mini}$*, May 2003 (4 pgs.).
Genetix Ltd, *Microarraying*, undated (4 pgs.).
Genetix Ltd, *QArray Microarraying System*, Jun. 2002 (2 pgs.).
Genetix Ltd, *AQuire Microarraying Scanner*, Jun. 2002 (2 pgs.).
Genetix Ltd, *Rearraying Using Genetix Instruments*, Aug. 2002 (2 pgs.).
Genetix Ltd, *Macroarraying (Gridding) on Genetix Instruments*, undated (2 pgs.).
BioDot, *A/D Series Workstations*, undated (1 pg.).
Joseph DeRisi et al., *The Mguide, A complete guide to building your own Microarrayer*, Version 2.0, available at http://cmgm.stanford.edu/pbrown/mguide, 1998-1999 (21 pgs.).
BioRobotics Ltd., *Compact Entry Level Microarrayer*, 2001 (2 pgs.).
David Latto et al., *Microarray Gene Expression Profiling: The Basics*, BioRobotics Ltd. BioNote MG002 VI.O, 2000 (21 pgs.).
Diane Gershon, *Microrray technology an array of opportunities*, Nature, Apr. 25, 2002 (4 pgs.).

Dan Rose, *Microfluidic Technologies and Instrumentation for Printing DNA Microarrays*, Microarray Printing Technologies, Chapter 2, undated (37 pgs.) (p. 34 missing).
Todd Martinsky, *Printing High Quality Microarrays*, arrayit.com, (53 pgs.).
PerkinElmer Life Sciences, *Piezoarray Flexible Non-Contact Microarraying System*, 2003 (2 pgs.).
PerkinElmer Life Sciences, *BioChip Arrayer Non-Contact Microarraying System*, 2002 (4 pgs.).
PerkinElmer Life Sciences, *SpotArray Enterprise*, 2002 (2 pgs.).
PerkinElmer Life Sciences, *SpotArray Enterprise*, 2002 (6 pgs.).
Amersham Biosciences Corp., *Lucidea Array Spotter*, 2002 (4 pgs.).
Genomic Solutions Inc., *GeneTAC $G^3$ Library Management System*, 2001 (2 pgs.).
Adrienne Burke, *Ramping Up with Robots*, Gomes Technology, undated (2 pgs.).
RoboDesign International Inc., *RoboArrayer with Integrated Vision & Rework Functionality*, undated (4 pgs.).
Cartesian Technologies Inc., *PixSys PA Series, System and Software Operating Manual*, Apr. 1999 (53 pgs.).
Tidhar Dari Shalon, *DNA Micro Arrays: A New Tool for Genetic Analysis*, Dec. 1995 (Ph.D. dissertation) (pp. vi, 52-54, 104-108) (10 pgs.).
*Insight/Outlook*, Genome Research, vol. 7, No. 10, (p. 945), Oct. 1997 (2 pgs.).
Washington School of Medicine, *Array Element Choices*, undated (2 pgs.).
Joseph DeRisi et al., *The Mguide: Part II, A Complete Guide to Building Your Own Microarrayer*, Version 1.0, available at http://cmgm.stanford.edu/pbrown/mguide, 1998 (16 pgs.).
Joseph DeRisi et al., *The Mguide: A Complete Guide to Building Your Own Microarrayer*, Version 1.1, available at http://cmgm.stanford.edu/pbrown/mguide, 1998 (12 pgs.).
Dari Shalon et al., *A DNA Microarray System for Analyzing Complex DNA Samples Using Two-color Fluorescent Probe Hybridization*, Genome Research, (pp. 639-645) 1996 (7 pgs.).
Alexander M. Castellino, *When the Chips are Down*, Genome Research, (pp. 943-946) 1997 (4 pgs.).
Jiri Macas et al., *Adapting the Biomek 2000 Laboratory Automation Work-station for Printing DNA Microarrays*, BioTechniques, vol. 25, No. 1, 1998 (4 pgs.).
Takeda Award 2002 Achievement Facts sheets, *Technical Achievement: The Development and Promotion of DNA Microarrays*, 2002 (13 pgs.).
Renu Heller et al., *Discovery and analysis of inflammatory disease-related genes using cDNA microarrys*, Proc. Natl. Acad. Sci. USA, vol. 94; (pp. 2150-2155) Mar. 1997 (6 pgs.).
Mark Schena et al., *Parallel human genome analysis: microarray-based expression monitoring of 1000 genes*, Proc. Natl. Acad. Sci. USA, vol. 93, (pp. 10614-10619) Oct. 1996 (6 pgs.).
MiraiBio, *SPBIO II*, available at www.miraibio.com, accessed Oct. 28, 2002 (2 pgs.).
MiraiBio, *CRBIO IIE*, available at www.miraibio.com, accessed Oct. 28, 2002 (1 pg.).
Hitachi Genetic Systems, *SPBIO MicroArray System*, http://www.komabiotech.com/product/equipment/microarray.htm, Apr. 23, 2003 (6 pgs.).
Median Systems, *Advance 2000-I*, www.median-systems.co.uk/adv2000.htm, May 4, 2003 (3 pgs.).
Korvis Automation Inc., *cDNA Microarrayer*, http://www.korvis.com/projects/cdna/, Apr. 28, 2003 (2 pgs.).
Korvis Automation Inc., *Customization*, http://www.korvis.com/products/korvis5001_microarrayer/page4.shtml, Apr. 29, 2003 (1 pg.).
ImTek, *Working Group Biochips & Microarrays*, www.imtek.freiburg.de/anwendungen/english/microarrays.htm, Sep. 23, 2003, (2 pgs.).
ImTek, *2.1 About Speed in Microarray Fabrication*, www.imtek.freiburg.de/anwendungen/21.htm, Mar. 19, 2003, (4 pgs.).
GeneScan AG, *TopSpot Production System*, available at http://genescan.prolink.de, Mar. 9, 2003, (2 pgs.).
ImTek, *3.1 Application Overview*, http://www.imtek.de/anwendungen/content/workinggroups/mikroarrays/31.php, , Mar. 12, 2004 (8 pgs.).
Genetix Ltd., *Microarraying and Slide Scanning*, http://www.genescreen.co.uk/microarraying.htm, Jan. 23, 2003 (3 pgs.).
Genetix Ltd., *Qarray*, http://www.genetix.co.uk/productpages/instruments/x2000.htm, Sep. 13, 2002 (3 pgs.).
Genetix Ltd., *aQuire*, http://www.genetix.co.uk/productpages/instruments/x2800.htm, Sep. 13, 2002 (3 pgs.).
Genetix Ltd., *Microarraying Pins*, http://www.genetix.com/productpages/consumables/pins/micropins.htm, Oct. 4, 2002, (3 pgs.).
GeSiM, *The Nano-Plotter NP1.2/System Configurations*, http://www.gesim.de/np-conf.htm, Jul. 11, 2003 (6 pgs.).
Digital Gene Biosciences Co. Ltd., BioSpot Arrayer, http://www.digitalgene.com.tw/english/english/biospotintro.htm, Nov. 14, 2003, (1 pg.).
Digital Gene Biosciences Co. Ltd., BioSpot Arrayer, http://www.digitalgene.com.tw/english/english/biospotspec.htm, Nov. 14, 2003, (1 pg.).
Stanford University, *Part Drawings and Specifications*, http://cmgm.stanford.edu/pbrown/mguide/nospecs2.html, Oct. 5, 2002 (1 pg.).
DeRisi Lab., University of California, *ArrayMaker Version 2*, http://derisilab.ucsf.deu/arraymaker.shtml, Oct. 5, 2002 (2 pgs.).
Scienion, *sciFLEXARRAYER*, http://www.scienion.com/html_files/deutsch/html_produkte/produkte-hardware.html, Jul. 10, 2004, (3 pgs.).
TelChem International, Inc., *Micro Spotting Plus*, http://arrayit.com/Products/Buffers/Printing_Buffers/MSP/msp.html, Feb. 25, 2004 (6 pgs.) (first page missing).
TelChem International, Inc., *Miroplate Microarrayer*, http://arrayit.com/Products/Microarrayl/Microplate_Microarrayer/microplate_microarrayer.html, Feb. 15, 2004 (p. 1 of 11 only).
TelChem International, Inc., *Stealth Micro Spotting Device*, http://arrayit.com/Products/Printing/Stealth/stealth.html, Sep. 13, 2002 (5 pgs.).
TelChem International, Inc., *SpotBot Personal Microarrayer*, http://arrayit.com/Products/Printing/Spotbot/spotbot.html, Sep. 13, 2002 (3 pgs.).
TelChem International, Inc., *Micro Spotting Demo*, http://arrayit.com/Products/Printing/index/index.html, Mar. 9, 2003 (1 pg.).
TelChem International, Inc., *Stealth Micro Spotting Pins and Printheads*, http://www.arrayit.com/Products/Printing/Stealth/stealth.html, May 9, 2003 (8 pgs.).
Yale University School of Medicine, *What are Tissue Microarrays?*, http://www.yalepath.org/dept/research/ycctma/tisarray.htm, Sep. 3, 2004 (8 pgs.).
Chemicon International, *Advanced Tisue Arraryer (ATA100)*, http://www.chemicon.com/Featured/ata100-Arrayer.asp, Jul. 10, 2004 (2 pgs.).
Chemicon International, *Advanced Tisue Arraryer*, http://www.chemicon.com/product/productdatasheet.asp?ProductItem=ATA100, Jul. 10, 2004 (26 pgs.).
BioRobotics, *Microarraying with the MicroGrid II*, http://www.biorobotics.co.uk/Pages/mgrid2.html, Sep. 13, 2002 (4 pgs.).
BioRobotics, *Arraying Products*, http://www.biorobotics.com/Pages/arraying.html, Jan. 20, 2003 (1 pg.).
BioRobotics, *Current News*, http://www.biorobotics.com/Pages/currentn.html, Jan. 20, 2003 (3 pgs.).
BioRobotics, *Microarraing with the MicroGrid II*, http://www.biorobotics.com/Pages/mgrid2.html;#micgrdpro%20anchor, Jan. 20, 2003 (4 pgs.).
Apogent Discoveries, *Arraying Technology*, http://www.apogentdiscoveries.com/AT/MicroGrid.asp, Oct. 28, 2002 (2 pgs.).
BioRobotics, *AGAC Facilities*, http://www.agac.umn.edu/BioRobotic.htm, Mar. 9, 2003 (2 pgs.).
BioRobotics, *Genomic Microarrays: An Overview*, http://www.biorobotics.co.uk/Pages/micover.htm, Sep. 13, 2002 (5 pgs.).
BioRobotics, *Microarraying*, http://www.biorobotics.co.uk/Pages/marray.html, Sep. 13, 2002 (2 pgs.).
Bio-Rad Laboratories, *VersArray Colony Picker and Arrayer Systems*, available at http://www.bio-rad.com, Oct. 18, 2003 (3 pgs.).

Bio-Rad Laboratories, *VersArray ChipWriter Pro Systems*, available at http://www.bio-rad.com, Oct. 18, 2003 (3 pgs.).
Bio-Rad Laboratories, *VersArray ChipWriter Compact System*, available at http://www.bio-rad.com, Oct. 18, 2003 (3 pgs.).
Radius Biosciences Inc., *Radius 3XVP Arrayer*, http://users.erols.com/radius.ma.ultranet/Arrayer-Main.htm, Jan. 22, 2003 (2 pgs.).
Radius Biosciences Inc., *Home page*, http://users.rcn.com/radius.ma.ultranet/, Oct. 31, 2002 (11 pgs.).
PerkinElmer Life Sciences, *SpotArray 72*, http://lifesciences.perkinelmer.com/areas/microarray/spot72.asp, Jan. 22, 2003 (2 pgs.).
PerkinElmer Life Sciences, *SpotArray 72 Microarray Printing System*, http://lifesciences.perkinelmer.com/areas/microarray/spot723.asp, Jan. 22, 2003 (2 pgs.).
PerkinElmer Life Sciences, *BioChip Arrayer*, http://las.perkinelmer.com/catalog/Product.aspx?ProductID=CBC0000, Jul. 14, 2003 (1 pg.).
PerkinElmer Life Sciences, *Protein Microarrays Spotting*, available at http://las.perkinelmer.com, Jul. 14, 2003 (1 pg.).
PerkinElmer Life Sciences, *BioChip Arrayer*, http://lifesciences.perkinelmer.com/areas/microarray/biochip.asp, Jan. 22, 2003 (2 pgs.).
PerkinElmer Life Sciences, *SpotArray Enterprise*, http://lifesciences.perkinelmer.com/areas/microarray/spotenter.asp, Jan. 22, 2003 (1 pg.).
PerkinElmer Life Sciences, *SpotArray 24*, http://lifesciences.perkinelmer.com/areas/microarray/spot24.asp, Jan. 10, 2003 (2 pgs.).
Trueforce, *Industry Profile: Engineering Services Inc.—SDDC*, http://trueforce.com/Lab_Automation/Lab_Automation_Companies/; Mar. 13, 2003 (2 pgs.).
Oswel, *Making Chips or Microarrays*, http://www.oswel.com/code/en/proc_maki.htm, Apr. 28, 2003 (3 pgs.).
Oswel, *Systems-Micro Array-EuroGridder SDDC-3*, http://www.oswel.com/code/en/micr_tech_euro2.htm, Apr. 28, 2003 (1 pg.).
Oswel, *Systems-Micro Array-EuroGridder CDDC-2*, http://www.oswel.com/code/en/micr_tech_euro3.htm, Apr. 28, 2003 (3 pgs.).
Oswel, *Systems-Micro Array Accessories*, http://www.oswel.com/code/en/micr_tech_acce.htm, Apr. 28, 2003 (4 pgs.).
Bio-Rad Laboratories, *Microarray Products*, available at http://www.bio-rad.com, Sep. 13, 2002 (1 pg.).
Bio-Rad Laboratories, *VersArray ChipWriter Pro Systems*, available at http://www.bio-rad.com/, Sep. 13, 2002 (3 pgs.).
Bio-Rad Laboratories, *VersArray ChipReader Systems*, available at http://www.bio-rad.com, Sep. 13, 2002 (3 pgs.).
Bio-Rad Laboratories, *VersArray ChipWriter Compact System*, available at http://www.bio-rad.com, Oct. 5, 2002 (2 pgs.).
Engineering Services Inc., *SDDC-2 Microarrayer*, http://www.esit.com/biotech/sddc2.html, Jan. 22, 2003 (3 pgs.).
Universite de Geneve, *Arrayer Geneva Microarray Core*, http://www.microarrays.unige.ch/Equipment/arrayer.html, Jan. 22, 2003 (1 pg.).
Brooks Automation, Inc., *Microarrayer HT*, http://www.brooks.com/pages/723_microarrayer_ht.cfm, Apr. 28, 2003 (2 pgs.).
Intelligent Bio Instruments, *Microarrayer HT*, http://www.intelgenbio.com/MicroArrayer.htm, Oct. 4, 2002 (1 pg.).
Amersham Biosciences, *Lucidea Array Spotter*, available at http://www4.amershambiosciences.com, Mar. 18, 2003 (2 pgs.).
Amersham Biosciences, *Lucidea Spotting Pens*, available at http://www4.amershambiosciense.com, Mar. 18, 2003 (2 pgs.).
GeneMachines, *OmniGrid 300*, http://www.genemachines.org/omnigrid/omngrid300.html, Jan. 10, 2003 (3 pgs.).
GeneMachines, *OmniGrid 100*, http://www.genemachines.com/omnigrid/omnigrdsa.html, Sep. 13, 2002 (4 pgs.).
GeneMachines, *OmniGrid 100*, http://www.genemachines.com/omnigrid/omnigrid.html, Oct. 31, 2002 (3 pgs.).
SuperArray Bioscience Corporation, *GEArray Technologies*, http://www.superarray.com/product_technology.php, Jan. 21, 2003 (2 pgs.).
Cortesian Technologies, Inc., *synQUAD Technology*, http://www.cartesiantech.com/sq_tech.html, Oct. 4, 2002 (3 pgs.).
GeneMachines, *GeneMachines Expands Features on the OmniGrid Microarrayer*, http://www.genemachines.com/pressreleases/12sept2000OG.html, May 4, 2003 (3 pgs.).
GeneMachines, *GeneMachines Releases New Option for OmniGrid Microarrayer*, http://www.genemachines.com/pressreleases/4may1999.html, Jul. 11, 2003 (1 pg.).
GeneMachines, *GeneMachines Microarraying News*, http://www.genemachines.com/omnigrid/index.html, Sep. 13, 2002 (2 pgs.).
GeneMachines, *OmniGrid Accent*, http://www.genemachines.org/omnigrid/accent.html, Jan. 25, 2003 (2 pgs.).
RoboDesign International, Inc., *RoboArrayer*, http://www.robodesign.com/roboarrayer.shtml, Oct. 31, 2002 (1 pg.).
RoboDesign International, Inc., *Matched Pin Sets*, http://www.robodesign.com/matched_pin_sets.shtml, Oct. 31, 2002 (1 pg.).
RoboDesign International, Inc,, *RoboArrayer*, http://www.robodesign.com/roboarrayer.shtml, Jan. 22, 2003 (1 pg.).
RoboDesign International, Inc., *RoboArrayer*, http://www.robodesign.com/roboarrayer.htm, Sep. 13, 2002 (3 pgs.).
The Sanger Institute, *The Microarray Robot*, available at http://www.sanger.ac.uk/Teams/Team52, Apr. 28, 2003 (1 pg.).
The Sanger Institute, *Modualar Robotic Platform*, http://www.sanger.ac.uk/Teams/Team52/currentprojects/index.shtml, Apr. 28, 2003 (1 pg.).
The Sanger Institute, *Gridding*, http://www.sanger.ac.uk/Teams/Team52/currentprojects/gridders.shtml, Apr. 28, 2003 (1 pg.).
The Sanger Institute, *Automatic Pipetting*, http://www.sanger.ac.uk/Teams/Team52/currentprojects/pipetting.shtml, Apr. 28, 2003 (1 pg.).
The Sanger Institute, *8 Way Head*, http://www.sanger.ac.uk/Teams/Team52/currentprojects/others.shtml, Apr. 28, 2003 (2 pgs.).
Cartesian Technologies, Inc., *PinArray Technology*, http://www.cartesiantech.com/pa_tech.html, Oct. 4, 2002 (2 pgs.).
ARK-Genomics, *Microarrys*, http://www.ark-genomics.org/services/microarrays.html, May 13, 2003 (1 pg.).
BioRobotics, *Microarraying with the MicroGrid*, http://www.biorobotics.com/Pages/mgrid/html, Mar. 9, 2003 (2 pgs.).
Stanford University, *The Mguide, Version 2.0*, http://cmgm.stanford.edu/pbrown/mguide/, Feb. 15, 2004 (3 pgs.).
Deborah A. Fitzgerald, *The Scientist*, Jul. 8, 2002, available at http://www.the-scientist.com/yr2002/jul/profile_020708.html, Jan. 22, 2003 (7 pgs.).
David D.L. Boutell, *Options Available-from start to finish-for obtaining expression data by microarray, Nature Genetics*, 1999, available at http://www.nature.com/ng/journal/v21/nls/fig_tab/ng0199supp_25_T4.html, Feb. 13, 2004 (1 pg.).
Daedal Division, *Positioning and Motion Control for the Life Sciences*, http://www.phdaedal.com/1s/html/micro_arrayers.html, Nov. 14, 2003 (2 pgs.).
BioRobotics, *Microarraying*, http://www.szbk.hu/-chiplab.robot.htm., Oct. 13, 2003 (1 pg.).
VertMarkets, Inc., *Robotic Micro-Arrayer System*, available at http://www.bioreseachonline.com/Content/ProductShowcase Jul. 11, 2003 (2 pgs.).
Oklahoma State University, *Microarray Core Facility*, available at http://opbs.okstate.edu/CORE/Arrayer/arrayer.html, Jul. 10, 2003 (1 pg.).
VertMarkets, Inc., *Robotic Microarrayer*, http://www.bioreseachonline.com/Content/ProductShowcase/ Jul. 11, 2003 (2 pgs.).
Ronald J. Sapolsky et al., *The Functional Analysis of Genomes: Recent Research in the Laboratory of Dr. Ronald Davis*, available at http://www.abrf.org/ABRFNews/1997/December1997/dec97davis.html, Apr. 9, 2004 (7 pgs.).
D. Shalon et al., *A DNA Microarray system for analyzing complex DNA samples using two-color fluorescent probe hybridization*, (abstract only), available at http://www.genome.org/cgi/content/abstract/6/7/639?maxtoshow=&HITS=10&hits=1-&R, Apr. 15, 2004 (16 pgs.).
University of Arizona, *Production of DNA Microarrays*, http://latin.arizona.edu~dgalbrai/arrayer.html, Apr. 15, 2004 (2 pgs.).
BioAutomation, *Micro Arrayer*, http://www.bioautomation.com/magna.html, Jan. 22, 2003 (2 pgs.).

Beckman Coulter Inc., *New A2 Protein Microarray System for Multiplexed Biochemical Analysis Delivers Thousands of Results in a Single Plate*, available at http://www.beckmancoulter.com/hr/pressroom/oc.pressroom.asp, May 11, 2003 (2 pgs.).

Beckman Coulter Inc., *New A2 Microarray Fluorescence Reader for High-Throughput Protein Evaluation*, available at http://www.beckmancoulter.com/hr/pressroom/oc.pressroom.asp, May 11, 2003 (2 pgs.).

Beckman Coulter Inc., *Immunassay-based Microarrays*, available at http://www.beckmancoulter.com/products/pr1.asp, May 11, 2003 (2 pgs.).

Beckman Coulter Inc., *A2 Microarray System*, available at www.beckmancoulter.com/product/pr1.asp, May 11, 2003 (3 pgs.).

BiOptro Co., Ltd., Economy Version Microarrayer, www.bioptro.com/htdocs/page79.htm., Apr. 28, 2003 (3 pgs.), Mar. 26, 2008.

International Search Report and Written Opinion for International Application No. PCT/US04/035101, mailed from the International Searching Authority on Jul. 21, 2005 (16 pgs.).

Partial International Search Report for International Application No. PCT/US04/035101, mailed from the International Searching Authority on Feb. 18, 2005. (6 pgs.).

About Kinematic Couplings, webpage: http://pergatory.mit.edu/kinematiccouplings/html/about.html, accessed Sep. 5, 2008, 15 pages.

Kinematic Couplings for Rapid and Repeatable Positioning, webpage: http://pergatory.mit.edu/perg/research/archive/Culpepper/kincouple.htm, accessed Sep. 19, 2008, 2 pages.

* cited by examiner

APPARATUS AND METHOD FOR DISPENSING FLUID, SEMI-SOLID AND SOLID SAMPLES

CROSS REFERENCE TO RELATED APPLICATIONS

This application incorporates by reference in its entirety and claims priority to U.S. Provisional Patent Application Ser. No. 60/514,285, entitled "Microarrayer," filed on Oct. 24, 2003.

FIELD OF THE INVENTION

The present invention relates generally to the field of automated collection and deposition of fluid, semi-solid, and solid samples of biological or chemical materials, for example, using a microarrayer.

BACKGROUND

The ability to produce arrays of fluid or tissue samples is of great value for increasing the rate at which chemical or biological studies may be performed, and the use of such arrays has been widely adopted in the genomics research, biological research and drug-discovery industries.

Microarrayers are automated instruments used to deposit or spot minute amounts of chemical or biological substances, such as DNA, RNA, cDNA, polynucleotides, oligonucleotides, and proteins in a dense array of minute fluid droplets on a substrate, such as a glass slide. The general purpose of fabricating microarrays is to permit massively parallel investigation of chemical or biological activity. The microarray format allows hundreds, thousands, tens of thousands or hundreds of thousands of assays to be performed in parallel, enabling experiments and investigations that would have previously taken years, to be performed in a matter of days.

Therefore, the ability to produce spotted microarrays in large quantity, rapidly, at reasonable cost, and with uniform and consistent deposition properties, such as spot size, shape and density, has significant industrial and economic importance.

SUMMARY

Several microarray spotting techniques have been developed in recent years to automatically deposit droplets of chemical and biological substances, in a liquid state, onto solid substrates. As used in this disclosure, the term "drop" or "droplet" refers to a very small quantity of fluid, and not to any particular shape of the fluid volume. The deposit elements used to spot a fluid on a substrate includes ink-jets, pens, quill pins, and solid pins. In each spotting technique, a deposition element acquires fluid from a fluid reservoir and spots the droplets in the desired position on the substrate.

The simplest, and perhaps most robust printing method uses solid pins. Significant advantages of solid pins are their simplicity and reliability, ease of cleaning and their relative lack of sensitivity to the sample fluid viscosity. An additional benefit of the use of solid pins is minimal sample fluid wastage. Since only a single droplet is captured by the pin, little or no sample fluid is lost at the cessation of printing with that sample. Disadvantages of spotting with solid pins include variations in spot size and intensity resulting from differences in the evaporation of the fluids being carried by the pins. We have determined that these variations result from the different times of exposure to the air of the fluid droplets for different deposition paths. The exposure time differences are significant considering the fluid volumes carried by such solid deposition pins are in the picoliter to nanoliter range. Therefore, a need exists to eliminate these variations, for example, by providing equal exposure time to fluid droplets held by the deposit element as the deposit element travels from the well plate to the substrate. Another disadvantage of existing solid-pin microarrayers is their lower spot deposition rates compared to quill pins, pens and ink-jets because of the requirement for the solid deposition pin to reacquire fluid from a fluid reservoir after every deposition. A need exists, therefore, for increasing the deposition rate of solid-pin microarrayers.

Existing microarrayers have used several motion architectures (the term "architecture" being used herein to describe the general design of the assembly and its fluid capture and fluid-droplet deposition operations).

Current microarrayer architectures are often inefficient, lack flexibility, have limited throughput, and/or produce microarrays that have a lack of uniformity in the deposition of the fluid droplets. For example, we have determined that variability in the thickness of the substrates which are loaded into the system creates uncertainty in the height of the surface upon which the fluid droplets are deposited and causes undesirable variations in droplet deposition from substrate to substrate. The uncertainty in the height of the fluid deposition surface is of particular concern for non-contact printing with quill pins, solid pins, and pens, since it is desired to accurately touch only the droplets of fluid on the tip of the device upon the substrate, and not the tip itself, to prevent potential damage to delicate substrate surfaces. Traditional microarrayers do not include means for compensating for the lack of uniformity in substrate thicknesses.

Another disadvantage of current microarrayers is that the substrates and well plates need to be manually positioned inside the microarrayer. In addition to being time consuming, which decreases throughput, this process leads to errors resulting from frequent human access to the deposition area. Moreover, traditional microarrayers do not include means for loading the substrates and the well plates into the system in an accurate, repeatable manner. We have determined that his hinders the accurate deposition of fluid samples on the substrates.

Therefore, a need exists to improve the apparatuses and procedures used for loading substrates into, and unloading substrates from, a microarrayer. A need also exists to provide a microarrayer that can accommodate substrates having variable thicknesses while minimizing undesirable variations in droplet deposition from substrate to substrate.

In another aspect, the invention also relates to the more general field of dispensing samples in array formats. Tissue arrays, which are arrays of thin slices of tissue cores, are typically formed in a multi-step process. Typically a piece of biological tissue is formalin-fixed and embedded in a paraffin block, known as the donor block. Small cores of the semi-solid paraffin-embedded tissue (typically about 0.5 millimeters to a few millimeters in diameter) are then removed from the donor block with a tubular cutting device and deposited in an ordered array within matching, vertically-oriented cylindrical recesses in a receiving paraffin block. The receiving paraffin blocks are then thinly sliced in the horizontal plane and the slices are transferred to supporting substrates. The slices of the receiving paraffin block forming the arrays are typically less than 10 microns thick. The receiving paraffin block can therefore produce many copies of the array of core samples, which is of great value and importance for parallel biological experimentation. Tens, hundreds, or thousands of tissue samples can be placed on a tissue array. The solid cores from frozen tissue can be deposited in a similar manner to that described for formalin-fixed semi-solid tissue arrays.

Currently, tissue arrays are most typically produced by manual means, aided in some instances by un-powered, passive, mechanical stages to align the elements of the array deposited into the receiving paraffin block. Many hours and much manual labor are required to produce a tissue array of a few hundred elements. The present limitations in flexibility, speed, and accuracy are significant impediments to the adoption of this important technology.

A further limitation of current tissue arrayers is that paraffin-block mounting arrangements have been bottom-referenced, i.e. the block is mounted such that its bottom surface rests upon a reference plane; however, core-formation and core deposition occurs at the top surface. Paraffin blocks are not typically cast to precise dimensional tolerances. Since they are bottom referenced in current systems, uncertainty and variability exists in the location of the top surface of the block where tissue cores are deposited. We have determined that this can lead to inconsistent and inaccurate removal of tissue cores from donor blocks and inconsistent and inaccurate core-placement in receiver blocks.

Therefore, a need exists to improve the apparatuses and procedures used for loading and unloading donor blocks and receiver blocks into and out of a tissue arrayer. A need also exists to provide a tissue arrayer that can accommodate donor blocks and receiver blocks that vary in height to achieve more consistent and accurate removal of tissue cores from donor blocks and more consistent and accurate core-placement in receiver blocks. A need also exists to improve the speed of creating tissue arrays using an automated process.

A further dispensing application covered by the present invention relates to the field of fluidics handling systems, the devices that perform these tasks commonly known as fluidics robots. Generally, fluidics handling systems are used to transfer fluids between a fluid source reservoir and a fluid target reservoir. In addition, assays can be automatically prepared and processed, including, in some instances, operations such as mixing, filtering, heating and cooling. In some prior-art applications, centrifugation and polymerase chain reaction steps are also provided. Fluidics handling systems play a significant role within the life science industry for automating fluid dispensing, fluid transfers, assay preparation, and assay processing.

One disadvantage of prior art fluidic robots is that reconfiguration of existing machines to accommodate different numbers, sizes, or styles of reservoirs or other elements requires manual re-configuration of the mounting provisions on a fixed platen. This results in limited flexibility of existing designs and significant time lost to the manual re-configuration. Therefore, a need exists to improve the apparatuses and methods for reconfiguring a fluidic robot to handle different numbers, sizes, or styles of source reservoirs and target reservoirs.

In one aspect the invention relates to a method of depositing at least two minute droplets of fluid on a substrate. The method includes the steps of supplying a first fluid to a deposit element by dipping the deposit element into the first fluid in a fluid reservoir, moving at least one of the deposit element and the substrate relatively to deposit a droplet of the first fluid at a first location on the substrate, supplying a second fluid to the deposit element by dipping the deposit element into the second fluid in the fluid reservoir and moving at least one of the deposit element and the substrate relatively to deposit a droplet of the second fluid at a second location on the substrate. A volume of the first fluid carried by the deposit element and a volume of the second fluid carried by the deposit element are exposed to a surrounding atmosphere for substantially a same amount of time between their respective extractions from the fluid reservoir and their respective depositions on the substrate by controlling at least one of speed and timing of relative motion between the deposit element and the substrate. In one embodiment, the first fluid and the second fluid are obtained from a substantially same location in the fluid reservoir.

In another aspect, the invention relates to a method of repeatedly depositing minute droplets of fluid on a substrate. The method includes capturing fluid on a deposit element and moving at least one of the deposit element and a substrate relatively to deposit the fluid on the substrate such that each deposition occurs at a same determinable time after capturing the fluid on the deposit element. The time is determinable by at least one of adjusting relative-motion velocity of the deposit element and the substrate and introducing a motion delay to one of the deposit element and the substrate.

In another aspect, the invention relates to a tissue arrayer. The tissue arrayer includes a coring head for extracting a core sample from a donor block and depositing the core sample in a receiving block. The tissue arrayer also includes a removable block-holder for holding at least one of the donor block and the receiving block, the removable block-holder including an apparatus for precisely and repeatably positioning the removable block-holder on a block-holder support.

In one embodiment, the block-holder support includes a first datum for engaging the removable block-holder and for restricting movement of the removable block-holder along an x-axis and a mutually orthogonal y-axis, and defining a first point in a z-axis, the z-axis mutually orthogonal to the x-axis and the y-axis, a second datum for engaging the removable block-holder and for at least partially locating the removable block-holder along at least one of the x-axis and the y-axis and defining a second point in the z-axis, and a third datum for engaging the removable block-holder and defining a third point in the z-axis. In one embodiment, the first datum includes at least a portion of a sphere for engaging a conical recess formed in the removable block-holder. In another embodiment, the second datum is engageable with a linear recess formed in the removable block-holder.

In another embodiment in accordance with the invention, the apparatus for precisely and repeatably positioning the removable block-holder on the block-holder support includes a first element for mating with a first datum, and for restricting movement of the removable block-holder along an x-axis and a mutually orthogonal y-axis and defining a first point in a z-axis, the z-axis mutually orthogonal to the x-axis and the y-axis. The apparatus also includes a second element for mating with a second datum, and for at least partially locating the removable block-holder along at least one of the x-axis and the y-axis while defining a second point in the z-axis and a third element for mating with a third datum and defining a third point in the z-axis. The first element may include a conical recess for mating with the first datum. In another embodiment, at least two of the elements are adjustable along the z-axis.

In another embodiment, the removable block-holder includes a top surface and a bottom surface spaced from the top surface, an aperture extending at least partially between the top surface and the bottom surface, an intersection of the aperture and the top surface defining a perimeter, and at least three reference points proximate the perimeter and defining a reference plane, the reference points for engaging a top surface of at least one of the donor block and the receiving block when at least one of the donor block and the receiving block is disposed in the aperture. In one embodiment, the removable block-holder includes reference surfaces for engaging and precisely locating a top surface of at least one of the donor block and the receiving block in a known plane with respect to the removable block-holder. In another embodiment, the removable block-holder further includes a removable block-mounting fixture onto which at least one of the donor block and the receiving block is mountable. The removable block-mounting fixture includes a locking element for securing the removable block-mounting fixture in the removable block-holder and for biasing the top surface of at least one of the donor block and the receiving block against the at least three reference points.

The tissue arrayer can also include a storage for storing at least one removable block-holder and means for transferring at least one removable block-holder between the storage and the block-holder support. In another embodiment, the removable block-holder support includes a donor block-holder support and a receiver block-holder support and the donor block-holder support and the receiver-block holder support are each constrained to move within a plane substantially perpendicular to the coring head when disposed beneath the coring head. In another embodiment, the plane of motion of the donor block-holder is displaced from a plane of motion of the receiver-block holder. In a further adaptation, the tissue arrayer includes a core filling head for depositing material into a void created in the donor block by the coring head.

In another embodiment, at least one of the donor block, the receiver block, the donor block-holder support and the receiver block-holder support, include a tracking device. The tracking device includes at least one of a barcode, a radio-frequency identification (RFID) transponder programmed with a unique code readable by an RFID interrogator by non-contact means, and a semi-conductor memory device programmed with a unique code. The semi-conductor memory device is readable by at least one of an electric sensor, and an external sensor that is in communication with the semi-conductor memory device through at least one of optical, infra-red, and radio-frequency communication. In yet another embodiment, the tissue arrayer includes means for locally storing and updating information on at least one of the donor block, the receiver block, the donor block-holder support and the receiver block-holder support. The means includes at least one of a radio-frequency identification (RFID) transponder that is dynamically programmable onto at least one of the donor block, the receiver block, the donor block-holder support and the receiver block-holder support, the transponder readable by an RFID interrogator by non-contact means, and a semi-conductor memory device. The semi-conductor memory device is dynamically programmable onto at least one of the donor block, the receiver block, the donor block-holder support and the receiver block-holder support. The semi-conductor memory device is also readable by at least one of electrical contact and an external sensor that is in communication with the semi-conductor memory device through at least one of optical, infra-red, and radio-frequency communication.

In another embodiment, overall removable block-holder and block-holder support system position accuracy is within ±0.02" in x, y, and z-axes. In a preferred embodiment, overall removable block-holder and block-holder support system position accuracy is within ±0.002" in a z-axis and within ±0.01" in x and y axes. In a more preferred embodiment, overall removable block-holder and block-holder support system position accuracy is within ±0.0002" in a z-axis and within ±0.001" in x and y axes.

In another aspect, the invention relates to a method of extracting tissue core samples from a donor block and depositing the core samples in a receiver block. The method includes the steps of providing a donor block including a tissue sample to be cored and providing a coring head for extracting a tissue core from the donor block. The method also includes obtaining an image of a surface of the donor block to be cored by the coring head and selecting and recording positional information of a coring location from the obtained image. The method also includes initiating autonomous tissue core sampling at the coring location using the selected and recorded positional information.

In another aspect the invention relates to a receiver block containing the extracted core tissue samples in accordance with the method just described.

In one embodiment, the method includes the step of providing a receiving block and depositing the extracted tissue core into the receiving block. The method can also include the step of filling a void created in the donor block created by the tissue core sampling with a filling material. The step of obtaining an image of the surface of the donor block can further include providing a high resolution camera at a known position from the coring head and providing a high resolution video display to display the image of the donor block. As a further step, the method may include providing at least one positional reference in a field of view of the camera for establishing an offset distance of the camera to the coring head and to correct non-linearities in the displayed image of the donor block.

In another embodiment, the method includes the step of mounting at least one of the donor block and the receiving block on a removable holder, the removable holder including an apparatus for precisely and repeatably positioning the removable holder on a block-holder support.

In another aspect, the invention relates to a fluidics handling system for transferring a fluid from a fluid-source reservoir to a fluid-target reservoir. The fluidics handling system includes at least one dispensing head and a removable holder for holding at least one of a removable fluid-source reservoir and a removable fluid target reservoir, the removable holder including an apparatus for precisely and repeatably positioning the removable holder on a holder-support.

In one embodiment, the holder-support includes a first datum for engaging the removable holder and for restricting movement of the removable holder along an x-axis and a mutually orthogonal y-axis, and defining a first point in a z-axis, the z-axis mutually orthogonal to the x-axis and the y-axis. The holder-support also includes a second datum for engaging the removable holder and for at least partially locating the removable holder along at least one of the x-axis and the y-axis and defining a second point in the z-axis. A third datum is also included in the holder-support for engaging the removable holder and defining a third point in the z-axis. In one embodiment, the first datum includes at least a portion of a sphere for engaging a conical recess formed in the removable holder. In another embodiment, the second datum is engageable with a linear recess formed in the removable holder.

In another embodiment, the apparatus for repeatably positioning the removable holder on the holder-support further includes a first element for mating with a first datum, and for restricting movement of the removable holder along an x-axis and a mutually orthogonal y-axis and defining a first point in a z-axis, the z-axis mutually orthogonal to the x-axis and the y-axis. The apparatus also includes a second element for mating with a second datum, and for at least partially locating the removable holder along at least one of the x-axis and the y-axis while defining a second point in the z-axis. A third element is also included in the apparatus for mating with a third datum and defining a third point in the z-axis. The first element may include a conical recess for mating with the first datum. In one embodiment, at least two of the three elements are adjustable along the z-axis.

The fluidics handling system may also include a storage for storing removable holders. In addition, means for transferring the removable holder between the storage and the holder support may be included. In one embodiment, the removable holder is moved from the storage to the holder-support by moving the removable holder in a vertical direction within the holder storage to dispose the removable holder onto the holder-support and moving the holder support in a horizontal direction to retract the holder support from the storage.

In another embodiment, the dispensing head includes a plurality of dispensing elements, the dispensing elements moveable along at least one of an x-axis and a mutually orthogonal y-axis relative to each other to alter the distance between tips of the dispensing elements. In yet another embodiment, the dispensing head is constrained to move along a single axis. The removable holder may be constrained to move within a plane perpendicular to the single axis.

In another embodiment, the removable holder includes a removable source-holder for holding the fluid-source reservoir, and a removable target-holder for holding the fluid-target reservoir. The removable fluid source-holder and the removable target-holder are independently movable in any direction within separate planes separated by a distance along the single axis.

The fluidics handling system can also include at least one removable pipette-tip holder for holding pipette tips. The pipette-tip holder can include an apparatus for precisely and repeatably positioning the pipette-tip holder on a pipette-tip holder support, the pipette-tip holder movable in a plane that is perpendicular to the single axis and displaced from the planes of motion of the removable fluid source-holder and the removable target-holder.

In another embodiment, at least one of the fluid-source reservoir, the fluid-target reservoir, and the removable holder include a tracking device. The tracking device includes at least one of a barcode, a radio-frequency identification (RFID) transponder programmed with a unique code readable by an RFID interrogator by non-contact means, and a semi-conductor memory device programmed with a unique code. The unique code is readable by at least one of an electric sensor and an external sensor that is in communication with the semi-conductor memory device through at least one of optical, infra-red, and radio-frequency communication. In a further embodiment, the fluidics handling system includes a means for locally storing and updating information on at least one of the fluid-source reservoir, the fluid-target reservoir, and the removable holder. The means includes at least one of a barcode; a radio-frequency identification (RFID) transponder that is dynamically programmable onto the at least one of the fluid-source reservoir, the fluid-target reservoir, and the removable holder, the transponder readable by an RFID interrogator by non-contact means; and a semi-conductor memory device that is dynamically programmable onto the at least one of the fluid-source reservoir, the fluid-target reservoir, and the removable holder, the semi-conductor memory device readable by at least one of electrical contact and an external sensor that is in communication with the semi-conductor memory device through at least one of optical, infra-red, and radio-frequency communication.

In one embodiment, overall removable holder and holder-support system position accuracy is within ±0.02" in x, y, and z-axes. In a preferred embodiment, overall removable holder and holder-support system position accuracy is within ±0.002" in a z-axis and within ±0.01" in x and y axes. In a more preferred embodiment, overall removable holder and holder-support system position accuracy is within ±0.0002" in a z-axis and within ±0.001" in the x and y axes.

In another aspect, the invention relates to a method of transferring fluid from a source reservoir to a target reservoir. The method includes providing a dispensing head for aspirating and dispensing fluids, the dispensing head constrained to move along a single axis. The method also includes providing a fluid-source holder for holding a source-reservoir, the fluid-source holder constrained to move in a plane substantially perpendicular to the single axis, the fluid-source holder including an apparatus for repeatably positioning the fluid-source holder on a fluid-source holder support. In addition the method includes the step of providing a fluid-target holder for holding a fluid-target reservoir, the fluid-target holder constrained to move in a plane substantially perpendicular to the single axis, a plane of motion of the fluid-target holder displaced from a plane of motion of the fluid-source holder, the fluid-target holder including an apparatus for repeatably positioning the fluid-target holder on a fluid-target holder support. The steps of moving the fluid-source holder to position the source-reservoir beneath the dispensing head, lowering the dispensing head and aspirating fluid from the source-reservoir, raising the dispensing head, moving the fluid-target holder to position the fluid-target reservoir beneath the dispensing head, lowering the dispensing head and dispensing the fluid into the fluid-target reservoir are also included in the method.

In another aspect, the invention relates to a microarrayer assembly for depositing minute droplets of fluid on a substrate. The microarrayer includes a deposit element for depositing minute droplets of fluid onto a surface of a substrate and a removable substrate-holder for holding at least one substrate, the substrate-holder including an apparatus for precisely and repeatably positioning the substrate-holder on a substrate-holder support.

In one embodiment, the apparatus for precisely and repeatably positioning the substrate-holder on the substrate-holder support includes a first element for mating with a first datum disposed on the substrate-holder support, and for restricting movement of the removable substrate-holder along an x-axis and a mutually orthogonal y-axis and defining a first point in a z-axis, the z-axis mutually orthogonal to the x-axis and the y-axis. The apparatus also includes a second element for mating with a second datum disposed on the substrate-holder support, and for at least partially locating the removable substrate-holder along at least one of the x-axis and the y-axis while defining a second point in the z-axis. A third element is also included in the apparatus for mating with a third datum disposed on the substrate-holder support and defining a third point in the z-axis. In one embodiment, the first element forms a conical recess for mating with the first datum. In another embodiment, at least two of the elements are adjustable along the z-axis.

In one embodiment, the substrate-holder support further includes a datum plane defined by at least three datums including a first datum for engaging the substrate-holder and for restricting movement of the substrate-holder along an x-axis and a mutually orthogonal y-axis, and defining a first point in a z-axis, the z-axis mutually orthogonal to the x-axis and the y-axis. A second datum is also included for engaging the substrate-holder and for at least partially locating the substrate-holder along at least one of the x-axis and the y-axis and defining a second point in the z-axis. The third datum is provided for engaging the substrate-holder and for defining a third point in the z-axis. In one embodiment, the first datum includes at least a portion of a sphere for engaging a conical recess formed in the substrate-holder. In another embodiment the second datum is engageable with a linear recess formed in the substrate-holder.

The microarrayer assembly in other embodiments includes a removable fluid-reservoir for holding at least one fluid, the removable fluid-reservoir including an apparatus for repeatably positioning the removable fluid-reservoir on a fluid-reservoir holder support. In one embodiment, the microarrayer assembly also includes a removable fluid-reservoir holder for holding the removable fluid-reservoir, the fluid-reservoir holder including an apparatus for precisely and repeatably positioning the removable fluid-reservoir holder on the fluid-reservoir holder support. In one embodiment, the fluid-reservoir holder support moves in unison with the substrate-holder support.

In one embodiment, the apparatus for repeatably positioning the removable fluid-reservoir holder on the fluid-reservoir holder support includes a first element for mating with a first datum disposed on the fluid-reservoir holder support, and for restricting movement of the removable fluid-reservoir holder along an x-axis and a mutually orthogonal y-axis and defining a first point in a z-axis, the z-axis mutually orthogonal to the x-axis and the y-axis. The apparatus also includes a second element for mating with a second datum disposed on the fluid-reservoir holder support, and for at least partially locating the removable fluid-reservoir holder along at least one of the x-axis and the y-axis while defining a second point in the z-axis. A third element is also included in the apparatus for mating with a third datum disposed on the fluid-reservoir holder support and defining a third point in the z-axis. In one embodiment, the first element forms a conical recess for mating with the first datum. In another embodiment, at least two of elements are adjustable along the z-axis.

In yet another embodiment in accordance with the invention, the fluid-reservoir holder support includes a first datum for engaging the removable fluid-reservoir and for restricting movement of the removable fluid-reservoir along an x-axis and a mutually orthogonal y-axis, and defining a first point in a z-axis, the z-axis mutually orthogonal to the x-axis and the y-axis. A second datum is also included for engaging the removable fluid-reservoir and for at least partially locating the removable fluid-reservoir along at least one of the x-axis and the y-axis and defining a second point in the z-axis. The fluid-reservoir holder also includes a third datum for engaging the removable fluid-reservoir and defining a third point in the z-axis. In one embodiment, the first datum includes at least a portion of a sphere for engaging a conical recess disposed on the removable fluid-servoir. In yet another embodiment, the second datum is engageable with a linear recess disposed on the removable fluid-reservoir.

The microarrayer assembly can also include a variety of other features. For instance, in one embodiment, the deposit element comprises a solid pin. The microarrayer assembly can include a fluid-reservoir storage and an apparatus for moving a fluid-reservoir between the fluid-reservoir storage and the fluid-reservoir holder support. In addition, a sensor can be included to determine presence of a fluid-reservoir in a bay of the fluid-reservoir storage. Similarly, the microarrayer assembly can include a substrate-holder storage and an apparatus for moving a substrate-holder between the substrate-holder storage and the substrate-holder support. A sensor can also be included to determine presence of a substrate-holder in a bay of the substrate-holder storage. In one embodiment, the substrate-holders are moved from the substrate-holder storage to the substrate-holder support by moving the substrate-holder in a vertical direction within the substrate-holder storage to dispose the substrate-holder on the substrate holder support and moving the substrate-holder support in a horizontal direction to retract the substrate-holder support from the substrate-holder storage. In a further embodiment, the removable substrate-holders are at least one of removed from and added to the substrate-holder storage during active fluid capture and droplet deposition operations.

In one embodiment, the deposit element is constrained to move along a z-axis and the substrate-holder is constrained to move in a plane substantially perpendicular to the z-axis when disposed beneath the deposit element. In yet another embodiment, the deposit element is constrained to move along a z-axis and the fluid-reservoir is constrained to move in a plane substantially perpendicular to the z-axis when disposed beneath the deposit element. In a further adaptation, the fluid-reservoir plane of motion is parallel to and displaced from the substrate-holder plane of motion when disposed beneath the deposit element. In a further embodiment, the fluid-reservoir is moveable independently of but in coordination with the substrate-holder and the deposit element.

In one embodiment, the removable fluid-reservoir is a multi-well plate having 96 wells or a multiple thereof. The substrate, in another embodiment, may also include a multi-well plate.

In a further adaptation, the microarrayer assembly includes a first printhead and a second printhead, each printhead for holding at least one deposit element, where the first printhead and the second printhead are optionally arranged for moving independently of each other in separate parallel axes.

In another embodiment, the removable substrate-holder includes a top surface and a bottom surface spaced from the top surface, an aperture extending at least partially between the top surface and the bottom surface, an intersection of the aperture and the top surface defining a perimeter and at least three reference points proximate the perimeter and defining a reference plane, the reference points for engaging a top surface of the substrate when the substrate is disposed in the aperture. Means may be included in the removable-substrate holder to bias the substrate against the at least three reference points. In yet another embodiment, the removable substrate-holder includes a removable substrate-mounting fixture, the substrate-mounting fixture including a locking element for securing the substrate-mounting fixture into the removable substrate-holder, the substrate-mounting fixture for holding at least one substrate.

In one embodiment of the microarrayer assembly, a sensor is included to measure a distance from the deposit element to a top surface of the substrate. In addition, a motion control system may be included to dynamically adjust a motion of the deposit element in response to the sensor measurement to deposit the minute droplet of fluid onto the substrate without the deposit element contacting the substrate.

In a further embodiment, the microarrayer assembly includes a barcode reader for optically sensing labels secured to at least one of the substrate-holder, the substrate, the fluid-reservoir holder, and the fluid-reservoir. In another embodiment at least one of the substrate-holder and the fluid-reservoir holder further comprise a tracking device. The tracking device includes at least one of a barcode, a radio-frequency identification (RFID) transponder programmed with a unique code readable by an RFID interrogator by non-contact means, and a semi-conductor memory device programmed with a unique code. The unique code disposed on the semi-conductor memory device is readable by at least one of an electric sensor and an external sensor that is in communication with the semi-conductor memory device through at least one of optical, infra-red, and radio-frequency communication. In addition, the microarrayer assembly can include a means for locally storing and updating information on at least one of the substrate, the substrate-holder, the fluid reservoir, and the fluid-reservoir holder. The means includes at least one of a radio-frequency identification (RFID) transponder and a semi-conductor memory device dynamically programmable onto the at least one of the substrate, the substrate-holder, the fluid reservoir, and the fluid-reservoir holder. The transponder is readable by an RFID interrogator by non-contact means and the semi-conductor memory device is readable by at least one of electrical contact and an external sensor that is in communication with the semi-conductor memory device through at least one of optical, infra-red, and radio-frequency communication.

In one embodiment, overall substrate-holder and substrate-holder support system position accuracy is within ±0.002" in a z-axis and within ±0.01" in x and y axes. In a preferred embodiment, overall substrate-holder and substrate-holder support system position accuracy is within ±0.001" in az-axis and within ±0.005" in x and y axes. In a more preferred embodiment, overall substrate-holder and substrate-holder support system position accuracy is within ±0.0002" in a z-axis and within ±0.001" in x and y axes.

In another aspect, the invention relates to a microarrayer assembly for depositing minute droplets of fluid on a substrate. The microarrayer assembly includes a plurality of deposition engines operating cooperatively. Each deposition engine includes a deposit element for depositing minute droplets of fluid onto a surface of a substrate and a support for holding at least one of a substrate-holder and a fluid reservoir, the support including an apparatus for precisely and repeatably positioning at least one of the substrate-holder and the fluid reservoir on the support.

In one embodiment, the microarrayer assembly further includes means to transfer at least one of the substrate-holder and the fluid-reservoir between the deposition engines. In addition, the microarrayer assembly can include at least one hotel for storing at least one of the substrate-holder and a fluid-reservoir and a means to transfer at least one of the substrate-holder and the fluid-reservoir between the hotel and at least one deposition engine.

In another aspect, the invention relates to a method for depositing minute droplets of fluid on a substrate and a microarray produced in accordance with the method. The method includes the step of loading a substrate-holder onto a substrate-holder support, the substrate-holder for holding at least one substrate and the substrate-holder including an apparatus for precisely and repeatably positioning the substrate-holder on the substrate-holder support. In addition, the method includes the steps of providing fluid to a deposit element, the deposit element moveable relative to the substrate-holder and transferring a droplet of fluid from the deposit element to the substrate.

In one embodiment, the method also includes the step of transferring the substrate-holder between a substrate-holder storage and the substrate-holder support. The method may also include the step of loading a fluid-source holder onto a fluid-source holder support, the fluid-source holder for holding at least one fluid source and including an apparatus for precisely and repeatably positioning the fluid-source holder on the fluid-source holder support. In a further embodiment, the method also includes the steps of transferring the fluid-source holder from a fluid-source holder storage to the fluid-source holder support, capturing fluid from the fluid-source with the deposit element, and transferring the fluid-source holder from the fluid-source holder support to the fluid-source holder storage. In one embodiment, the deposit element includes a solid pin.

In one embodiment, the substrate-holder support includes a first datum for engaging the substrate-holder and for restricting movement of the substrate-holder along an x-axis and a mutually orthogonal y-axis, and defining a first point in a z-axis, the z-axis mutually orthogonal to the x-axis and the y-axis. The substrate-holder support also includes a second datum for engaging the substrate-holder and for at least partially locating the substrate-holder along at least one of the x-axis and the y-axis and defining a second point in the z-axis. Further, the substrate-holder support includes a third datum for engaging the substrate-holder and defining a third point in the z-axis. In one embodiment, the first datum includes at least a portion of a sphere for engaging a conical recess disposed on the substrate-holder. In another embodiment, the second datum is engageable with a linear recess disposed on the substrate-holder.

In one embodiment, the substrate-holder includes a first element for mating with a first datum, and for restricting movement of the substrate-holder along an x-axis and a mutually orthogonal y-axis and defining a first point in a z-axis, the z-axis mutually orthogonal to the x-axis and the y-axis. The substrate-holder further includes a second element for mating with a second datum, and for at least partially locating the substrate-holder along at least one of the x-axis and the y-axis while defining a second point in the z-axis. In addition, the substrate-holder includes a third element for mating with a third datum and defining a third point in the z-axis. In one embodiment, the first element forms a conical recess for mating with the first datum.

In yet another embodiment, the method may include the step of moving a fluid reservoir to a position beneath the deposit element, the deposit element constrained to travel substantially along a vertical axis and the fluid reservoir being constrained to travel in a plane substantially perpendicular to the vertical axis when disposed beneath the deposit element. The steps of lowering the deposit element to capture fluid from the fluid reservoir, raising the deposit element relative to the fluid reservoir, moving the substrate-holder to a position beneath the deposit element, the substrate-holder constrained to travel in a plane parallel substantially perpendicular to the vertical axis when disposed beneath the deposit element and lowering the deposit element to deposit the fluid on the substrate can also be included in the method.

In another aspect, the invention relates to a method of depositing droplets of fluid on a substrate and a microarray produced in accordance with the method. The method includes the step of moving a fluid reservoir to a position beneath a printhead, the printhead being constrained to travel along a vertical axis and the fluid reservoir being constrained to travel within a plane substantially perpendicular to the vertical axis when disposed beneath the printhead. Also included in the method are the steps of lowering the printhead to capture fluid from the fluid reservoir, raising the printhead relative to the fluid reservoir and moving a substrate to a position beneath the printhead, the substrate constrained to travel within a plane parallel to, but displaced from, the plane of motion of the fluid reservoir when disposed beneath the printhead. The method also includes the step of lowering the printhead to deposit the fluid on the substrate.

In one embodiment, the method further includes the step of moving the fluid reservoir away from the axis of motion of the printhead prior to depositing the fluid on the substrate. In a further embodiment, the step of moving the fluid reservoir to a position beneath the printhead includes moving the substrate in tandem with the fluid reservoir. In yet another embodiment, the step of moving the substrate beneath the printhead precedes the step of moving the fluid reservoir away from the axis of motion of the printhead.

In another aspect, the invention relates to a method of depositing minute droplets of fluid on a substrate. The method includes the step of arranging a plurality of deposition engines cooperatively, each deposition engine including a deposit element for depositing minute droplets of fluid onto a surface of a substrate. The method also includes the step of transferring at least one holder between the deposition engines, the holder for holding at least one of a substrate and a fluid-reservoir, the holder including an apparatus for precisely and repeatably positioning the holder on a support.

In one embodiment, each deposition engine comprises a plurality of printheads. In another embodiment, the method includes the step of transferring at least one holder from a hotel to at least one deposition engine. The holders may be removed from and added to the hotel during active fluid capture and droplet deposition operations.

In another aspect, the invention relates to a microarrayer assembly for depositing minute droplets of fluid on a substrate. The microarrayer includes a printhead for depositing fluids on the substrate, a fluid reservoir including at least one well for supplying fluid to the printhead, and a sensor for measuring depth of fluid in the at least one well.

In another aspect, the invention relates to a method for depositing minute droplets of fluid on a substrate. The method includes the step of moving a fluid reservoir to a position beneath a first printhead, the first printhead including at least one deposition element and constrained to move along a vertical axis, the fluid reservoir constrained to move in a plane substantially perpendicular to the vertical axis when disposed beneath the first printhead. Also included in the method are the steps of moving the printhead relative to the fluid reservoir to dip the deposition element into the fluid reservoir, raising the first printhead relative to the fluid reservoir, and moving a substrate beneath the first printhead while simultaneously moving the fluid reservoir beneath a second printhead, the substrate constrained to move in a plane parallel to, but displaced from, the plane of motion of the fluid reservoir. The steps of lowering the first printhead to deposit a fluid droplet on the substrate and lowering the second printhead to capture fluid from the fluid reservoir, and raising the first printhead and the second printhead above the planes of motion of the substrate and the fluid reservoir are also included in the method. The method also includes the steps of moving the substrate under the second printhead while simultaneously moving the fluid reservoir to a position beneath the first printhead, and lowering the second printhead to deposit a fluid droplet on the substrate and lowering the first printhead to capture fluid from the reservoir.

In one embodiment, the method includes the step of moving the substrate under at least one of the first printhead and second printhead prior to moving the fluid reservoir away from at least one of the first printhead and the second printhead.

In another aspect, the invention relates to a method for depositing biological fluid samples onto a substrate to reduce non-specific binding in undesired locations on the substrate. The method includes the step of providing a substrate including a surface resistant to non-specific binding of biological material. A second step included in the method is depositing a first fluid droplet onto the substrate, the first fluid droplet including a binding agent that is bindable with the substrate and that is bindable to a biological material through at least one of electrostatic, covalent and chemical binding. The method also includes the step of depositing a second fluid droplet onto the deposition location of the first fluid droplet, the second fluid droplet including a biological material for binding with the binding agent.

In one embodiment, the method includes the step of depositing additional fluid droplets on the deposition location of the first fluid droplet to deactivate the binding properties of any unbound binding agent and biological material remaining from the first droplet and the second droplet.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. In addition, the drawings are not necessarily to scale, emphasis instead generally being placed upon illustrating the principles of the invention. In the following description, various embodiments of the present invention are described with reference to the following drawings, in which.

DETAILED DESCRIPTION

Embodiments of the present invention are described below. It is, however, expressly noted that the present invention is not limited to these embodiments, but rather the intention is that variations, modifications, and equivalents that are apparent to the person skilled in the art are also included. The detailed description is written in three parts. The first part discusses Microarrayers, the second part discusses Tissue Arrayers, and the third part discusses Fluidics Robots. Since the term "microarray" is often used in the art to describe both an array of fluid samples and an array of tissue samples, a distinction in terminology is used in this disclosure. The terms "microarray" or "spotted microarray" are used to refer to an array of samples deposited in a fluid state upon a substrate in the form of minute fluid droplets. The terms "tissue microarray" or "tissue array" are used to refer to an array of tissue samples deposited in semi-solid or solid form.

Similarly, the term "microarrayer", in this disclosure will be used to refer to a device for producing microarrays of fluid droplets. The terms "arrayer" and "spotter" may be used synonymously for the term microarrayer. The term "tissue arrayer", in this disclosure, will be used to refer to a device for producing tissue arrays.

1) Microarrayers

Figure 1:
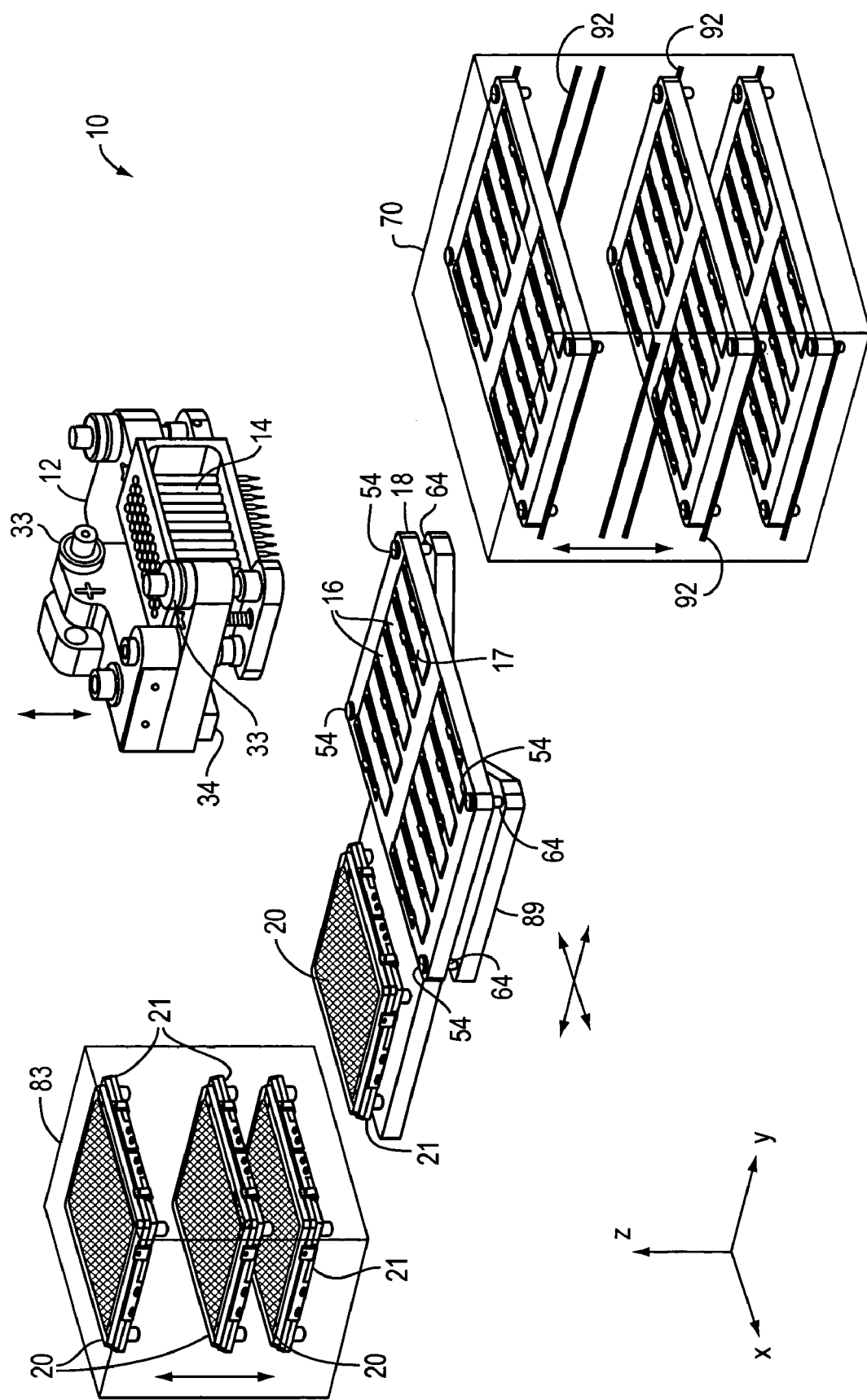
FIG. 1 is a schematic perspective view of a microarrayer in accordance with one embodiment of the invention.

With reference to FIG. 1, in one embodiment of a microarrayer assembly 10 in accordance with the invention, the microarrayer assembly 10 includes a printhead 12 which holds a plurality of deposit elements 14. Also included in the microarrayer assembly 10 are substrates 16 which are held on a substrate-holder 18 which is in turn mounted on a platen 89. A fluid reservoir 20, for instance a microplate or microtiter plate, is also included in the microarrayer assembly 10. The fluid reservoir 20 is held on a fluid reservoir holder 21 and, in turn, the fluid reservoir holder 21 is held on the platen 89. In one embodiment, the printhead 12 and the platen 89 are each mounted on motion stages (not shown). The motion stages enable the printhead 12 and the platen 89 to move relatively in relation to each other so that the deposit elements 14 can acquire fluid from the fluid reservoir 20 and deposit the fluid on the substrates 16.

a) Deposit Elements

A variety of deposit elements 14 may be used in accordance with the invention including ink-jet dispensers, pens, quill pins, and solid pins. Ink jet dispensers 14 eject drops onto a substrate 16 using, for instance, a piezoelectric crystal which deforms in response to a voltage to squeeze a minute droplet of fluid from a minute orifice in the dispenser. Fluid samples to be dispensed from an ink jet device 14 are either fed directly to the device, for example via tubing, or, alternatively, the sample fluid can be aspirated into the ink jet device 14 from a fluid reservoir 20.

In embodiments using pen printing, a pen-like device 14 such as a narrow capillary tube is first dipped into the fluid reservoir 20 to aspirate fluid, and then used to deposit a fluid droplet upon the substrate 16 by applying pressure to the fluid within the capillary.

Quill-pin printing embodiments in accordance with the invention use a split pin 14 or pin with a slit near its tip. The quill pin 14 is first dipped in the fluid reservoir 20 to capture fluid in the slit between the two segments of the pin 14. This local fluid reservoir in the slit is then used to re-supply the tip of the pin when the pin 14 is touched or tapped upon the surface of the substrate 16.

Solid pins 14 may also be used as the deposit element 14 in accordance with other embodiments of the invention. When used as the deposit element 14, solid pins with tip diameters between about 25 micrometers to about 700 micrometers may be used, and in another embodiment, solid pins having diameters between about 70 micrometers to about 300 micrometers may be used. The tip of the pin is dipped into a fluid reservoir 20 (for instance into fluid held within a well of a microplate 20) from which the pin 14 is then withdrawn such that a droplet of fluid is captured on the tip of the pin 14. The pin 14 is then moved, relatively, to touch the tip of the pin 14, or to touch the fluid droplet adhered to the tip of the pin 14, onto a substrate 16 and thereby transfer some of the fluid to the substrate 16.

Figure 2A:
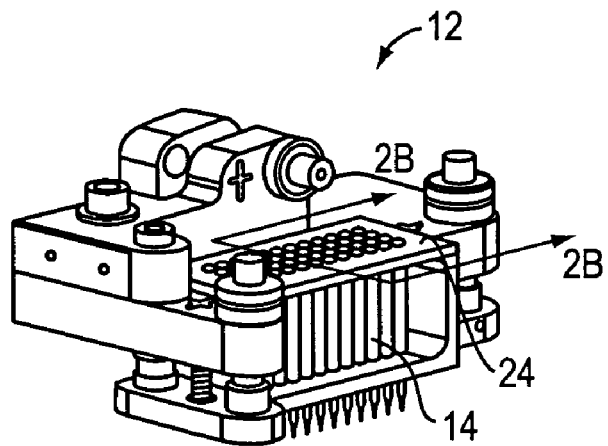
FIG. 2A is a schematic perspective view of a printhead including a pin support assembly in accordance with one embodiment of the invention.
Figure 2B:
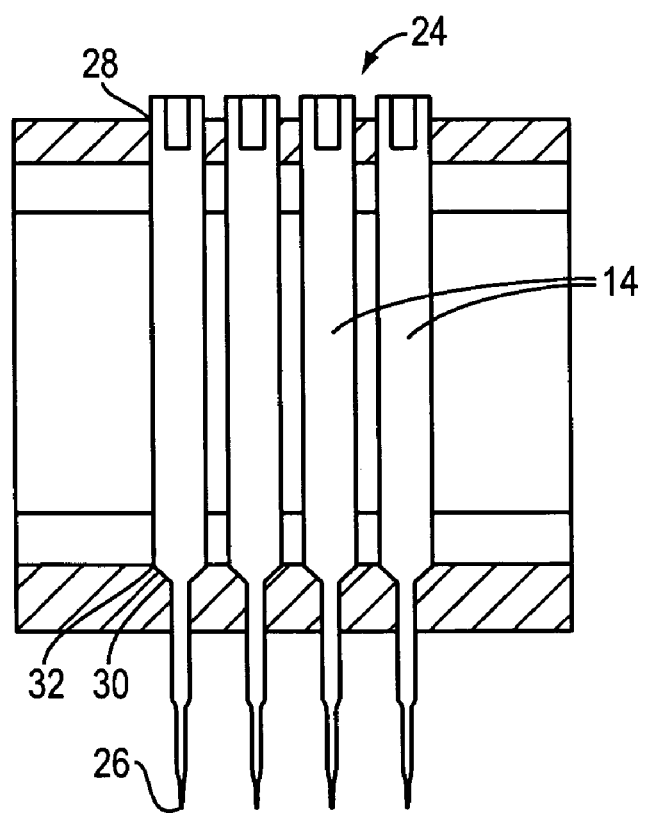
FIG. 2B is a schematic cross-sectional view of the pin support assembly of FIG. 2A taken at line 2B-2B in FIG. 2A.

With reference to FIGS. 2A-2B, solid pins 14 are shown held within a pin-support assembly 24 that maintains precise positioning of a tip 26 of the pin 14 in a horizontal plane while allowing compliance in a vertical dimension. The solid pins 14 in various embodiments, are stepped pins and tapered pins. The pin support assembly 24 includes upper holes 28 and lower holes 30 through which the pins 14 extend. The upper holes 28 are formed slightly larger than the width (the diameter of the pin, if of circular cross-section) of the pin's upper section such that the pin 14 can move vertically within the pin support assembly 24, but is constrained to move minimally in the horizontal plane. As illustrated, the lower holes 30 each include a conical seat 32 that matches a similar profile formed on the pin 14. The conical seat 32 serves both to a) provide a lower restraint to vertical motion of the pin 14, thereby defining the vertical location of the tip 26 of the pin 14 of known length and proportions, and b) to precisely locate the lower section of the pin 14, and thereby the pin tip 26, in the horizontal plane. In one embodiment, the pin 14 is pushed against the conical seat 32 by the weight of the pin 14 alone. In another embodiment, a biasing means, such as a vertically acting spring is used to thrust the conical section of the pin 14 onto the seat 32. It will be appreciated that other techniques for maintaining the position of the pin tip 26 may be used, and the above example should not be considered limiting.

With reference to FIGS. 1-2B, a multiplicity of deposit elements 14 are held in the printhead 12 which greatly enhances the rate at which droplets may be deposited on a substrate 16. Typically, the deposit elements 14 are spaced apart at a distance corresponding to the center-to-center well spacing of the multi-well fluid reservoir 20 being used, such as a microplate 20 having 24, 48, 96, 384, 1536 or 3456 wells, or a microplate having a number of wells being a multiple of any of these numbers. One advantage of the use of solid pins 14 compared to quill-pins or pens is that their relatively narrow tips 26 allows their penetration into small, high density wells, such as those in standard 1536 and 3456 microplates 20. Similarly, the narrow bodies of solid pins enable printheads 12 to contain a higher density of pins 14 within a given area. Solid-pin printheads 12 of 192 pins or more can readily be used in combination with 1536-well microplates 20.

Once the deposit elements 14 are mounted in the printhead 12, planar adjustments of the tips 26 are desirable to bring the plane of the tips 26 parallel to a plane of the substrates 16. For example, precision adjustments to the pitch, roll and yaw between fixed reference elements of the printhead 14 and the pin-support assembly 24 may be made with adjustment screws 33.

b) Substrates and Substrate Holders

Microarrays of fluid droplets can be spotted on a wide variety of substrates 16. In one embodiment, the substrate 16 is in the form of a glass slide, such as a microscope slide. The substrate 16, in another embodiment, is a multi-well plate such as a micro-titer plate with flat-bottomed wells. The benefit of using such a multi-well plate is that the fluids spotted on the flat bottom of each well can be independently assayed. This is of significant value for applications such as drug discovery, high-throughput screening and toxicogenomics. The well-plate format for the substrate 16 is well suited to applications requiring a multiplicity of parallel tests on a limited number of fluid samples, typically up to several thousand in number.

In other embodiments in accordance with the invention, the substrates may be selected from a variety of materials and forms, all of which are included within the scope of the present invention. Such materials include, but are not limited to, metal, plastic, nylon, semiconductor and ceramic materials, glass plates, clear or glass-bottomed well plates or similar multi-well structures allowing for further independent chemical or biological processing.

In another embodiment, a top surface 17 of the substrate 16 is coated with a material that will bind biological molecules. In one embodiment, the coating has hydrophobic properties to minimize the spreading of the droplet over the top surface 17 of the substrate 16. Many coatings have been developed for microarray substrates 16 and will be familiar to those skilled in the art.

As mentioned earlier, a limitation of the prior art is that substrate mounting arrangements have been bottom-referenced on a platen, i.e. the substrate such as a glass slide, is mounted such that its bottom surface rests upon the top surface of the platen. Variability in the thickness of the substrates can create uncertainty in the height of the surface upon which fluid droplets will be deposited and can cause undesirable variations in droplet deposition from substrate to substrate.

With reference to FIG. 1, in one embodiment in accordance with the invention, this limitation is overcome by providing a distance measurement sensor 34 (in one embodiment the distance measurement sensor is mounted to the printhead 12 to minimize uncertainties in absolute position) to accurately measure the distance between the printhead 12 and the top surface 17 of the substrate 16 onto which fluid droplets are to be deposited. Precision motion control elements can then be employed to adjust the relative distance between the tips 26 of the deposit elements 14 and the substrate 16 to effect contact of the droplet and the top surface 17 of the substrate 16. The distance measurement sensor, for example, may be:

a) capacitive, wherein the change in capacitance as an element approaches an object or surface is sensed to measure distance, b) inductive, wherein the change in inductance as an element approaches an object or surface is sensed to measure distance, c) conductive, wherein conduction of an electric current or signal (continuous or alternating current) is either established or broken when an element touches an object or surface, d) magnetic, wherein the change in magnetic flux as an element approaches an object or surface is sensed to measure distance, e) optical, including, but not limited to i) laser interferometry distance measurement, ii) optical switching (in which an optical beam is either established or broken as a result of physical contact of an element or an optical beam with an object or surface), iii) optical displacement sensing, in which the distance to a surface is measured by measuring the displacement of a beam that is reflected from that surface at an angle other than normal incidence, or f) radar, sonar or laser-radar based, with distance measurement using pulsed transmissions or modulated continuous-wave transmissions.

Figure 3:
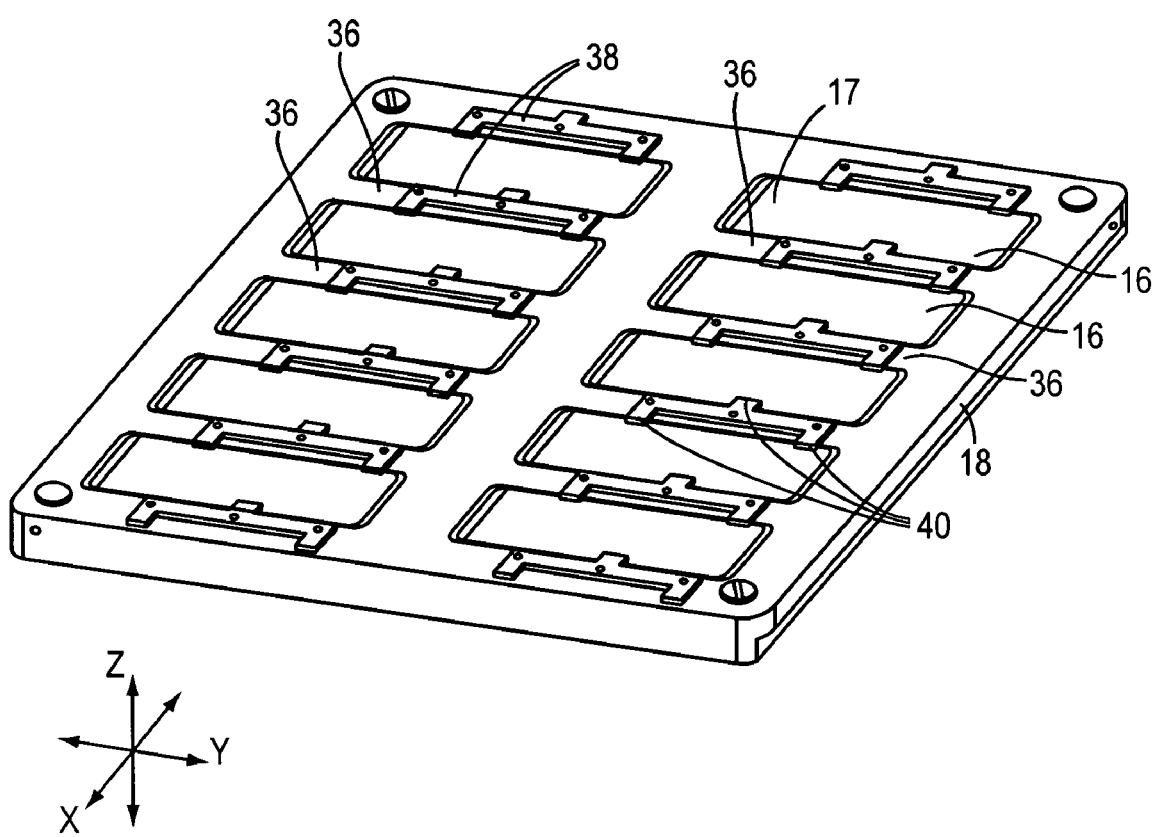
FIG. 3 is a schematic perspective view of a top referencing substrate-holder in accordance with one embodiment of the invention.

In another embodiment, variability in the thickness of the substrates 16 is overcome by top referencing the substrates 16 in the substrate-holder 18. With reference to FIG. 3, an arrangement for top-referencing a substrate 16 in a substrate-holder 18 is illustrated. The top surface 36 of the substrate-holder 18 (or at least those parts of the top surface 36 around the locations where the substrates 16 are mounted) is machined or constructed to be precisely co-planar. Precisely machined brackets 38 are coupled to the machined top surface of the substrate-holder 18 such that portions 40 of the brackets 38 protrude over a recess in which the substrates 16 are disposed and present a three-point support to define a plane against which the top surface 17 of the substrate 16 rests. In this way, the top surface 17 of each substrate 16 will be substantially coplanar with the top surface 17 of every other substrate 16 on the substrate-holder 18, regardless of the individual thicknesses of the substrates 16. Resilient spring clips press the substrate 16 against the protruding portions 40 of the bracket 38 from below.

Alternative methods for top-referencing the substrate 16 in the substrate-holder 18 exist. For example, rather than using brackets, the reference surface 36 onto which the top surface 17 of the substrate 16 is pressed could be continuous and protrude over the aperture which receives the substrate 16. All such alternative realizations that have the effect of precisely locating the top surface 17 of the substrate 16 in the same plane are included within the scope of the present invention.

Figure 4A:
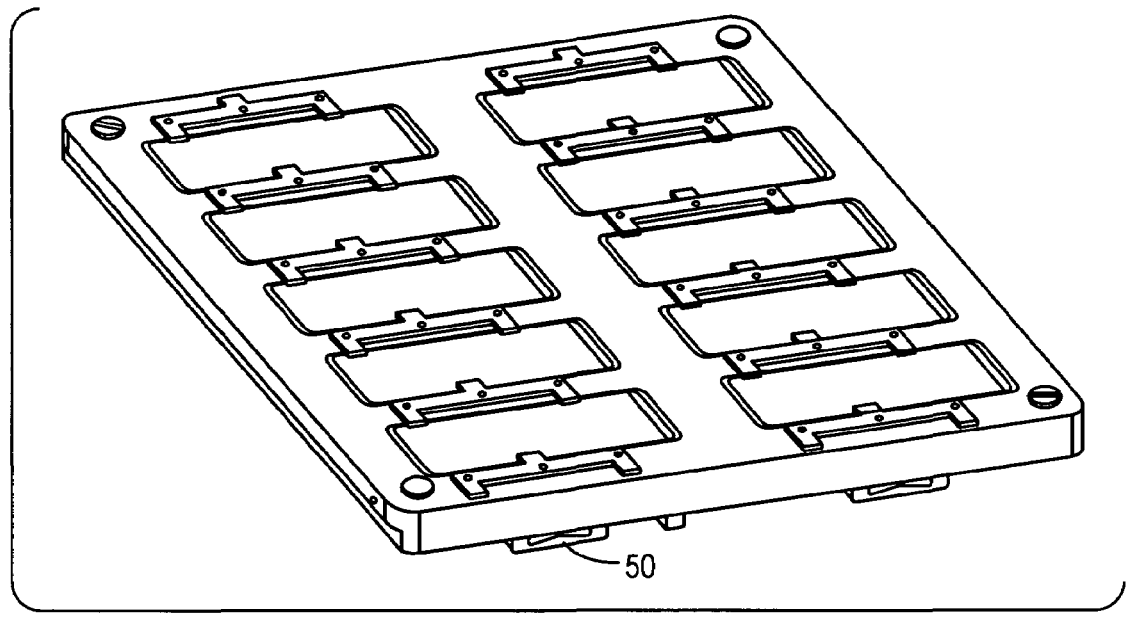
FIGS. 4A-4B are schematic perspective views of a top-referenced substrate-holder and a detachable substrate-mounting fixture for securing the substrate to the substrate-holder in accordance with one embodiment of the invention.
Figure 4B:
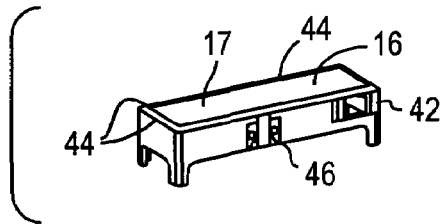
Figure 4C:
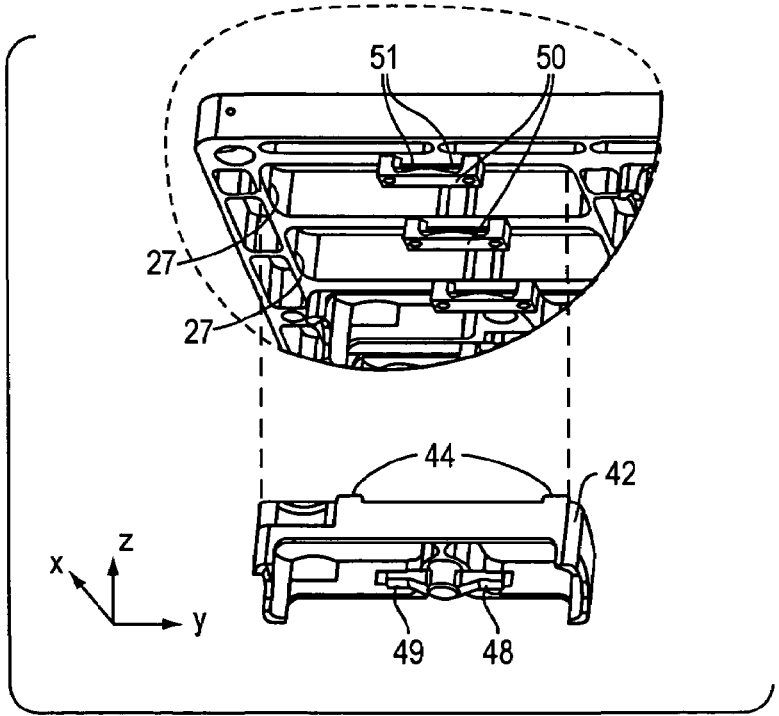
FIG. 4C is a schematic exploded perspective view of the top-referenced substrate-holder and the detachable substrate-mounting fixture of FIGS. 4A-4B.

With reference to FIGS. 4A-4C, in another embodiment, the substrate 16 is initially mounted on a detachable substrate-mounting fixture 42 that is, in turn, coupled to the substrate-holder 18 such that the top surface 17 of the substrate 16 is pressed upon the aforementioned reference surfaces 40 of the substrate-holder brackets 38. The substrate-holder 18 includes recesses 27 designed to accept the slide-mounting fixture 42 with the substrate 16 mounted upon it. The substrate 16 is referenced in the substrate-mounting fixture 42 at one end and on one side by fixed tabs 44 that do not extend above the top surface of the substrate 16. The substrate 16 is held against the tabs 44 by a spring clip 46 which exerts pressure on the side of the substrate 16, but does not extend above the top surface 17 of the substrate 16. With reference to FIG. 4C, a retaining device 48, with projections 49 for twisting the device 48 by finger action, is mounted on the bottom surface of the substrate-mounting fixture 42. The retaining device 48 is free to rotate around a vertical z-axis. The retaining device 48 is mounted on a compression spring (not shown) which pushes it away from the bottom surface of the substrate-mounting fixture 42 against a restraint which limits its motion away from the substrate-mounting fixture 42. Two bridges 50 with cam surfaces 51 formed on upper surfaces facing the substrate-holder 18 are firmly coupled to the substrate-holder 18 at either side of the recess 27. The substrate-mounting fixture 42 is inserted into the recess 27 in the lower side of the substrate-holder 18 until the top surface 17 of the substrate 16 contacts the reference surfaces 40 of the bracket 38 (the reference surfaces 40 being coplanar for all slide-mounting fixture recesses). The retaining device 48 is rotated, such that its projections 49 engage and slide over the cam surfaces 51 of the bridges 50. This action compresses the spring and causes the top surface 17 of the substrate 16 to press firmly against the reference surfaces 40 of the substrate-holder bracket 38. Detents at the centers of the cam surfaces 51 provide a position in which the retaining device 48 securely rests in a "locked" position.

The repeatable, accurate, top-referenced mounting structures of the present invention enable non-contact deposition without a substrate height position measurement sensor 34. Alternatively if such a sensor 34 is beneficial, a single measurement may suffice for all substrates 16 on the substrate-holder 18.

Figure 5A:
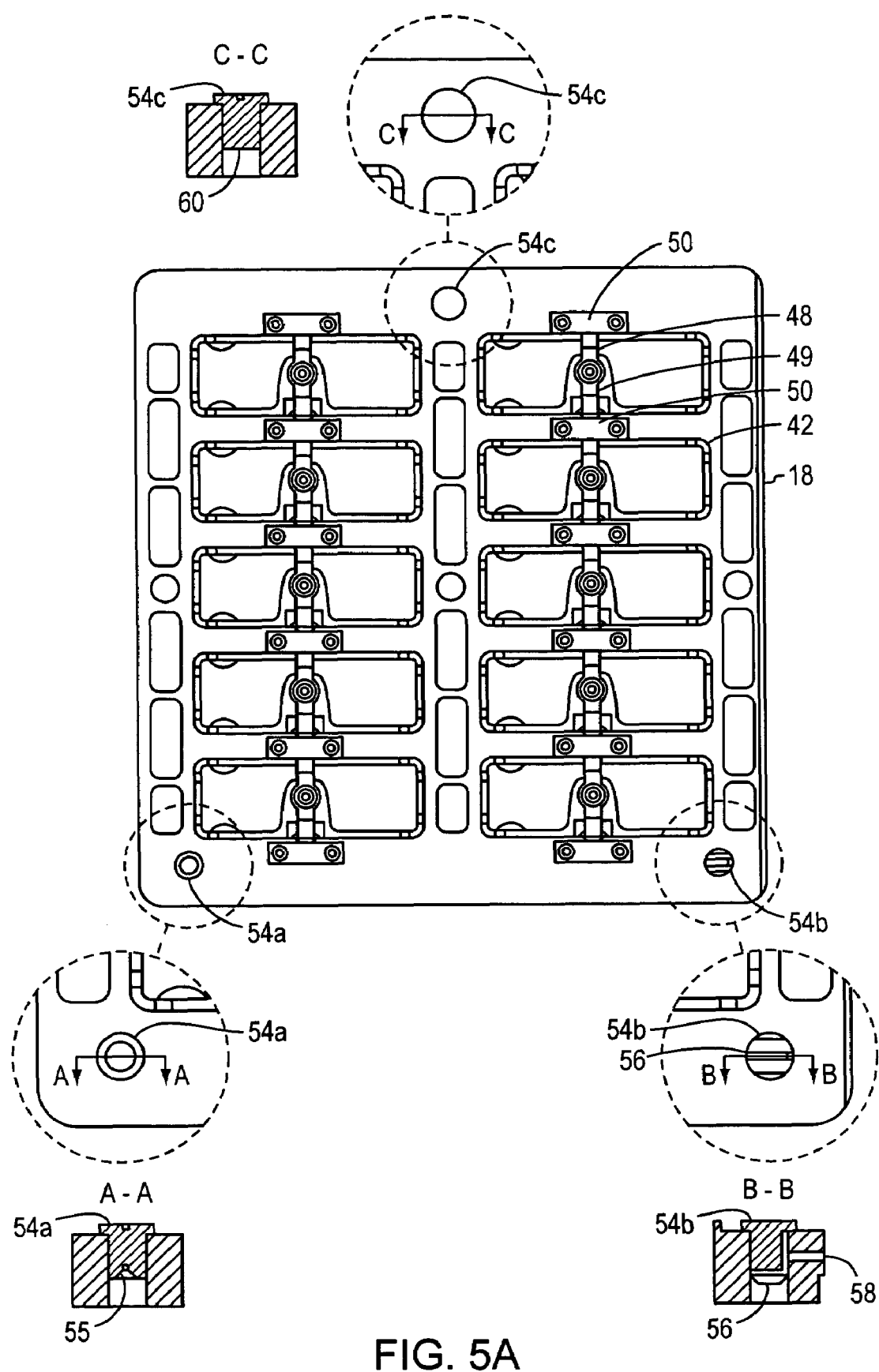
FIG. 5A is a schematic bottom view of a substrate-holder including inserts for mating with datums disposed on a substrate-holder support in accordance with one embodiment of the invention.

With reference to FIG. 5A, in another embodiment, the substrate-holder 18 includes an apparatus for mounting the substrate-holder 18 on a substrate-holder support 19, such that the substrates 16 may be precisely positioned repeatedly in a defined plane and at a defined location in that plane.

Reference surfaces are machined or formed on three inserts 54a, 54b, and 54c that are securely affixed in two corners of the substrate-holder 18 and at a mid-point on the far side of the substrate-holder 18 as illustrated. In one embodiment, the insert 54a includes a conically-shaped reference surface 55. The insert 54a is secured into the substrate-holder 18, for instance, by screwing the insert 54a into the substrate-holder 18, and then optionally fastening the insert 54a into position using an adhesive. The insert 54a, in one embodiment, is made from a hardened metal. In other embodiments, materials that are machinable, while also being non-deformable may be used. The insert 54a is engageable with a datum disposed on a substrate-holder support 19 to restrict movement of the substrate-holder 18 along an x-axis and a mutually orthogonal y-axis and defining a first point in a z-axis, where the z-axis is mutually orthogonal to the x-axis and the y-axis.

The insert 54b in the adjacent corner of the substrate-holder includes a V-groove reference surface 56. The insert 54b is inserted into the substrate-holder 18 in one embodiment such that the axis of the V-groove passes through the apex of the conical surface 55. The insert 54b may be secured to the substrate-holder 18 via a dowel pin 58 and adhesive. The insert 54b can be made from a hardened metal. The insert 54b is engageable with a second datum 64 disposed on the substrate-holder support 19 to locate the substrate-holder 18 along at least one of the x-axis and the y-axis while defining a second point in the z-axis.

The insert 54c on the far end of the substrate-holder 18 in one embodiment includes a flat (horizontal) surface 60. The insert 54c may be secured to the substrate-holder 18 via a screw thread and adhesive. The insert 54c may be made, for example, from a hardened metal. The insert 54c is engageable with a third datum disposed on the substrate-holder support 19 and defines a third point in the z-axis.

Figure 6A:
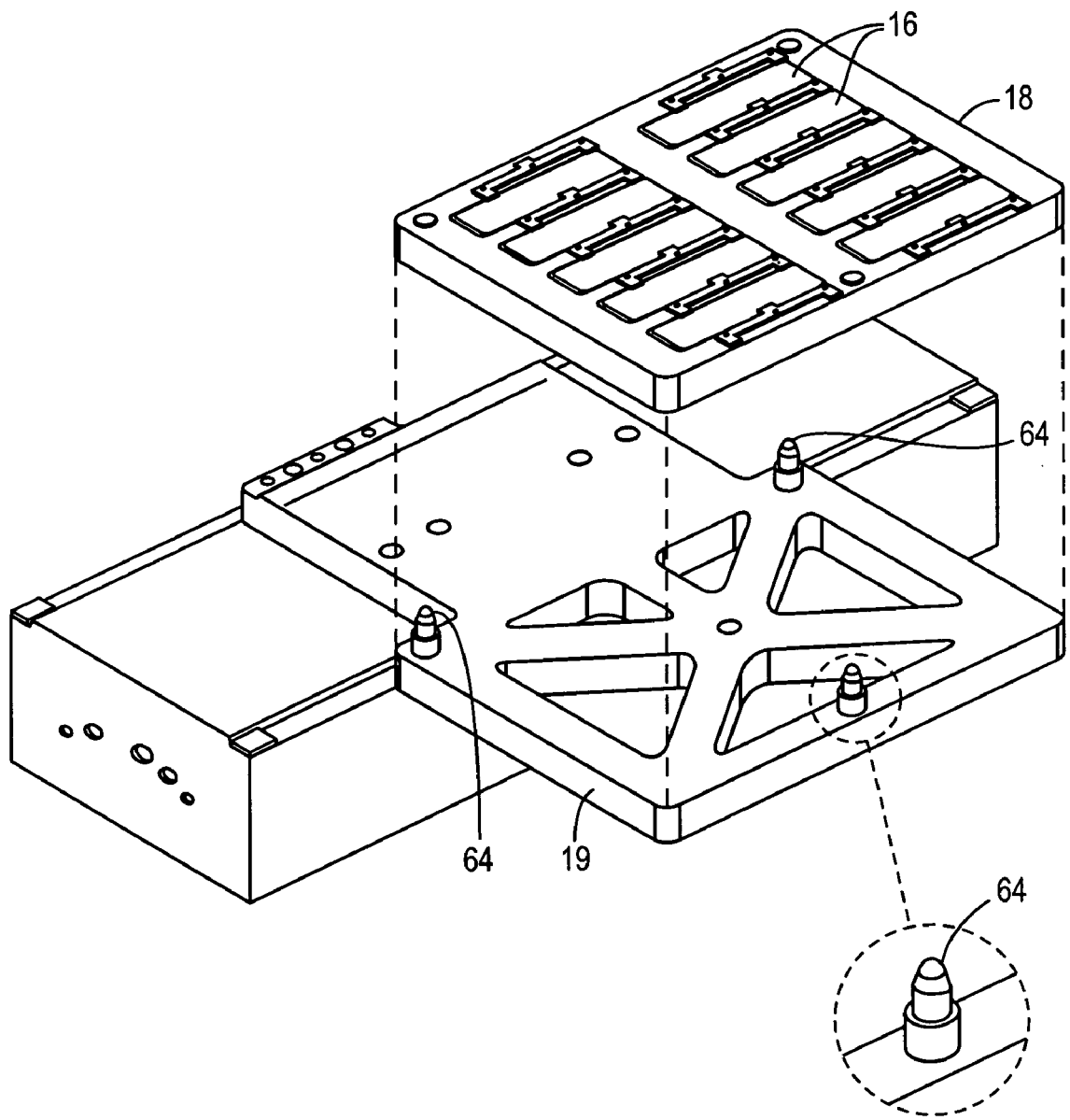
FIG. 6A is a schematic exploded perspective view of a substrate-holder support including datums for engaging reference surfaces disposed on a substrate-holder in accordance with one embodiment of the invention.

With reference to FIG. 6A, as mentioned, the reference surfaces 55, 56, 60 of the inserts 54a, 54b, 54c are designed to rest in contact with datums 64 disposed on the substrate-holder support 19. The datums are disposed on the substrate-holder support such that they align with the inserts 54a, 54b, and 54c disposed on the substrate-holder 18. In the illustrated embodiment, the datums 64 include hemispherical surfaces. In one embodiment, the hemispherical surfaces are provided by the top sides of hardened ball bearings mounted in precision seats set in optical-plane adjustment screws. The adjustment screws can be adjusted in height to set the substrate-holder 18 in the desired plane, and then locked in place.

In another embodiment, at least one datum 64 includes at least a portion of a spherical surface. In a further embodiment, at least one datum 64 includes a point formed by a pin. In another embodiment, the datums 64 are disposed on the substrate-holder 18 and the inserts are disposed on the substrate-holder support 19 (FIG. 6C).

In use, when the reference surfaces 55, 56, 60 of the inserts 54a, 54b, 54c are received on the datums 64, the datums 64 and the reference surfaces 55, 56, 60 locate the substrate-holder 18 in a selected plane. Further, if the substrate-holder 18 is removed from the substrate-holder support 19, and then re-seated on the substrate-holder support 19, the substrate-holder 18 will locate itself in the identical plane and in the identical location in the plane. In addition, any substrate-holder 18 with inserts 54a, 54b, 54c with reference surfaces set in the same positions and at the same heights (the heights are adjustable on two of the inserts 54a and 54c) will be accurately located in the same position in the same plane with respect to the substrate-holder support 19. This embodiment therefore permits a series of substrate-holders 18 to be sequentially loaded into the microarrayer assembly 10 without the loss of positional accuracy in locating the substrate-holders 18 on the substrate-holder support 19. In the illustrated embodiment, gravity loading is sufficient to firmly and accurately seat the substrate-holder 18 on the datums 64 of the substrate-holder support 19. In another embodiment, additional means for restraining the substrate-holder 18 against the datums 64 of the substrate-holder support 19 may be utilized. For instance, magnetic, electromagnetic, electrostatic, vacuum or mechanical means could be used for this purpose. In combination, the reference surfaces 55, 56, and 60 disposed on the substrate-holder 18, the datums 64 on the substrate-holder support 19, along with the top referencing of substrates 16 in a substrate-holder 18 provide an apparatus for accurately locating the top surface 17 of the substrates 16 in a known position in a known plane in the microarrayer assembly 10.

The capability to load substrate-holders 18 into and out of a microarrayer assembly 10 while maintaining positional accuracy of the substrates 16 in three dimensions serves to separate the choice of functional design of the microarrayer deposition apparatus from the selection of the substrate-handling capacity of the microarrayer assembly 10.

In one embodiment, overall substrate-holder and substrate-holder support system position accuracy is within ±0.002" in the z-axis and within ±0.01" in the x and y axes. In a preferred embodiment, overall substrate-holder and substrate-holder support system position accuracy is within ±0.001" in the z-axis and within ±0.005" in the x and y axes. In a more preferred embodiment, overall substrate-holder and substrate-holder support system position accuracy is within ±0.0002" in the z-axis and within ±0.001" in the x and y axes.

Figure 5B:
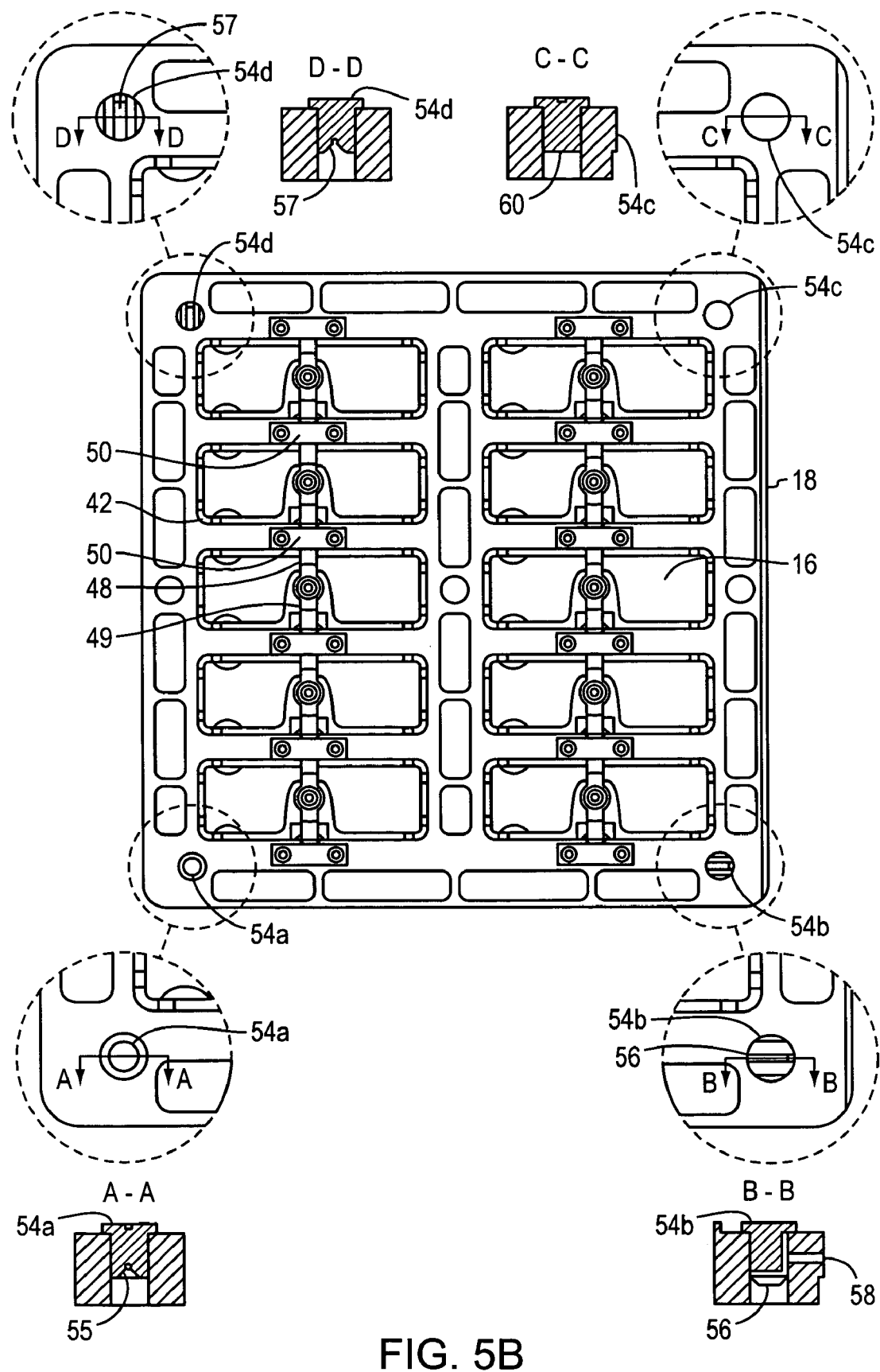
FIG. 5B is a schematic bottom view of a substrate-holder including inserts for mating with datums disposed on a substrate-holder support in accordance with one embodiment of the invention.
Figure 6B:
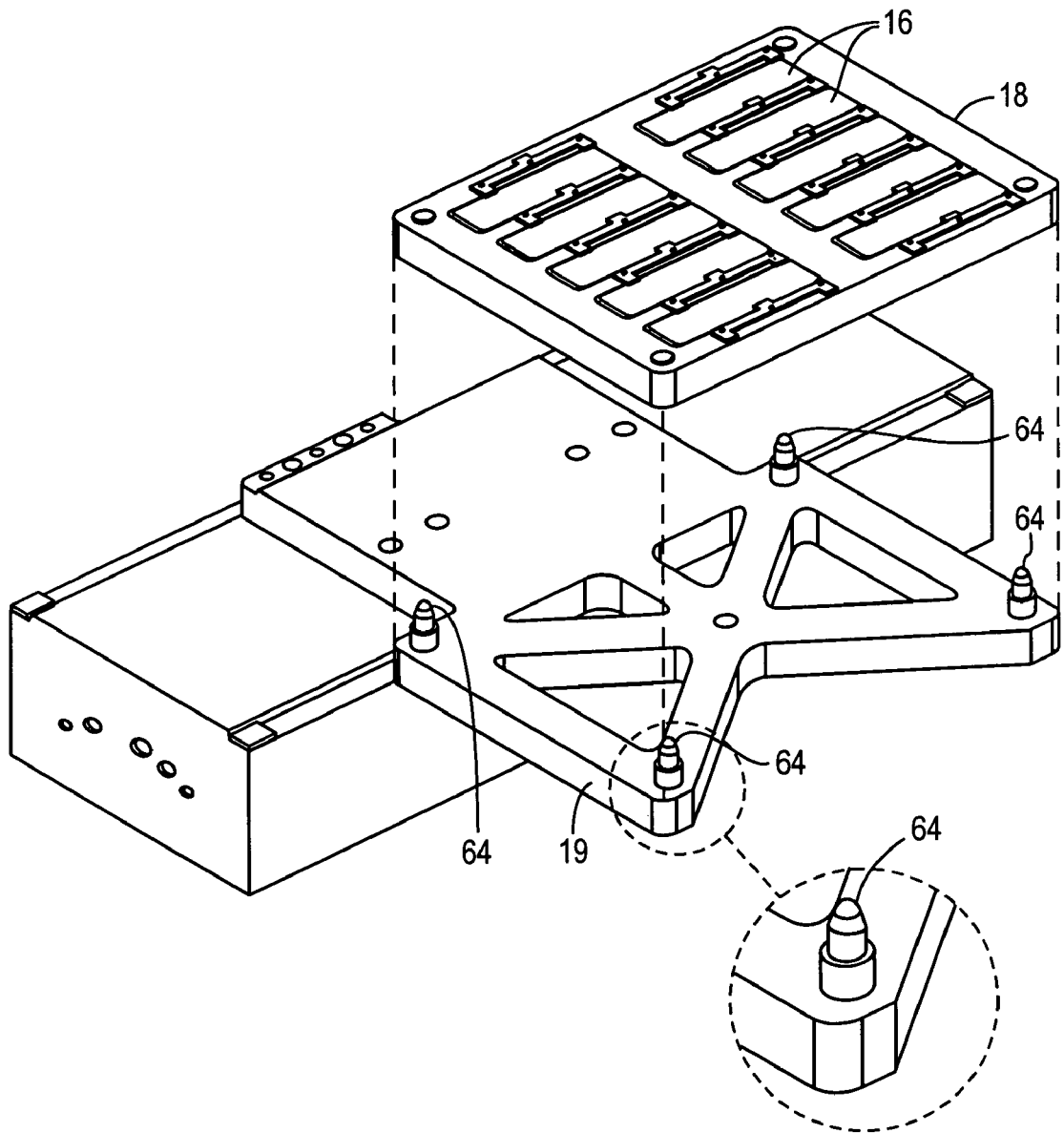
FIG. 6B is a schematic exploded perspective view of a substrate-holder support including datums for engaging reference surfaces disposed on a substrate-holder in accordance with one embodiment of the invention.
Figure 6C:
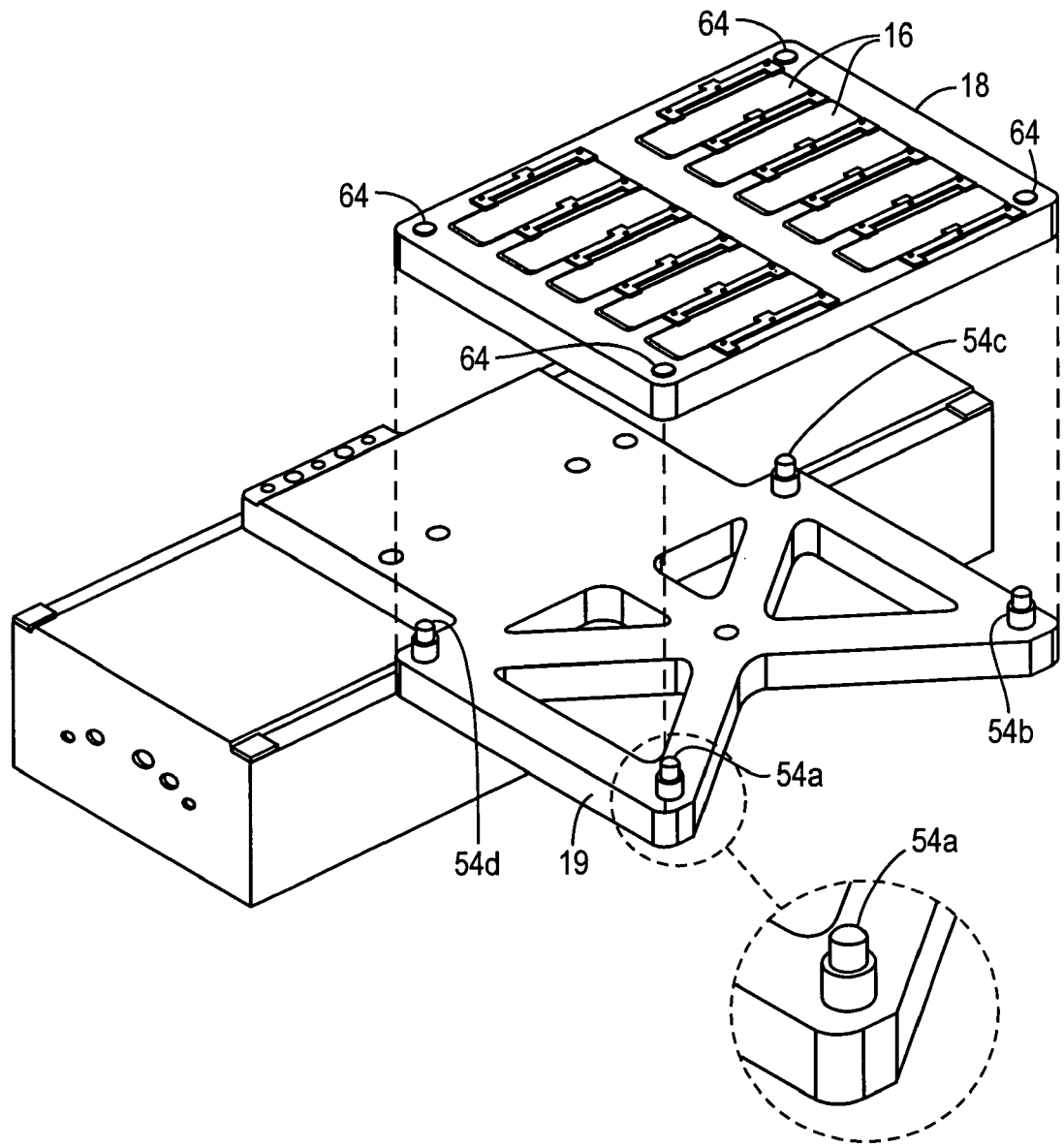
FIG. 6C is a schematic exploded perspective view of a substrate-holder support including inserts for engaging datums disposed on a substrate-holder in accordance with one embodiment of the invention.

With reference to FIGS. 5B and 6B, in another embodiment, reference surfaces are machined or formed on four hardened metal inserts 54a, 54b, 54c and 54d that are securely affixed in the corners of the substrate-holder 18. In one embodiment, the insert 54a includes a conically-shaped reference surface 55. Additional hardened metal inserts 54b and 54d in the two adjacent corners of the substrate-holder include V-groove reference surfaces 56, 57. The two V-groove reference surfaces 56, 57 are oriented with the axes of their grooves passing through the apex of the conical surface 55. The inserts 54b, 54d with V-groove reference surfaces are secured to the substrate-holder 18 via dowel pins 58 and adhesive. The insert 54c in the remaining corner of the substrate-holder 18 has a simple flat (horizontal) surface 60 and is secured to the substrate-holder 18 via a screw thread and adhesive.

With reference to FIG. 6B, the reference surfaces 55, 56, 57, and 60 on the inserts 54a, 54b, 54c, 54d that are secured into the substrate-holder 18 are designed to rest in contact with datums 64 disposed on the substrate-holder support 19. In the illustrated embodiment, the datums 64 include hemispherical surfaces and are disposed at four corners on the substrate-holder support 19.

As before, when the reference surfaces 55, 56, 57, 60 of the inserts 54a, 54b, 54c and 54d are received on the datums 64 of the substrate-holder support 19, the datums 64 and the reference surfaces 55, 56, 57, and 60 locate the substrate-holder 18 in a selected position in a selected plane. Further, if the substrate-holder 18 is removed from the substrate-holder support 19, and then re-seated on the substrate-holder support 19, the substrate-holder 18 will locate itself in the identical plane and in the identical position within the plane. In addition, any substrate-holder 18 with the reference surfaces 55, 56, 57, 60 set in the same positions and at the same heights (inserts 54a and 54c are adjustable for this purpose) will be accurately located in the same plane and in the same position within the plane with respect to the substrate-holder support 19.

Figure 5C:
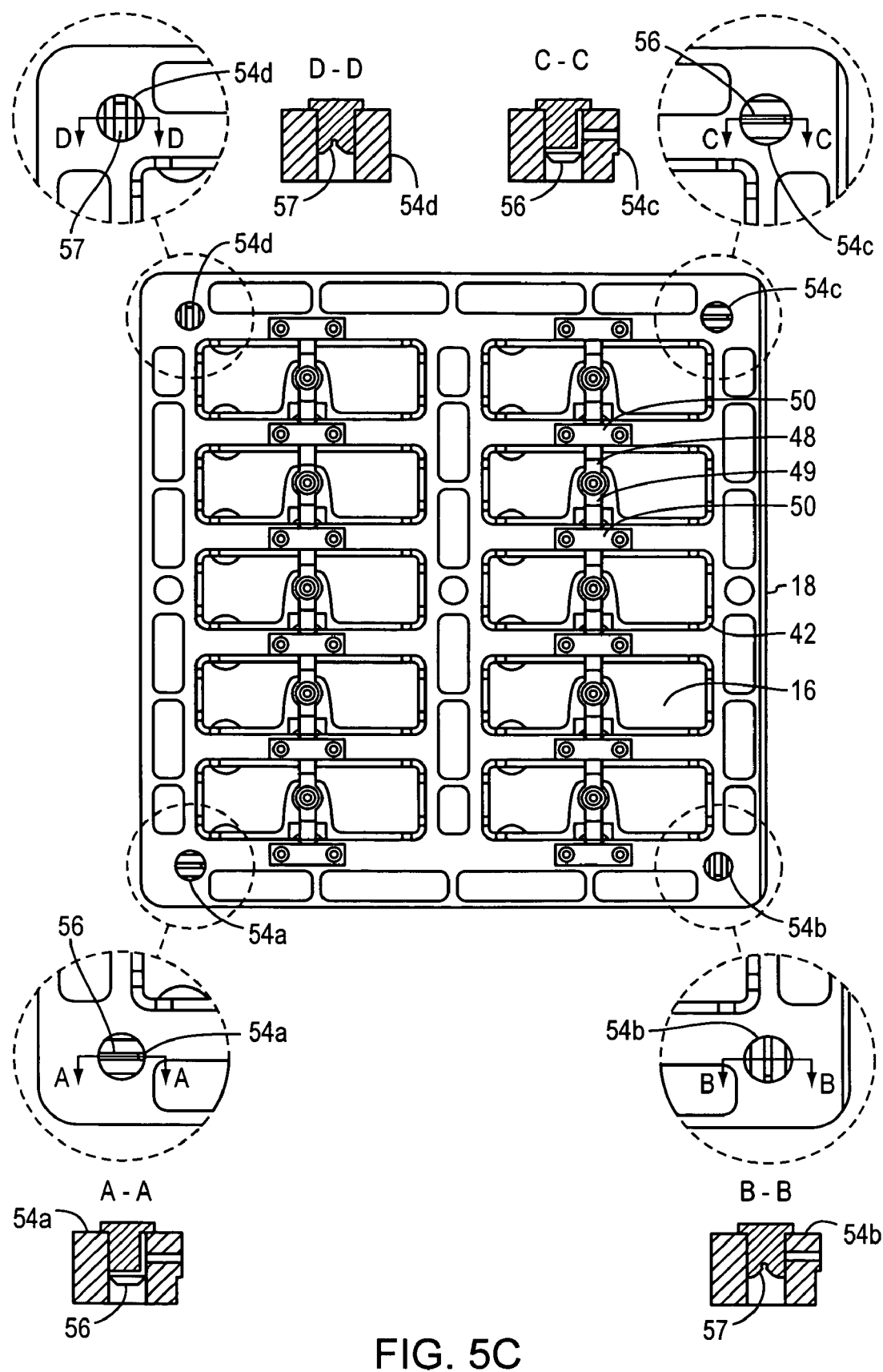
FIG. 5C is a schematic bottom view of a substrate-holder including inserts for mating with datums disposed on a substrate-holder support in accordance with one embodiment of the invention.
Figure 8:
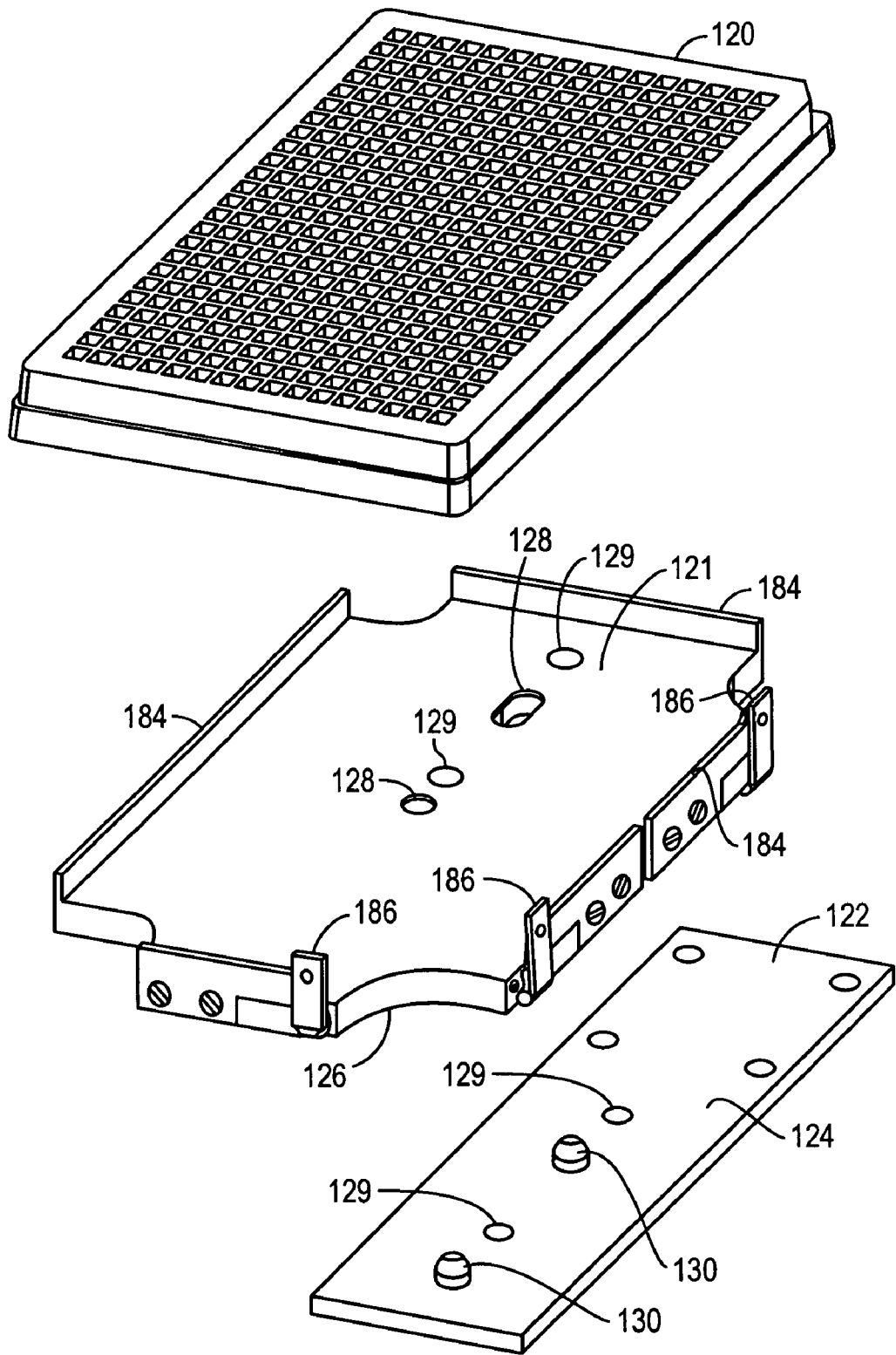
FIG. 8 is a schematic exploded perspective view of a fluid-reservoir holder including reference surfaces for engaging datums disposed on a fluid-reservoir holder support in accordance with one embodiment of the invention.

Other embodiments for providing accurate and repeatable positioning of the substrate-holder 18 on a substrate-holder support 19 are included within the scope of the present invention. Possible alternative embodiments include, but are not limited to:

a) Providing three or more recesses in the bottom surface of the substrate-holder 18 and an equal number of matching projections in the top surface of the substrate holder support 19. All recesses, when engaged with the matching projections on the substrate-holder 18, provide bearing surfaces to define the resting location of the substrate-holder 18 in the axis perpendicular to the top surface of the substrate-holder 18. If at least two of the recesses, when engaged in the matching projections on the substrate-holder support 19, also provide restraint to motion in the plane of the substrate-holder 18 (at a minimum two of the engaged elements must provide restraint to motion in two perpendicular axes parallel to the plane of the substrate-holder 18), the substrate-holder 18 will be firmly located in three dimensions.

b) The equivalent arrangement to a), wherein the recesses are disposed in the substrate-holder support 19 and the projections are disposed on the lower surface of the substrate-holder 18.

c) Providing precisely machined (e.g. milled or ground) bottom surface regions on the substrate-holder 18 designed to engage three or more support projections on the substrate-holder support 19 (this defines the plane of the substrate-holder 18 and defines its position in the z-axis). Fiducial surfaces are also provided on the substrate-holder support 19 to restrict motion in the x and y axes, and the substrate-holder 18 is urged by a spring, a magnet, a vacuum or other compliant or biasing means against these surfaces.

d) Providing a precisely-milled or ground flat bottom on the substrate-holder 18 designed to engage a precisely-milled or ground flat surface on the substrate-holder support 19 (this defines the plane of the substrate-holder and defines its position in the z-axis). Fiducial surfaces 72 are also provided on the substrate-holder support 19 to restrict motion in the x and y axes and the substrate-holder 18 is urged by a spring 73, a magnet, a vacuum or other compliant or biasing means against these surfaces (FIG. 5E).

e) Providing three or more bearing surfaces on the bottom of the substrate-holder support 19 designed to rest upon precisely-milled or ground flat surface regions on the substrate holder 18 (this defines the plane of the substrate-holder 18 and defines its position in the z-axis). Fiducial surfaces on the substrate-holder support 19 are also provided to restrict motion in the x and y axes and the substrate-holder 18 is urged by a spring, a magnet, a vacuum or other compliant or biasing means against these surfaces.

f) Providing three or more grooved (e.g. V-groove) recesses with parallel axes in the lower surface of the substrate holder 18 to engage with matching point supports on projections disposed on the substrate-holder support 19. A fiducial surface is also provided on the substrate-holder support 19, perpendicular to the axes of the grooves. The substrate-holder 18 is urged by a spring, a magnet, a vacuum or other compliant or biasing means against the fiducial surface.

g) The equivalent arrangement to f), wherein the recesses are in the substrate-holder support 19 and the projections are on the lower surface of the substrate holder 18.

h) Providing two or more elongated grooved (e.g. V-groove) recesses with parallel axes in the lower surface of the substrate holder 18 to engage with matching elongated supports (e.g. bar supports) projecting from the substrate holder support 19. A fiducial surface on the substrate-holder support 19 is also provided that is perpendicular to the axes of the grooves. The substrate holder 18 is urged by a spring, a magnet, a vacuum or other compliant or biasing means against the fiducial surface.

i) The equivalent arrangement to h), wherein the recesses are in the substrate-holder support 19 and the projections are on the lower surface of the substrate holder 18.

j) Any of the mechanisms described in b)-i) above, further including two or more through-holes in the substrate holder 18 that are designed to locate the substrate holder on matching conical projections on the substrate-holder support 19 (similar to the fluid-reservoir disposed on the fluid-reservoir support illustrated in FIG. 8).

k) The arrangement described in j) above, further including a compliant or biasing means (e.g. a spring, a magnet, an electromagnet, or a vacuum) to bias the substrate-holder 18 onto the side of one or more of the conical projections.

l) Providing two parallel V-grooves 71 and four spherically tipped precision adjustment screws or datums 64. A fiducial surface 72 is provided on the substrate-holder support 19 that is perpendicular to the axes of the grooves 71.

Figure 5D:
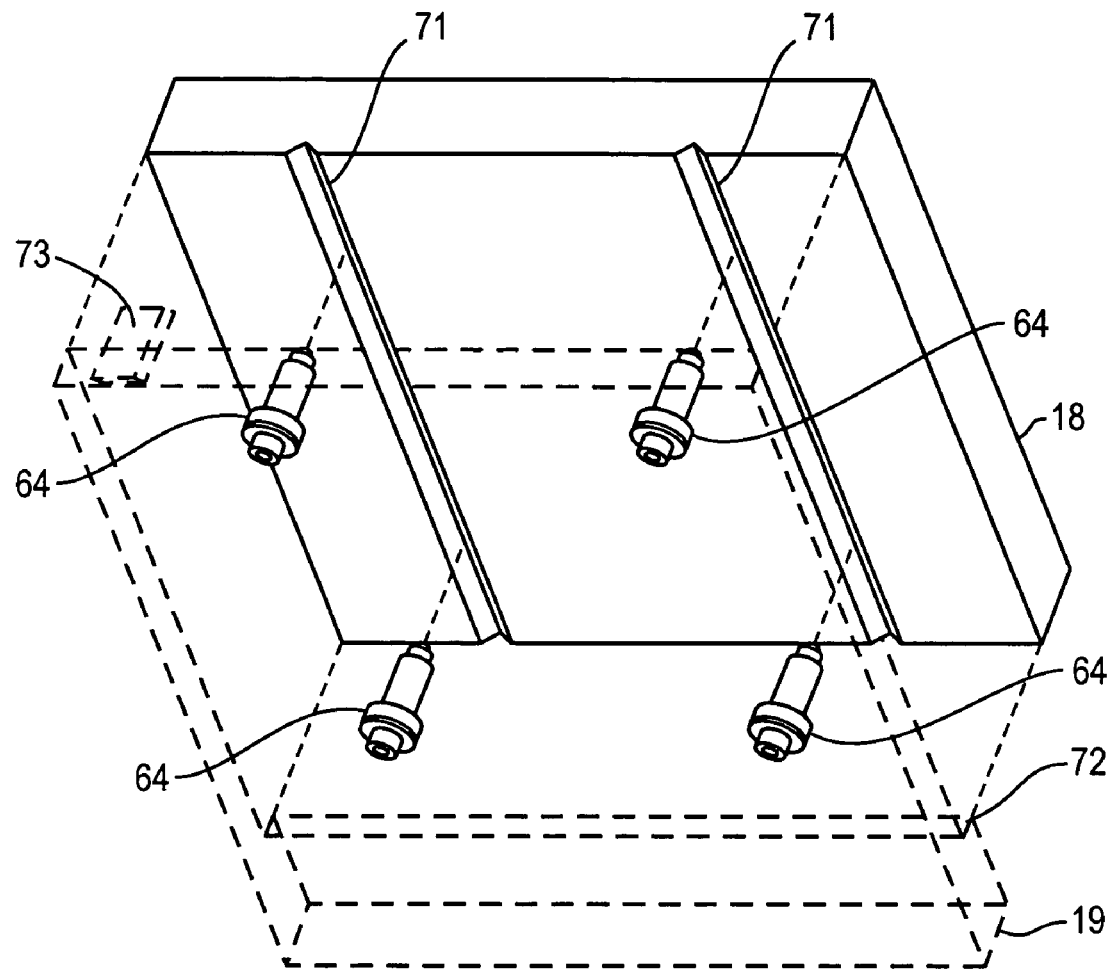
FIG. 5D is a schematic exploded perspective view of a substrate-holder including parallel grooves for mating with precision adjustment screws disposed on a substrate-holder support in accordance with one embodiment of the invention.
Figure 5E:
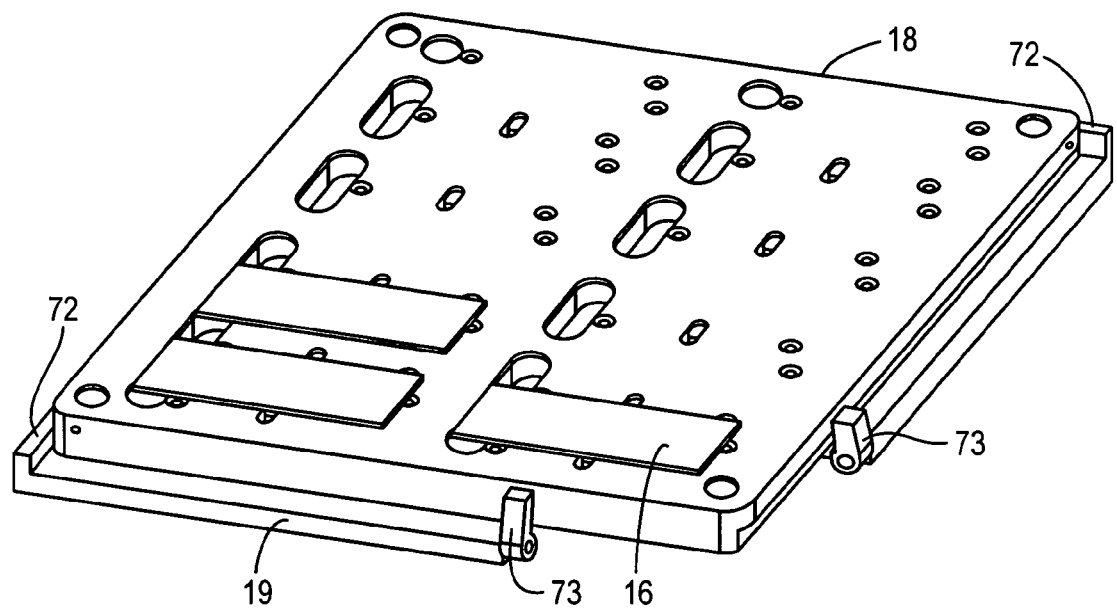
FIG. 5E is a schematic perspective view of a substrate-holder support structure in accordance with one embodiment of the invention.

The substrate-holder 18 is urged by a spring 73, a magnet, a vacuum or other compliant or biasing means against the fiducial surface 72 (FIG. 5D).

m) Providing a substrate-holder 18 with inserts 54a, 54b, 54c and 54d having opposed pairs of V-grooves for mating with datums 64 (for example, spherical or conical) disposed on the substrate-holder support 19 (FIG. 5C).

Referring again to FIG. 1, in another embodiment, the use of substrate-holders 18 that can be repeatably and accurately loaded onto a substrate-holder support 89 is combined with a substrate-holder storage 70 for temporally storing a multiplicity of substrate-holders 18 and the substrates 16 located thereon. A conveyor system (not shown) for removing substrate-holders 18 from the substrate-holder storage 70, loading the substrate-holders 18 onto the substrate-holder supports 89 for deposition of fluids on the substrates 16, and then returning the substrate-holders 18 to the substrate-holder storage 70 may also be included. Alternatively, the motion system on which the substrate-holder support 89 is disposed may directly access the substrate-holder storage 70 to remove a substrate-holder 18 from the substrate-holder storage 70 or to place a substrate-holder 18 therein.

Various components of the microarrayer assembly 10 described above may be combined together in alternative embodiments in accordance with the invention. When combined, various benefits may be achieved.

For instance, in one embodiment, substrate-holders 18 may be readily loaded into, and removed from, the deposition area (the area generally beneath the printheads) of the microarrayer assembly 10 without loss of positional accuracy. In other words, all properly calibrated substrate-holders 18, when mounted on the substrate-holder support 89, will position the top surfaces 17 of the substrates 16 in a substantially identical plane, as well as in a substantially identical position in the plane.

In another embodiment, the number of substrates 16 that may be processed by the microarrayer assembly 10 is limited only by the number of substrates 16 on each substrate-holder 18 and the available number of substrate-holders 18 in the substrate-holder storage 70. This benefit is derived in embodiments where the microarrayer can autonomously access the substrate-holder storage 70.

In another embodiment, the substrate-holders 18 may be removed from, and added to, the substrate-holder storage 70 while depositions are underway on an active substrate-holder 18 loaded in the deposition area of the microarrayer assembly 10. Therefore, it is not necessary to cease spotting operations to load and unload substrates 16 or substrate-holders 18, as in existing microarrayers. It will be appreciated that deposition operations may continue indefinitely if, periodically, fresh substrates 16 are introduced into the substrate-holder storage 70 and processed substrates 16 are removed from the storage 70.

In another embodiment where the number of substrates 16 that can be processed is limited only by the capacity of the substrate-holder storage 70 and not the size of the substrate-holder 18, relatively small substrate-holders 18, holding, for example six to twenty glass-slide substrates 16 may be used, minimizing the size of the deposition area and volume of the microarrayer assembly 10. Moreover, the use of small substrate-holders 18 may negate the need for large, slow, overly complex and expensive motion elements that are required for larger mobile substrate-holders 18.

In yet another embodiment including a substrate-holder storage 70, manual loading/unloading of substrates 16 from the section of the microarrayer 10 dedicated to deposition is eliminated. Automatic loading and unloading of substrates 16 minimizes or eliminates sources of error resulting from frequent human access to the deposition area.

In another embodiment that includes automatic loading of substrates 16 into the microarrayer assembly 10, the area for droplet depositions (the deposition chamber) is relatively closed and relatively undisturbed by human access. Therefore, well-controlled and stable environmental conditioning of this area is possible. In another embodiment, separate environmental controls may be applied to the substrate-holder storage 70 and the deposition area.

In yet another embodiment where relatively small substrate-holders 18 are used, the exposure of the substrates 16 to the environment of the deposition area can be relatively short. This may be of benefit, for example, if the fluids being deposited are best kept cold, but may be at a higher temperature for deposition. In yet another embodiment, the microarrayer assembly 10 may be scaled in size, since the size and functions of the deposition equipment is not tied to the number of substrates 16 being processed. Therefore, as later described, arrayer designs can be realized using multiple deposition engines working cooperatively to significantly increase throughput.

c) Fluid Reservoirs and Fluid Reservoir Holders

A variety of fluid reservoirs 20 may be used to supply the fluid samples to the printheads 12 of the microarrayer assembly 10. In one embodiment, a microplate 20 with 96 wells, or a multiple of 96 wells is used. The use of the higher density microplates 20, for example, having 1536 wells, is suited to solid-pin deposit element 14 implementations since very narrow pin tips 26 are readily fabricated with solid pins 14.

Figure 7:
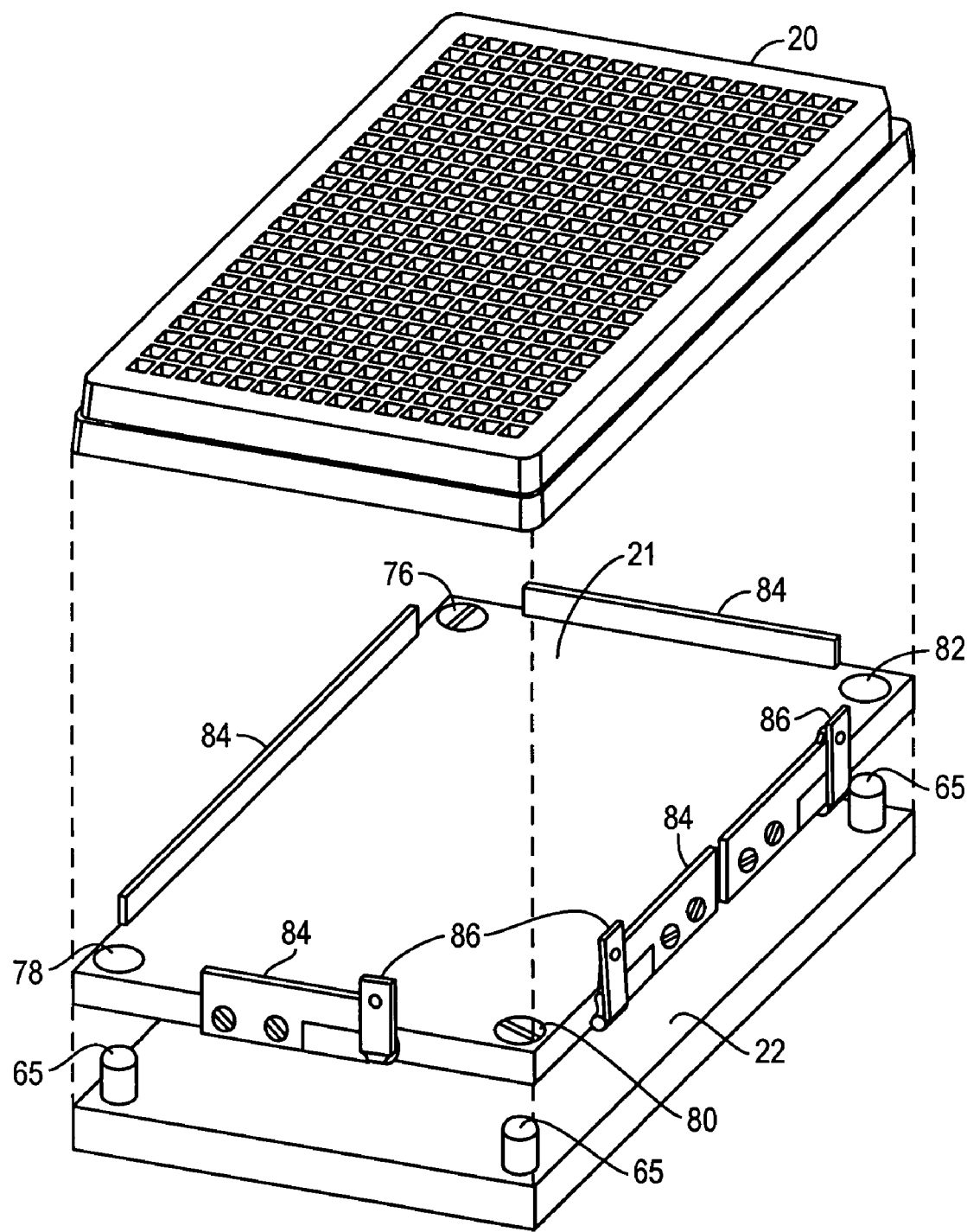
FIG. 7 is a schematic exploded perspective view of a fluid-reservoir holder including inserts for engaging datums disposed on a fluid-reservoir holder support in accordance with one embodiment of the invention.

In microarrayer assembly 10 embodiments that include a high density fluid-reservoir array, such as microplates 20 with 1536, 3456 or 6144 wells, greater positional accuracy is required to hold the fluid reservoir 20 in the microarrayer assembly 10. With reference to FIG. 7, a fluid-reservoir holder 21 that includes inserts 76, 78, 80, and 82 designed to engage datums 65 disposed on a fluid-reservoir holder support 22 is illustrated. Similar to the mounting arrangement for the substrate-holder 18 and the substrate-holder support 19 described earlier in FIGS. 5B and 6B, the inserts and the datums respectively disposed on the fluid reservoir holder 21 and the fluid reservoir holder support 22 enable fluid-reservoirs 20 to be accurately and repeatably loaded onto into the microarrayer assembly 10. In another embodiment, three inserts are provided to engage three datums as described with reference to FIGS. 5A and 5B. In other embodiments, any of the referencing or planarization systems described previously for use with the substrate-holder 18 and the substrate-holder support 19 can be used with either a fluid reservoir 20 mounted directly onto a fluid-reservoir holder support 22 or a fluid reservoir holder 21 mounted on a fluid reservoir-holder support 22, the fluid-reservoir holder holding the fluid-reservoir 20. In addition, a fluid-reservoir holder storage 83 may be included in the microarrayer assembly 10. Similar to the substrate handling mechanisms described earlier, the fluid reservoirs holders 21 may be robotically removed from the fluid-reservoir holder storage 83 and placed back into the storage 83 after use. This provides many of the same advantages described earlier with respect to the automated handling of substrates.

With continued reference to FIG. 7, the fluid reservoir 20 is referenced against precisely machined raised edges 84 disposed on the fluid-reservoir holder 21. Resilient spring clips 86 are then used to hold the fluid reservoir 20 firmly against the raised reference edges 84 of the fluid-reservoir holder 21.

In one embodiment, overall fluid-reservoir holder and fluid-reservoir holder support system position accuracy is within ±0.02" in the x, y, and z-axes. In a preferred embodiment, overall fluid-reservoir holder and fluid-reservoir holder support system position accuracy is within ±0.002" in the z-axis and within ±0.01" in the x and y axes. In a more preferred embodiment, overall fluid-reservoir holder and fluid-reservoir holder support system position accuracy is within ±0.0002" in the z-axis and within ±0.001" in the x and y axes.

With reference to FIG. 8, an alternative embodiment of a fluid-reservoir holder 121 is illustrated. The fluid-reservoir holder support 122 includes a precisely fabricated flat top surface 124 designed to interface with a precisely fabricated flat undersurface 126 of the fluid-reservoir holder 121. Precisely machined through holes 128 in the fluid-reservoir holder 121 are configured to accept reference pins or datums 130 with conical surface segments. The fluid-reservoir 20, when installed, is referenced against raised edges 184 disposed on the fluid-reservoir holder 121. Resilient spring clips 186 may be used to hold the fluid-reservoir 120 firmly against the raised reference edges 184. Two pairs of magnetic elements 129, one disposed on the lower surface of the fluid-reservoir holder 121 and one disposed on the fluid-reservoir holder support 122 provide a pre-load to hold the lower surface of the fluid-reservoir holder 121 firmly against the fluid-reservoir holder support 122 and also to bias the side of the holes 128 against the vertical elements of the reference pins 130 to constrain any motion in the horizontal plane.

In some embodiments, especially when using fluid-reservoirs 20 that include a dense array of wells, it is desirable to place lids on the fluid-reservoirs 20 when they are not in use to minimize evaporation of the fluid and the introduction of airborne contaminants or particulates into the fluid. In such cases an automated de-lidding station can be added to the microarrayer assembly 10 to remove the lid before the fluid-reservoir 20 is used to supply fluids to the deposit elements 14, and to replace the lid after the completion of use of the fluid-reservoir 20.

d) Microarrayer Architectures

The deposition of micro fluid droplets in ordered arrays upon substrates 16 requires a minimum set of physical motions to bring the printhead 12 into proximity with all fluid retention locations of the fluid reservoir 20 and all deposition sites on the substrate 16. Precision linear or rotational motion systems that are computer controlled and, in some instances, have precision positional feedback, are assumed to be included in the following embodiments. The physical, electrical and computer program elements required to realize such precision motion control, with positioning capability in the micron or sub-micron range, are well known to those skilled in the art, and are therefore not described further.

In various embodiments, any of the assemblies described may be configured with covers, heaters, chillers, humidifiers, dehumidifiers, control systems and other elements to provide a controlled environment in which the fluid droplets are deposited upon the substrates 16. In some cases, it may be preferable to provide temperature control to the entire microarrayer assembly 10, and in some cases individual elements of the microarrayer assembly 10 may be controlled e.g. localized cooling of the fluid reservoir 20 to inhibit denaturing of sensitive biological samples. Air filtering to inhibit contamination of the fluid samples or the substrates 16 by airborne particulates can also be provided. Similarly, the substrate-holder storage 70 and the fluid-reservoir holder storage 83 can be similarly environmentally conditioned, with the same, or with different environmental parameters.

i) Microarrayer Architectures for "Equal Exposure Time" Spotting

In various embodiments, the motion control system, in addition to controlling the relative positions of the substrate-holders 19 and the fluid-reservoir holders 21, is designed and arranged to:

i) move the printhead 12 and/or the fluid reservoir 20, relatively, to dip the deposit elements 14 into the fluid reservoir 20 to capture fluid;

ii) move the printhead 12 and/or the substrate 16, relatively, to position the desired fluid deposition location on the substrate 16 under the printhead 12;

iii) move the printhead 12 and/or the substrate 16, relatively, so that the deposit element 14, or the fluid droplet on the tip of the deposit element 14, contacts the top surface 17 of the substrate 16; and, iv) vary the speed of motion of the various moving elements, or equivalently, introduce variable delays in the motions, calculated and applied such that for every deposited droplet of fluid on the substrate 16 or substrates 16, the fluid captured by the deposition element 14 is exposed to the surrounding atmosphere for substantially the same amount of time between its extraction from the fluid reservoir 20 and its deposition on the substrate 16 nomatter from which part of the fluid reservoir 20 the fluid is extracted, nor where on the substrate 16, or on which substrate 16 the fluid droplet is deposited.

Figure 9:
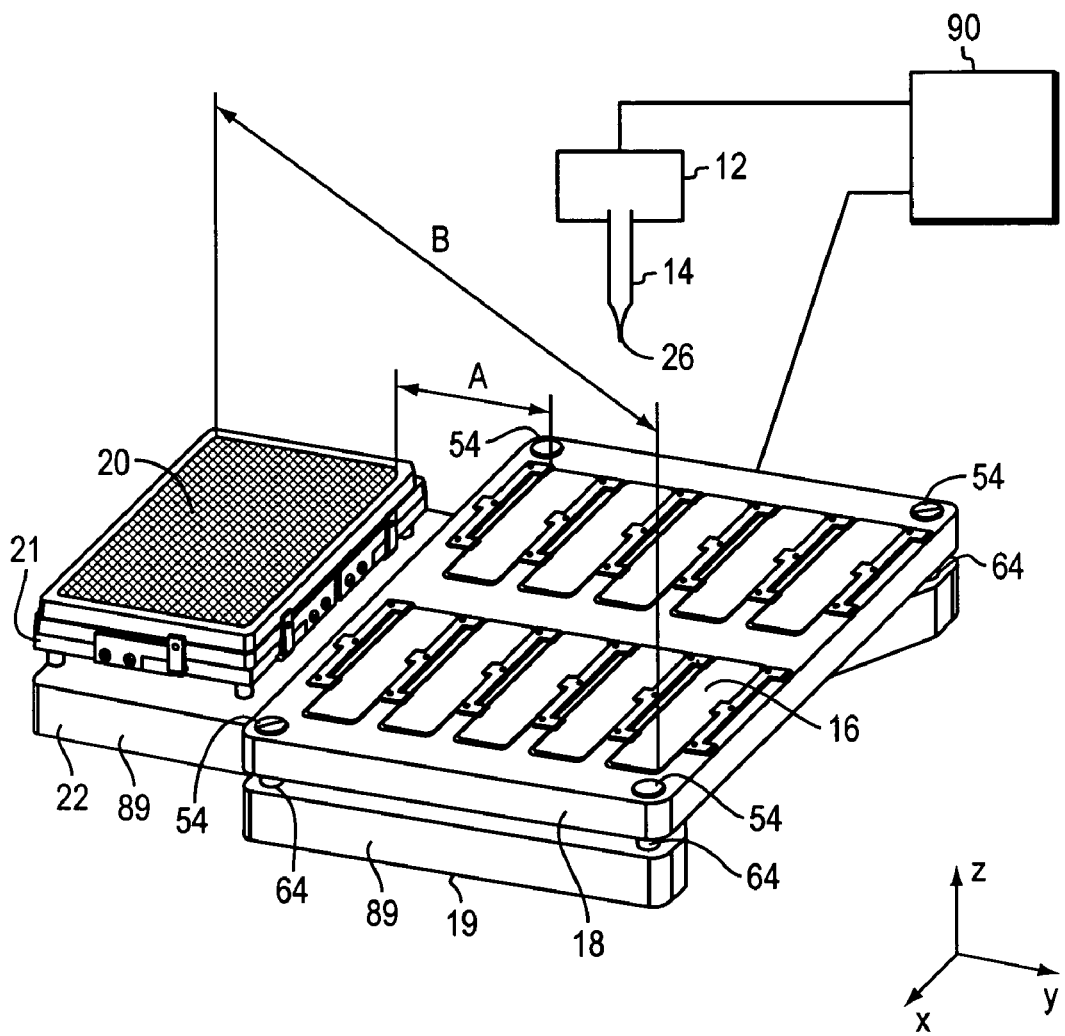
FIG. 9 is a schematic perspective view of a microarrayer architecture in accordance with one embodiment of the invention.

The use of the motion control system in this manner equalizes the evaporation of the fluid being carried by the deposit element 14 during the time period between fluid capture from any fluid reservoir 20 location, to deposition on any droplet deposition site on the substrate 16. The arrangement is conceptually illustrated in FIG. 9. Referring to FIG. 9, substrates 16 are secured to the substrate-holder 18 and a fluid reservoir 20 is secured to a fluid reservoir holder 21. The substrate-holder 18 includes one of the planarization systems earlier described to accurately and repeatably load the substrate-holder 18 on datums 64 disposed on the substrate-holder support 19. Likewise, the fluid reservoir holder 21 which holds the fluid reservoir 20 includes one of the planarization systems earlier described to accurately and repeatably load the fluid-reservoir holder 21 on datums 65 disposed on the fluid-reservoir-holder support 22. In the illustrated embodiment, the substrate-holder support 19 and the fluid reservoir holder support 22 are a single, integrally formed, platen 89. For illustration purposes, a single deposit element 14 is held by a printhead 12, however, the printhead 12 may hold a plurality of deposit elements 14. Fluid is captured from the fluid-reservoir 20 by dipping the tip 26 of the deposit element 14 into the wells. Fluid is then spotted on the substrate 16 by touching the tip 26 of the deposit element 14, or the fluid droplet on the tip of the deposit element 14, onto the desired position of the substrate 16. A motion control system, for instance, a computer 90, provides stimuli to actuators to move the platen 89 and the printhead 12, such that the time of exposure of the fluid droplet on the tip 26 of the deposit element 14 to the air is the same for the shortest path and the longest path between a well and a deposition location, and all paths in between. In FIG. 9, the shortest path is represented by path "A" and the longest path is represented by path "B". Equalization of the exposure times as described may be realized by extending the exposure times for all depositions to match the longest exposure time, for example, the time taken for the deposit element 14 and the platen 89 to move relatively over path "B". The longest exposure time may be calculated based on the motion parameters of the mobile elements involved, or by measurement of the exposure time associated with the longest path length involved, i.e. path "B", at the maximum operating acceleration, maximum velocity, and maximum deceleration. The extension of the exposure times for paths shorter than path B, (for instance, path A), may be applied as delays between the various motions (e.g. delay in lowering the printhead 12 to deposit the droplet on the substrate 16 or by slowing the speed of one or more of the printhead 12 and the platen 89).

ii) Microarrayer Architectures with Combined Substrate Motion and Fluid Reservoir Motion Referring again to FIG. 1, one embodiment of an architecture for the microarrayer assembly 10 is further described. In the illustrated embodiment, the substrate-holder 18 and the fluid-reservoir holder 21 are shown mounted on the shared platen 89 which is movable in an X-Y plane when disposed beneath the printhead 12. The shared platen 89 may be operated to access both the substrate-holder storage 70 and the fluid reservoir holder storage 83. The substrate-holder storage or "hotel" 70 includes a vertically mobile rack of vertically-separated receptacle spaces into which substrate-holders 18, along with the substrates 16 mounted thereon, may be initially manually or automatically installed. Each substrate-holder 18 is supported in the substrate-holder storage 70 by rails 92 which extend slightly under the substrate-holder 18 on opposite sides. Each receptacle is spaced apart, or can be moved apart, by a distance that will permit access between the receptacle spaces by the platen 89 of the microarrayer assembly 10. In one embodiment, substrate-holders 18 are transferred to the platen 89 of the microarrayer assembly 10 by:

a) vertically moving the rack of substrate-holders 18 in the substrate-holder storage 70 to position a space below the substrate-holder 18 to be removed in the plane of motion of the platen 89. The space must be large enough for entry of the platen 89, b) moving the platen 89 beneath the substrate-holder 18 to be transferred, c) vertically moving the substrate-holders 18 in the substrate-holder storage 70 to lower the desired substrate-holder 18 onto the platen 89 such that the inserts 54 of the substrate-holder 18 contact and engage the datums 64 on the platen 89 to accurately position the substrate-holder 18 on the platen 89 in a defined plane as earlier described. At this time, the substrate-holder 18 is no longer supported by the rails 92, and d) moving the platen 89 in the y dimension to withdraw the substrate-holder 18 from the substrate-holder storage 70.

Figure 10:
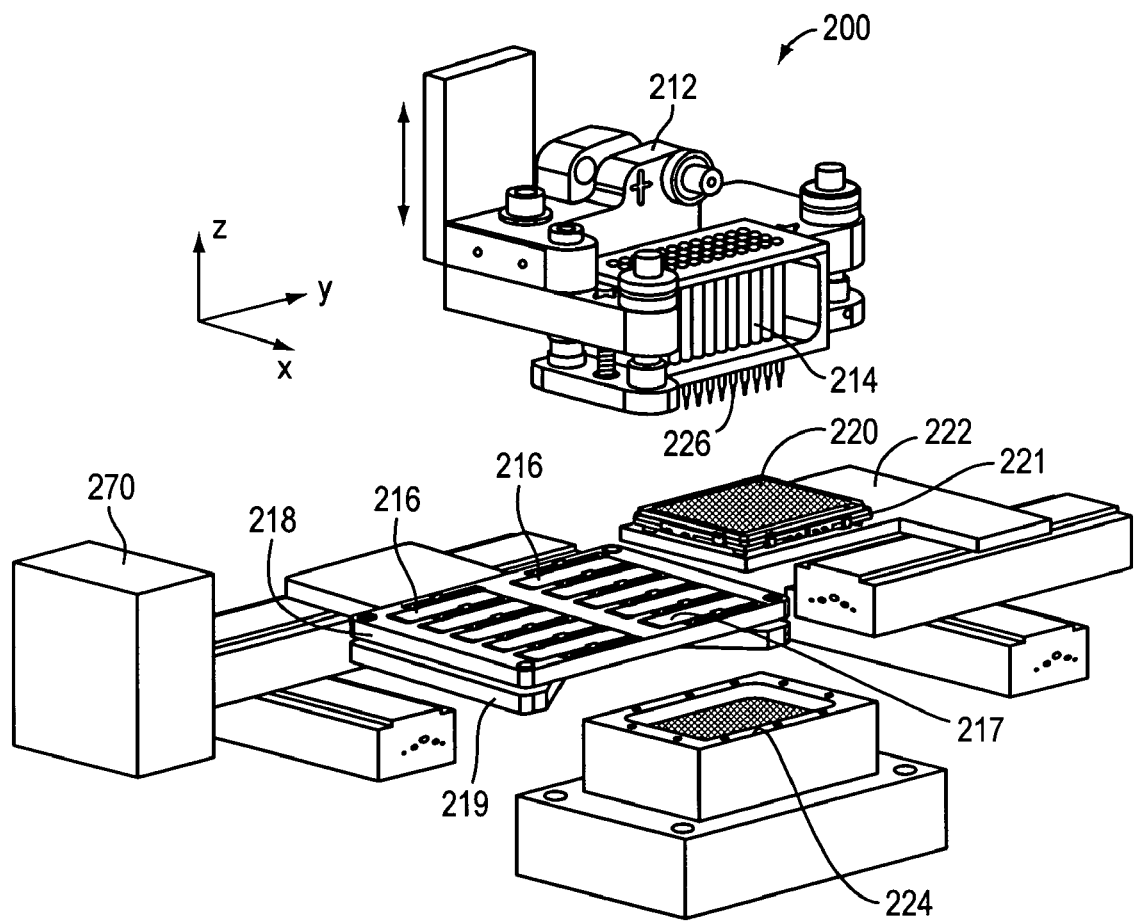
FIG. 10 is a schematic perspective view of a microarrayer architecture in accordance with one embodiment of the invention.

Returning a substrate-holder 18 to the substrate-holder storage 70 may be effected by the same series of steps in reverse. An equivalent set of steps may be used to load and unload fluid-reservoir holders 21 from the fluid-reservoir holder storage 83.

iii) Microarrayer Architectures with Separate Substrate Motion and Fluid Reservoir Motion With reference to FIG. 10, another embodiment of a microarrayer assembly 200 is illustrated. In this embodiment, the motion of a printhead 212 including one or more deposit elements 214 is coordinated with the motions of a substrate-holder support 219 and a fluid reservoir holder support 222 which are actuatable in separate X-Y planes. The substrate-holder support 219 and the fluid reservoir holder support 222 are independently mobile, but move in a coordinated manner to effect the deposition of fluid droplets upon substrates 216. The substrate-holder 218 and the fluid reservoir holder 221 are respectively held on the substrate-holder support 219 and on the fluid reservoir holder support 222 using the planar referencing systems described earlier. In another embodiment, a fluid reservoir 220 is directly positioned on the fluid reservoir holder support 222 using the planar referencing systems described earlier without the use of a holder 221.

With continued reference to FIG. 10, the fluid-reservoir holder support 222, in one embodiment, may:

a) move such that any desired location of the fluid reservoir 220 is positioned directly below the deposit elements 214 of the print head 212 to allow charging or re-charging of those deposit elements 214 by having the deposit elements 214 dip into the fluids held in the fluid reservoir 220.

b) move clear of the vertical path of the print head 212 assembly to allow the print head 212 to descend below the X-Y plane in which the fluid reservoir 220 moves when disposed beneath the printhead to i) deposit droplets of fluid onto the substrates 216 or ii) access a wash station 224, which is vertically below the printhead 212.

c) move clear of the vertical path of the printhead 212 into an area in which the fluid-reservoir holder 221 can be accessed for manual or robotic replacement of the fluid-reservoir holder 221, for example, to a storage 270.

Similarly, the substrate-holder support 219 may move in a plane displaced from the plane of motion of the fluid-reservoir holder support 222 to:

a) position the substrates 216 such that any desired respective set of printing locations on any substrate 216 is directly below the deposit elements 214 of the printhead 212 to allow deposition of a fluid sample, or fluid samples, on the substrate 216 when the printhead 212 is lowered such that the tip 226 of each deposit elements 214 is in contact with, or the droplet of fluid on the tip 226 of each deposit elements 214 is in contact with, the top surface 217 of the substrate 216, b) move clear of the vertical path of the printhead 212 to enable the printhead 212 to descend unobstructed below the x-y plane in which the substrate-holder support 219 moves when it is disposed beneath the printhead 212 to access components or equipment below such as the wash station 224, and c) move clear of the path of the printhead 212 into an area from which the substrate-holder 218 may be accessed for its manual or robotic removal or replacement for the purpose of removal or replacement of the substrates 216, for example, to the storage 270.

d) Position sensing (e.g. using position encoders) allows automated monitoring of the location of the substrate-holder support 219, the fluid-reservoir holder support 222, and the printhead 212. Computer control inhibits any motions of these components that would result in unintentional contact between them.

Deposition of droplets of biological or chemical liquid material upon the substrates 216 may be achieved in one embodiment by: (note: this procedure assumes that the deposit elements 214 for example, solid pins 214, are clean and that the fluid reservoir(s) 220 and the substrates 216 are already supported on the fluid reservoir holder support 222 and the substrate-holder support 219 respectively)

a) moving the printhead 212 to a fully raised position in a Z-axis, b) moving the fluid-reservoir holder support 222 in an X-Y plane to align a first set of wells of the fluid-reservoir 220 under the deposit elements 214 of the printhead 212 while simultaneously moving the substrate-holder support 219 in tandem with the fluid-reservoir holder support 222 such that the absolute distance between the fluid-reservoir 220 and the substrates 216 remains substantially constant, c) moving (lowering) the printhead 212 in the Z-axis such that the tips 226 of the deposit elements 214 are immersed in the fluid samples and small amounts of fluid are captured on the tips of the deposit elements 214 when the deposit elements 214 are subsequently lifted out of the liquid samples, d) moving (raising) the printhead 212 away from the fluid-reservoir 220 a sufficient distance that the fluid-reservoir 220 can be moved in its X-Y plane without contacting the deposit elements 214 or any part of the printhead 212, e) moving the fluid-reservoir 220, in its X-Y plane, away from the vertical path of the printhead 212 towards its starting position to allow the printhead 212 to descend below the X-Y plane of the fluid-reservoir 220, f) moving the substrate-holder support 219 to align a first set of desired print locations on one substrate 216 under the printhead 212, g) lowering the printhead 212 in the Z-axis such that the tip 226 of each deposit element 214 is in contact with, or the droplet of fluid on the tip 226 of each deposit element 220 is in contact with, the top surface 217 of the substrate 216, thereby depositing small droplets of fluid (one droplet per pin) onto the top surface 217 of the substrate 216, h) raising the printhead 212 above the X-Y planes of both the fluid-reservoir-holder support 222 and the substrate-holder support 219 such that either can move in their respective planes without contacting the deposit elements 214 or any part of the printhead 212, i) moving the substrate-holder support 219 away from the vertical path of the printhead 212, j) repeating steps b) to i) for the next set of desired deposition sites on the same substrate 216 using the first set of wells on the fluid-reservoirs 220 until all desired deposition sites on that substrate 216 have been spotted with the fluid from that set of wells (note: users may wish to spot the same sample several times on a substrate 216 so that they can assess repeatability), k) repeating steps b) to i) for desired deposition sites on the second substrate 216 and on all other desired substrates 216 on the substrate-holder 218 using the same set of wells until all desired deposition sites on all substrates 216 have been spotted with the fluid from the first set of wells of the fluid reservoir 220, l) once all desired deposition sites on all substrates 216 on the substrate-holder 218 have been spotted with the fluid samples from the first set of wells on the fluid-reservoir 220, moving both the fluid-reservoir holder support 222 and the substrate-holder support 219 aside in their respective X-Y planes to allow the printhead 212 to descend to a wash station 224 where the deposit elements 214 are washed and dried to avoid carryover of fluid samples to the next set of printed spots, and m) repeating sequence a) through l), but now for the next set of fluid samples (i.e. the next set of wells in the fluid-reservoir 220) and then for all sets of fluid samples until all desired samples (perhaps from multiple fluid-reservoirs 220) have been spotted on all desired deposition sites on all substrates 216.

In another embodiment, it may be desirable to add wash-and-dry cycles to the spotting sequence described above, after a certain number of droplets have been deposited to avoid evaporative sample build-up on the deposit elements 214. These intermediate wash-and-dry cycles have been ignored in the above description to avoid complicating the narration of the deposition procedure.

In FIG. 10, the fluid reservoir holder support 222 moves, when disposed beneath the printhead 212, in an x-y plane above the x-y plane of motion of the substrate-holder support 219. In another embodiment, the substrate-holder support 219 may move in a plane of motion that is above the plane of motion of the fluid-reservoir holder support 222. In this arrangement, the fluid-reservoir holder support 222 may be held stationary beneath the printhead 212 throughout the printing cycle for a given set of wells of the fluid-reservoir 220.

In one embodiment, the procedure to deposit fluid on a substrate 216 using the alternative setup just described is as follows. As a first step, the desired first set of wells of the fluid-reservoir 220 are positioned below the deposit elements 214 of the printhead 212. The tips 226 of the deposit elements 214 are then immersed in the fluid samples by lowering the printhead 212. As a further step, the printhead 212 is raised before the substrate-holder support 219 travels to position a desired set of print locations below the printhead 212. The printhead 212 is then lowered to deposit fluid on the substrate 216 and then raised before the substrate-holder support 219 is moved away from the vertical path of the printhead 212. In the next step, the printhead 212 is lowered again into the same wells of the fluid-reservoir 220. This process is continued until all desired deposition locations have been spotted from the first set of wells on the fluid-reservoir 220. After moving the substrate-holder support 219 and fluid-reservoir holder support 222 aside to wash the deposit elements 214, a new set of wells are located under the deposit elements 214 of the printhead 212. This process is repeated until all desired fluid samples have been deposited at all desired locations on all desired substrates 216.

In other embodiments, it will be appreciated that a storage 270 and a means for transferring the substrate-holders 218 and the fluid-reservoir holders 221 between the storage 270 and the substrate-holder support 219 and the fluid-reservoir holder support 222 may be provided. The transfer of substrate-holders 219 and fluid-reservoir holders 221 to and from the storage 270 and their respective mobile supports 219, 222 can be implemented in the same manner earlier described.

The various architectures described may be used with solid pins 214 since the architectures can be used to minimize the cycle time for the continuous dip-and-deposit cycle that is required when using solid pins 214. Furthermore, in the described architectures, since the deposit elements 214 make the same vertical motion cycle for every deposition (i.e. the vertical path of the tip 226 of any deposit element 214 is the same for any deposition), the architectures are suitable for spotting fluids using the "equal exposure time" method with relatively little impact on overall deposition rates. Moreover, since the printhead 212 does not move laterally, there is no differential drying effect on one side of the pin 214 as would be experienced from "windage" effects in embodiments where the printhead is moved in an X-Y plane. Differential drying on one side of the pin 214 can affect the shape of the deposited droplet. Using the architectures described, drying of the sample on the pin 214 will occur uniformly around the pin 214 since the printhead 212 is only moved vertically.

iv) Microarrayer Architectures with a Plurality of Printheads

The separation of planar motions of the substrates holder support and the fluid reservoir support, combined with motion of the printhead in an axis perpendicular to the supports, permits further architectures to be developed that significantly increase deposition rates. The resulting architectures are particularly beneficial for increasing the deposition rates that may be achieved using solid pins. However, other deposition elements such as quill pins, pens and ink jet devices can also be effectively used.

Figure 11:
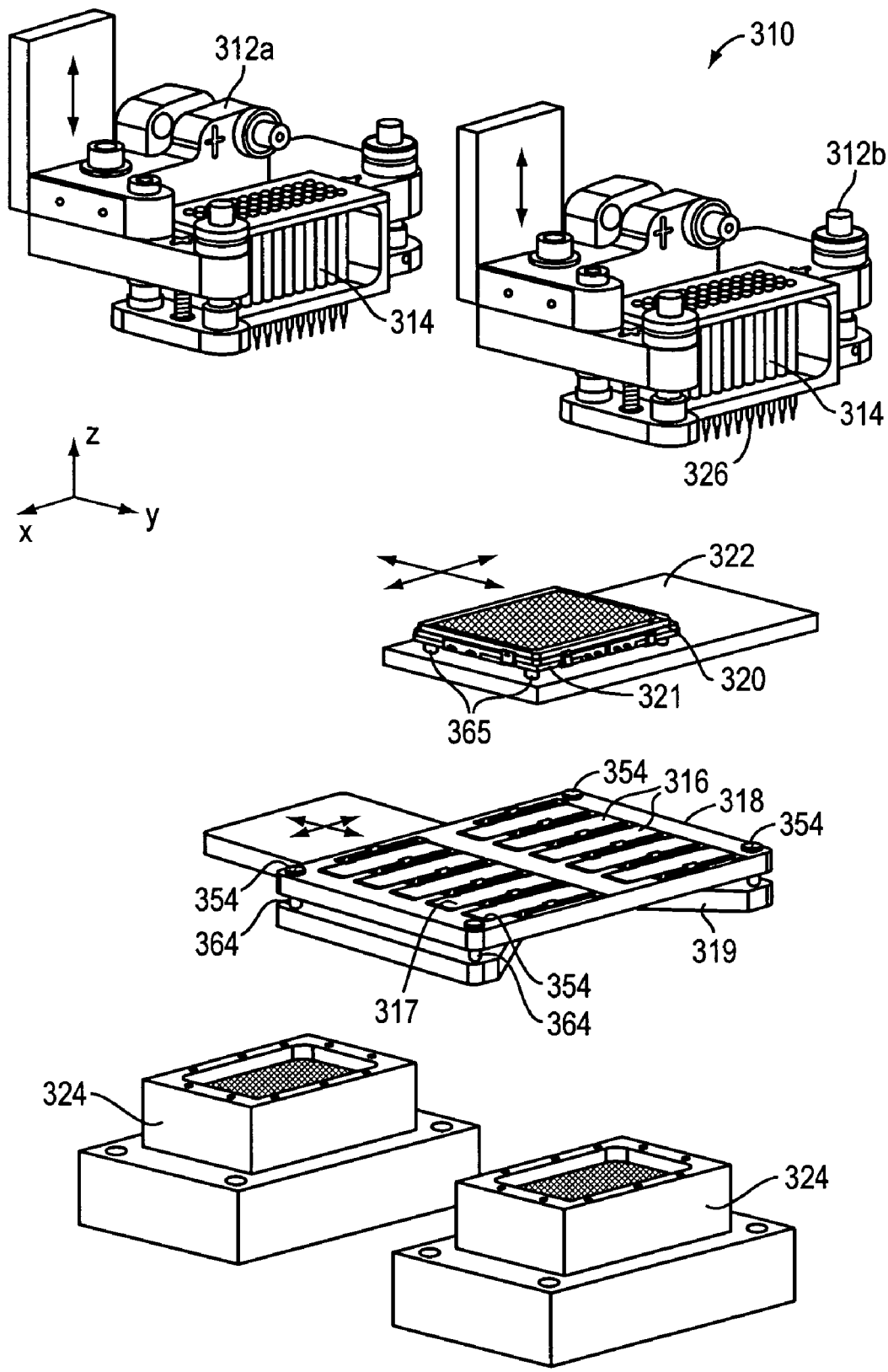
FIG. 11 is a schematic perspective view of a microarrayer architecture in accordance with one embodiment of the invention.

With reference to FIG. 11, a microarrayer assembly 310 having a plurality of printheads 312 is illustrated. In the illustrated embodiment, the motion of two independently mobile printheads 312a, 312b (collectively 312), each including one or more deposit elements 314, for instance solid pins 314, and each constrained to move in a vertical axis (the Z-axis), are coordinated with the motions of a) a substrate-holder support 319, which may move in any direction within an x-y plane substantially perpendicular to the aforementioned vertical axis when disposed beneath the printheads, and b) a fluid-reservoir holder support 322, which may move in any direction within an x-y plane separate from the plane of motion of the substrate-holder support 319 when disposed beneath the printheads, also essentially perpendicular to the aforementioned vertical axis. The axes of motion of the printheads 312a and 312b are parallel and displaced from each other laterally (horizontally). The substrate-holder support 319 and fluid-reservoir holder support 322 are independently mobile, but move in a coordinated manner to effect the deposition of fluid droplets upon the substrates 316. The substrates 316 and the fluid reservoirs 320 may be respectively mounted on a substrate-holder 318 and a fluid-reservoir holder 321 as earlier described. The required motorized linear stages associated with the X, Y and Z motions have been omitted from the drawing for clarity.

With continued reference to FIG. 11, the stages holding the two printheads 312 are mounted at the same height, and are separated in the Y dimension by a distance larger than the width of the substrate-holder 318 (or its support holder 319 if larger). The deposit elements 314 are mounted in the printheads 312 with a repetitive spacing which is a function of the well spacing of the fluid-reservoirs 320.

The fluid reservoir 320 (such as a microplate, with 96 wells, or a multiple of 96 wells), for supplying fluid samples to the tips of the deposit elements 314 of the printheads 312 is mounted on a fluid-reservoir holder 321, which in turn is held on the robotically controlled substrate-holder support 322 using the planarization system described earlier. In one embodiment, the fluid-reservoir-holder support 322 may:

a) move such that any set of wells of the fluid-reservoir 320 are positioned directly below the deposit elements 314 of either of the printheads 312 to allow charging or re-charging of those deposit elements 314 by having the deposit elements 314 dip into the fluids held in the wells, b) move clear of the vertical path of the printheads 312 to allow the printheads 312 to descend below the X-Y plane in which the fluid-reservoir 320 moves when disposed beneath the printhead to i) deposit spots of fluid onto the substrate 316, or ii) access wash stations 324 below (in the illustrated embodiment, there are separate wash stations 324 for each printhead 312, although in another embodiment a single mobile wash station is used), and c) move clear of the vertical paths of both printheads 312 into an area in which the fluid-reservoir holders 321 can be accessed for manual or robotic replacement of the fluid-reservoir holders 321 (and hence the fluid reservoirs 320).

The substrate-holder support 319 is mechanically arranged such that, in one embodiment, it may:

a) move such that any desired respective set of printing locations on any substrate 316 can be positioned directly below the deposit elements 314 on either printhead 312 to allow deposition of a fluid sample, or fluid samples, on the substrate 316 when the printheads 312 are lowered such that the tip 326 of each deposit elements 314 is in contact with, or the droplet of fluid on the tip 326 of each deposit element 314 is in contact with, the top surface 317 of the substrate 316, b) move clear of the vertical path of the printheads 312 to allow the printheads 312 to descend below the X-Y plane in which the substrate-holder support 319 moves when disposed beneath the printheads to access a wash station 324, or wash stations 324, below, and c) move clear of the path of the printheads 312 into an area from which the substrate-holder 318 may be accessed for manual or robotic removal or replacement of the substrate-holder 318 for the purpose of removal or replacement of the substrates 316.

Deposition of droplets of biological or chemical fluid material upon the substrate(s) 316 may be achieved with two printheads 312, for example, using either of two methods: sequential or concurrent washing. The method associated with sequential washing is described first (note: this procedure assumes that the deposit elements 314 of both printheads 312 have been washed and that fluid-reservoirs 320 and substrates 316 are already installed in the microarrayer assembly 310). Droplet deposition using a sequential washing cycle may be achieved by the following sequence of actions; however, other motion sequences may also be used, and the following is by way of example only:

a) move printheads 312a, 312b to their fully raised positions, b) move the fluid-reservoir holder support 322 in the X-Y plane to align a first set of wells of the fluid-reservoir 320 under the deposit elements 314 of the printhead 312a while simultaneously moving the substrate-holder support 319 in tandem with the fluid-reservoir holder support 322 such that the absolute distance between the fluid-reservoir holder support 322 and the substrate-holder support 319 remains substantially constant, c) move the substrate-holder support 319 to align a first set of desired print locations on a first substrate 316 under the deposit elements 314 of the printhead 312a, d) lower the printhead 312a in the Z-axis such that the tips 326 of the deposit elements 314 of the printhead 312a are immersed in the first set of fluid samples, and a small amount of fluid is captured on the tips 326 of the deposit elements 314 when the deposit elements 314 are subsequently lifted out of the wells, e) raise the printhead 312a away from the fluid-reservoir 320 a sufficient distance such that the fluid-reservoir holder support 322 can be moved in its X-Y plane without contacting the deposit elements 314 or the printheads 312, f) move the fluid-reservoir holder support 322 away from the vertical axis of the printhead 312*a* to enable the printhead 312*a* to descend unobstructed below the X-Y plane of motion of the fluid-reservoir holder support 322, g) lower the printhead 312*a* in the Z-axis such that the tip 326 of each deposit element 314 is in contact with, or the droplet of fluid on the tip 326 of each deposit element 314 is in contact with, the top surface 317 of the substrate 316, thereby depositing small droplets of fluid (one droplet per deposit element 314) onto the top surface 317 of the substrate 316, h) raise the printhead 312*a* above the X-Y planes of motion of both the fluid-reservoir holder support 322 and the substrate-holder support 319 such that either can move in their respective planes without contacting the deposit elements 314 or the printheads 312, i) repeat steps b) through h) for the second and subsequent sets of desired print locations on the first substrate 316 using the first set of wells of the fluid-reservoir 320, j) when all desired print locations on the first substrate 316 have been spotted using the first set of wells of the fluid-reservoir 320, repeat b) through h) for the next and subsequent substrates 316 with the first set of wells of the fluid-reservoir 320, k) at the completion of spotting of all substrates 316 with the first set of wells of the fluid-reservoir 320, move the fluid-reservoir holder support 322 in its X-Y plane of motion to align a second set of wells of the fluid-reservoir 320 under the deposit elements 314 of the printhead 312*b* while simultaneously moving the substrate-holder support 319 in tandem with the fluid-reservoir holder support 322 such that the absolute distance between the fluid-reservoir holder support 322 and the substrate-holder support 319 remains substantially constant, l) repeat steps c) through j), but now using the printhead 312*b*. While the printhead 312*b* is spotting, the deposit elements 314 of the printhead 312*a* are washed. After washing, the printhead 312*a* is raised to its fully raised position above the X-Y planes of motion of the substrate-holder support 319 and the fluid-reservoir holder support 322, and the printhead 312*a* waits unused until the printhead 312*b* enters a wash cycle, and m) continue repeating the above described sequence, changing operating printheads 312 at each wash cycle event, until all desired print locations are spotted on all substrates 316 from all desired sets of wells in the fluid-reservoir(s) 320.

Alternatively, deposition of droplets of biological or chemical fluid material upon the substrate(s) 316 can be achieved with the two printheads 312*a*, 312*b* using the concurrent washing method. With continued reference to FIG. 11, one example of the concurrent washing method is as follows:

a) move the printheads 312*a*, 312*b* to their fully raised positions as shown in FIG. 11, b) move the substrate-holder support 319 under the printhead 312*b*, c) move the fluid-reservoir holder support 322 in its X-Y plane of motion to align a first set of wells of the fluid-reservoir 320 under the deposit elements 314 of the printhead 312*a*, d) move the substrate-holder support 319 to align a first set of deposition locations on the first substrate 316 for the first set of fluid samples under the deposit elements of the printhead 312*a*, e) lower the printhead 312*a* in the Z-axis such that the tips 326 of the deposit elements 314 of the printhead 312*a* are immersed in the first set of fluid samples, and a small amount of fluid is captured on the tips 326 of the deposit elements 314 when the deposit elements 314 are subsequently lifted out of the liquid samples, f) raise the printhead 312*a* away from the fluid-reservoir holder support 322 a sufficient distance that the fluid-reservoir 320 can be moved in its X-Y plane of motion without contacting the deposit elements 314 or the printhead 312*a*, g) move the fluid-reservoir holder support 322 in it's X-Y plane of motion to align a second, new set of wells of the fluid-reservoir 320 under the pins 314 of the printhead 312*b*. The separation of the printheads 312*a*, 312*b* is such that with any set of wells of the fluid-reservoir(s) 320 located under the deposit elements 314 of the printhead 312*b*, the printhead 312*a* can descend unobstructed below the X-Y plane of motion of the fluid-reservoir holder support 322, h) lower both printheads 312*a*, 312*b* in the Z-axis such that (i) the tips 326 of the deposit elements 314 of the printhead 312*a* are in contact with, or the droplet of fluid on the tip 326 of each deposit element 314 of the printhead 312*a* is in contact with, the top surface 317 of the substrate 316, thereby depositing small droplets of fluid (one droplet per deposit element 314) onto the top surface 317 of the substrate 316, and (ii) the tips 326 of the deposit elements 314 of the printhead 312*b* are immersed in the second set of fluid samples, and are charged with fluid samples, i) raise both printheads 312*a*, 312*b* above the X-Y planes of motion of both the fluid-reservoir holder support 322 and the substrate-holder support 319 such that the fluid-reservoir holder support 322 and the substrate-holder support 319 can move in their respective planes without impacting the printheads 312*a*, 312*b*, j) move the substrate-holder support 319 such that the first set of desired deposition locations on the first substrate 316 for the second set of fluid samples is directly below the deposit elements 314 of the printhead 312*b*, k) move the fluid-reservoir holder support 322 such that the first set of wells of the fluid-reservoir 320 is again directly below the deposit elements 314 of the printhead 312*a*, l) lower both printheads 312*a*, 312*b* in the Z-axis such that (i) the tips 326 of the deposit elements 314 of the printhead 312*b* are in contact with, or the droplet of fluid on the tip 326 of each deposit element 314 is in contact with, the top surface 317 of the substrate 316, thereby depositing small droplets of fluid (one droplet per deposit element 314) onto the top surface 317 of the substrate 316, and (ii) the tips 326 of the deposit elements 314 of the printhead 312*a* are immersed again in the first set of wells of the fluid-reservoir 320 and are recharged with fluid samples, m) raise both printheads 312*a*, 312*b* above the X-Y planes of motion of both the fluid-reservoir holder support 322 and the substrate-holder support 319 such that both the fluid-reservoir holder support 322 and the substrate-holder support 319 can move in their respective planes without impacting the printheads 312*a*, 312*b*, n) move the substrate holder support 319 to align a second set of deposition locations on the first substrate 316 for the first set of fluid samples under the deposit elements 314 of the printhead 312a, o) move the fluid-reservoir holder support 322 in it's X-Y plane of motion to align the second set of wells of the fluid-reservoir 322 under the deposit elements 314 of the printhead 312b, p) repeat steps h) through o), but now for the second, and all other desired deposition locations, until all desired deposition locations on the first substrate 316 have received depositions from the first two sets of wells of the fluid-reservoir 320, q) repeat the above sequence until all desired substrates 316 on the substrate-holder 318 have been spotted from the first two sets of wells of the fluid-reservoir 320, r) move the fluid-reservoir holder support 322 and the substrate-holder support 319 away from the axes of motion of both the printheads 312a, 312b and lower the printheads 312a, 312b to the wash stations 324 below, s) after washing the deposit elements 314 of both printheads 312a, 312b concurrently, restart at step a) but with the use of the third and fourth set of wells on the fluid-reservoir 320, and t) repeat the above sequence for each subsequent set of wells on the fluid-reservoir 320 until all desired deposition locations on all substrates 316 on the substrate-holder 318 have been spotted from all wells of the fluid-reservoir 320.

Although the microarrayer assembly 310 illustrated in FIG. 11 includes the fluid-reservoir holder support 322 moving in an X-Y plane of motion above the plane of motion of the substrate-holder support 319, in another embodiment, the substrate-holder support 319 moves in an X-Y plane of motion that is above the plane of motion of the fluid-reservoir holder support 322. Further embodiments may include any of the microarrayer assembly components earlier described, for instance, a substrate-holder storage and a fluid-reservoir holder storage. The described printing methods can also be altered to provide equal exposure time printing.

Notwithstanding the suitability of the architecture shown in FIG. 11 for use with solid deposition pins 314, the architecture can also be used with quill pins, pens or ink jet devices. One beneficial aspect of the architecture of FIG. 11 using these devices is the potential minimization of, or elimination of, spotting time lost because of washing. Wash times for quill pins, pens and ink-jet devices can be longer than that for solid pins 314 because of the difficulty in flushing sample fluids from inner, less-accessible surfaces. Using a sequential wash method and the architecture of FIG. 11, deposition rates using quill pins, pens, or aspirating ink-jet dispensers may be increased substantially since one printhead 312 may continue deposition operations while the deposit elements 314 on the other printhead 312 are being washed.

Figure 12:
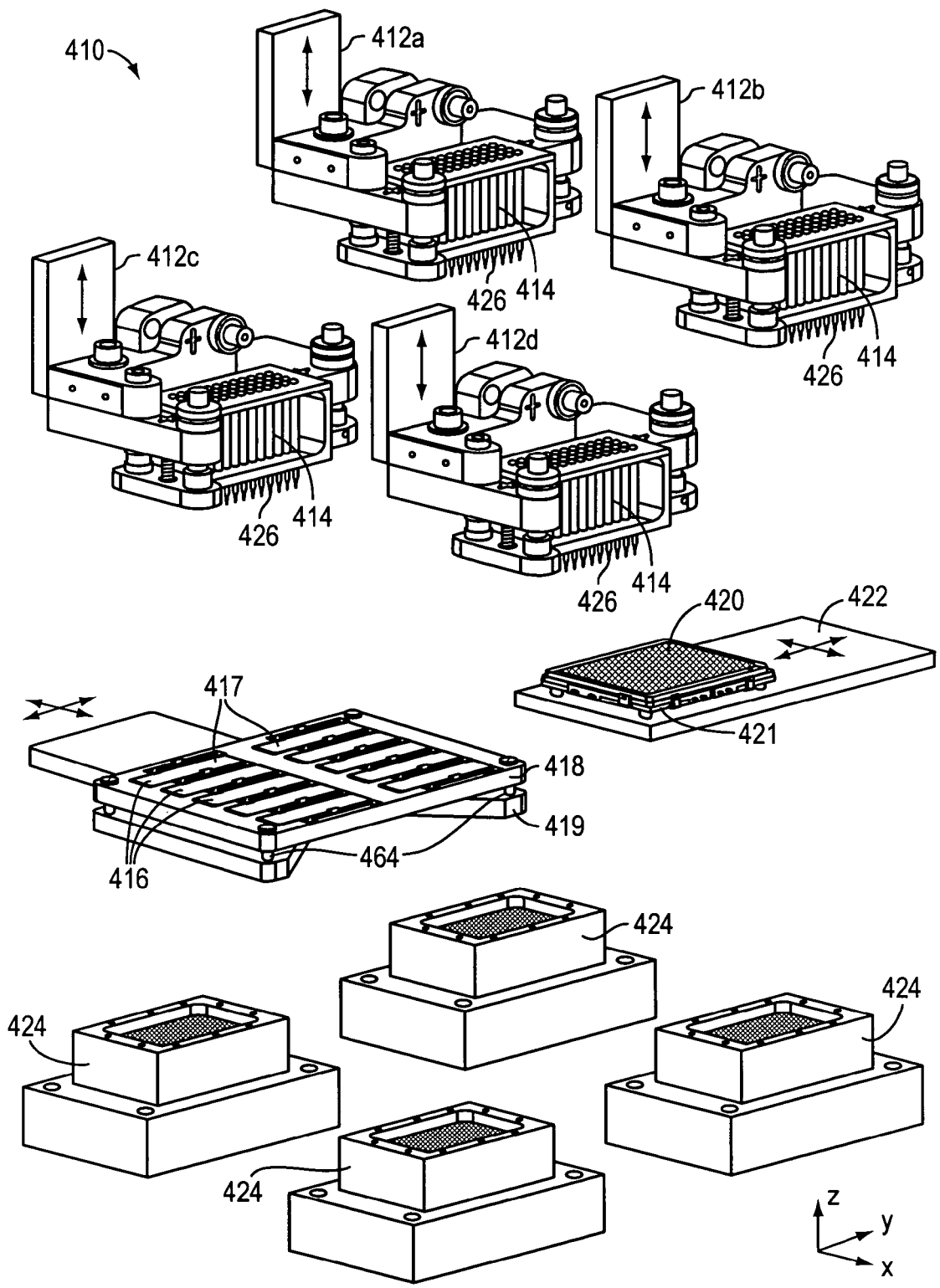
FIG. 12 is a schematic perspective view of a microarrayer architecture in accordance with one embodiment of the invention.

With reference to FIG. 12, in another embodiment, the deposition rate of a microarrayer assembly 410 may be increased by using four independently mobile printheads 412. One advantage of this embodiment is that the deposition rate benefit derived from the interlacing of dip-and-deposit actions of two printheads as described with respect to FIG. 11 can be achieved without losing any deposition time due to a wash cycle. In the illustrated embodiment, the motion of the four independently mobile printheads 412, each constrained to move in a vertical axis, are coordinated with the motions of a) a substrate-holder support 419, which may move in any direction within a plane substantially perpendicular to the aforementioned vertical axis when it is disposed beneath the printheads, and b) a fluid-reservoir holder support 422, which may move in any direction within a separate plane when it is disposed beneath the printheads, also essentially perpendicular to the aforementioned vertical axis, that is displaced from the plane of motion of the substrate-holder support 419. The axes of motion of the printheads 412 are parallel and displaced from each other laterally (horizontally). The printheads 412, in one embodiment, may be arranged linearly, or, as shown, in the form of a square or rectangle. The substrate-holder support 419 and the fluid-reservoir holder support 422 are independently mobile, but move in a coordinated manner to effect the deposition of fluid droplets upon the substrates 416. Position sensing (e.g. using position encoders) allows automated monitoring of the location of the mobile elements of the microarrayer assembly 410 and computer control inhibits any undesired contact between the components of the assembly 410. As before, the fluid reservoirs and substrates are respectively disposed on the substrate-holder support 419 and the fluid-reservoir holder support 422 and are accurately positioned within a known and defined plane and at a known location within the plane.

In the four-printing-head architecture, two printheads 412a and 412b are initially alternating in interlaced "dip-and-deposit" actions (one is recharging its deposit elements 414 in the fluid-reservoir 420, while the other is depositing onto the substrate 416, and then vice versa), and the other two printheads 416c and 416d, are washed and then wait to be used. When a wash cycle is required for the first pair of printheads 412a, 412b (for instance at the conclusion of their depositing a set of fluid samples at all desired deposit locations on all substrates 416 on the substrate-holder 418), the fluid-reservoir-holder support 422 and substrate-holder support 419 are moved beneath the other pair of printheads 412c, 412d which then take over the printing operations. For each pair of printheads, in one embodiment, the interlaced dip-and-deposit actions follow the principles outlined in the "concurrent wash" method previously described for the two printing-head assembly illustrated in FIG. 11.

In other embodiments, the use of:

a) a plurality of independently mobile printheads, each constrained to move in parallel single axes, coupled with b) the motion of a fluid-reservoir in any direction within a plane perpendicular to the single axes when disposed beneath the printheads, and c) independent motion of a substrate in any direction within a plane perpendicular to the single axes but displaced from the plane of motion of the fluid-reservoir when disposed beneath the printheads can be extended to any number of printheads to improve droplet deposition rates. All such embodiments are included within the scope of the invention.

v) Microarrayer Architectures with a Plurality of Deposition Engines

Microarrayer components that include inserts that engage datums on another piece of equipment, as previously described, permit such components to be loaded into a microarrayer assembly with precise, repeatable positioning. For example, when the substrates are top-referenced in the substrate-holder, the top-surfaces of the substrates may be positioned in a known plane and absolute position with respect to the printhead. Similarly, the use of fluid-reservoir holders incorporating inserts that include reference surfaces that engage datums disposed on a fluid-reservoir holder support, as previously described, permits such fluid-reservoir holders to be loaded into a microarrayer assembly with precise, repeatable positioning of the fluid-reservoirs with respect to the printhead. The ability to repeatably and accurately load substrate-holders and fluid-reservoirs or fluid-reservoir holders into a microarrayer assembly enables a variety of other architectures to be developed that increase throughput. For instance, in one embodiment, a multi-engine microarrayer assembly increases throughput by arranging a plurality of "deposition engines" to operate together in a cooperative manner. A "deposition engine," as the term is used herein, includes the functionality to a) deposit fluid droplets upon substrates mounted on substrate-holders, b) optionally load and unload fluid-reservoirs from an external conveyor and c) load and unload substrate-holders from an external conveyor. Concatenating a plurality of modular deposition engines enables scalability in the design of a microarrayer apparatus to achieve a desired level of throughput (i.e. depositions per hour). Autonomous operation of such a microarrayer assembly is enabled by:

i) automated supply and return of fluid-reservoirs (or of fluid-reservoir holders with fluid-reservoirs thereon) in aspirating systems between a fluid-reservoir storage and the deposition engines, for instance, by the conveyor, and ii) automated supply and return of substrate-holders between a substrate-holder storage and the deposition engines, for instance by a conveyor.

In addition, the ability to replenish source-material fluid-reservoirs and substrates during the printing process by re-stocking the fluid-reservoir storage and the substrate-holder storage facilitates continuous printing operation with minimal or no cessation in printing operations.

Figure 13:
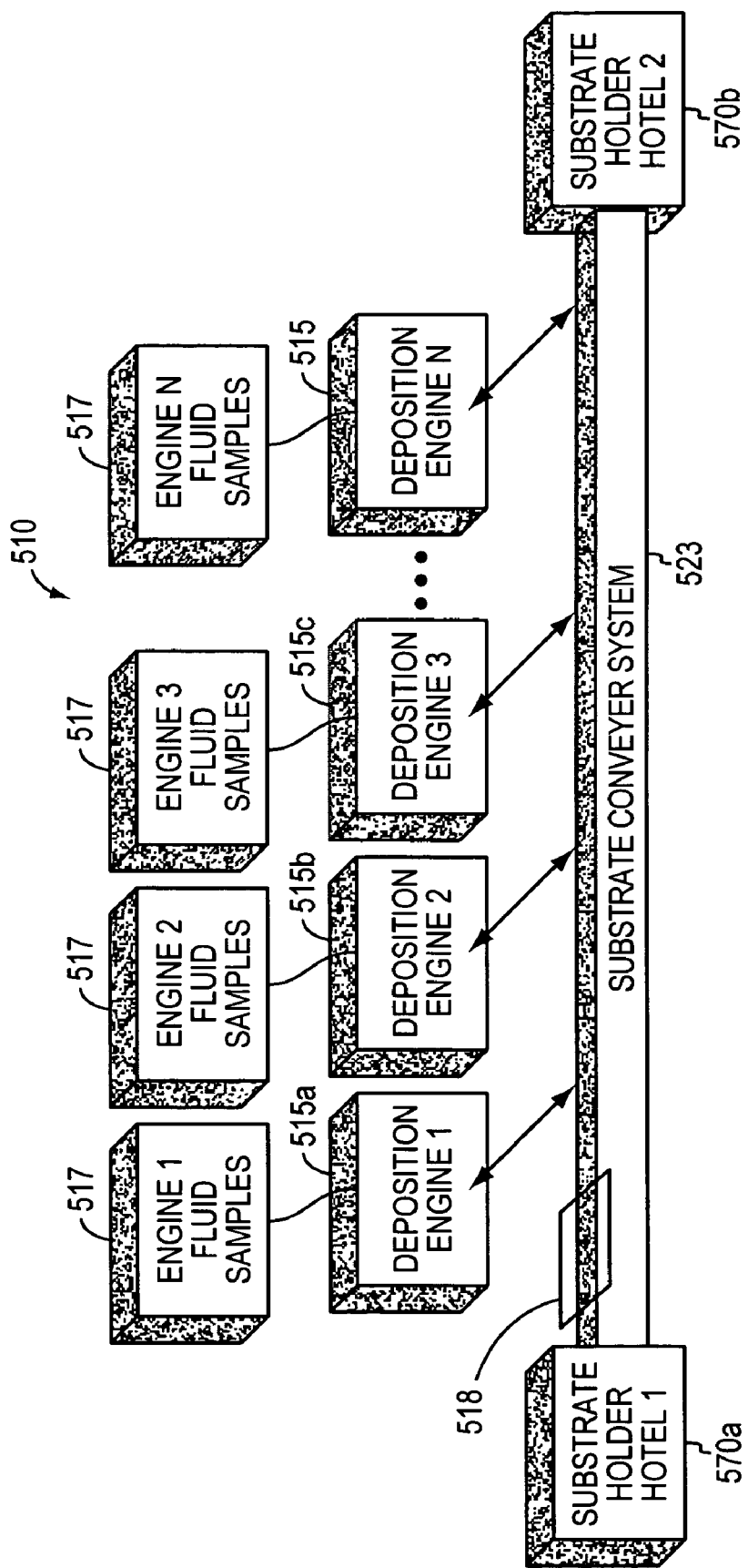
FIG. 13 is a schematic block diagram illustration of a multi-engine microarrayer assembly for use with non-aspirating ink-jet dispensers in accordance with one embodiment of the invention.

With reference to FIG. 13, one embodiment of a microarrayer assembly 510 that includes a plurality of deposition engines 515 is illustrated. The assembly utilizes non-aspirating ink-jet devices. A non aspirating ink-jet deposition device is a device that is fed a continuous stream of sample fluid, (for instance via a tube from a large reservoir 517) thereby eliminating the need to aspirate fluid from a fluid-reservoir, such as a microplate. Each deposition engine 515 shown in FIG. 13 represents a deposition engine using one or more non-aspirating ink-jet devices. Depositions are performed inside the deposition engines using substantially the same spotting techniques as earlier described, and are therefore not repeated here.

With continued reference to FIG. 13, substrate-holders 518 are initially installed in the substrate-holder storage 570a. To deposit fluid droplets upon the substrates 516, a substrate-holder 518 with substrates 516 thereon is removed from the substrate-holder storage 570a and passed, via a conveying system 523, to deposition engine 515a, which loads the substrate-holder 518 by placing it on a substrate-holder support 519 and commences deposition operations upon the substrates 516 thereon. Once the fluid samples of the deposit engine 515a have been deposited on all the substrates 516 on the substrate-holder 518, the substrate-holder 518 is moved from the deposit engine 515a to the deposit engine 515b, and a new substrate-holder 518 is loaded into deposit engine 515a. When both engines 515a and 515b have completed deposition operations, the first substrate-holder 518 is passed to deposit engine 515c and the second substrate-holder 518 is passed to deposit engine 515b, and a new substrate-holder 518 is removed from the substrate-holder storage 570a and installed into the deposit engine 515a. The sequence of passing substrate-holders 518 from engine to engine continues until all engines have deposited all fluid samples on all substrates 516 of all substrate-holders 518, and all the substrate-holders 518 have been installed in substrate-holder storage 570b. Two substrate-holder storages 570a and 570b are shown in FIG. 13, however in some embodiments, only a single substrate-holder storage 570 is used to dispense and receive substrate-holders 518.

Figure 14:
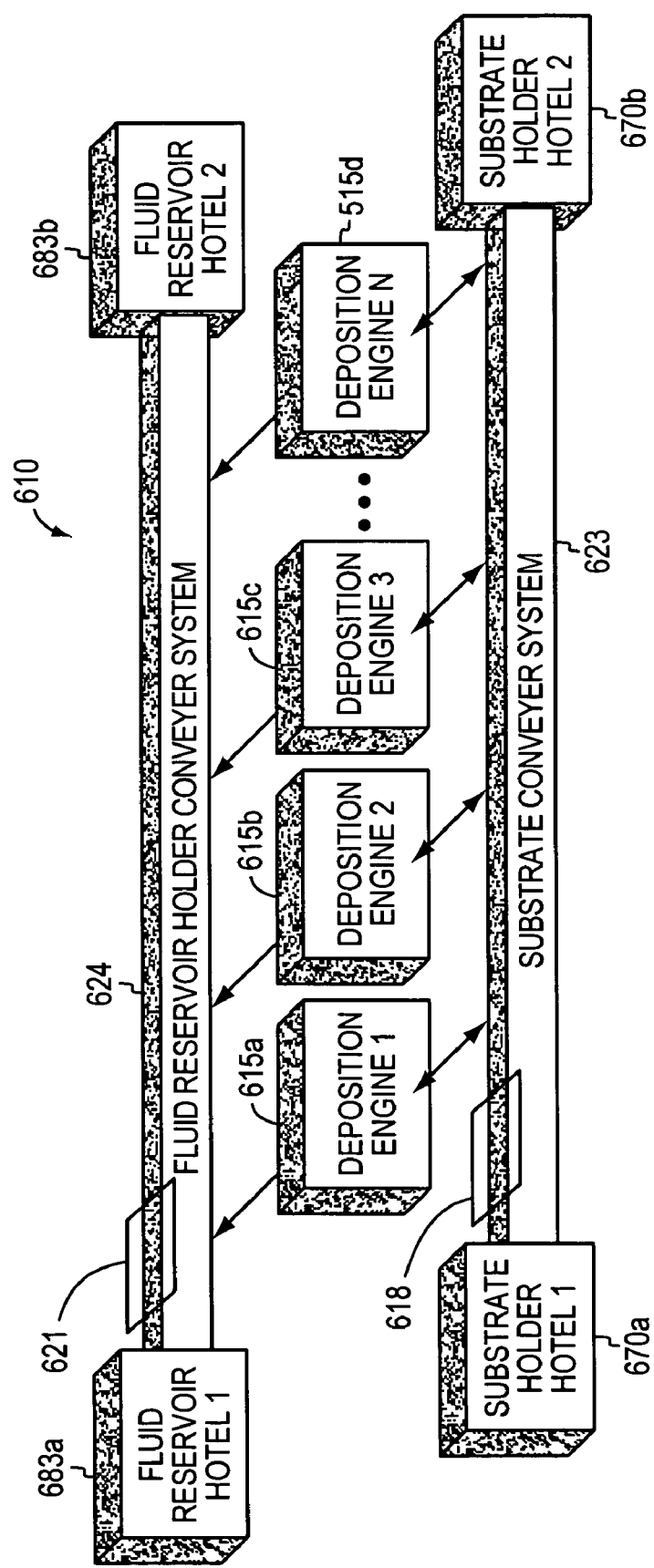
FIG. 14 is a schematic block diagram illustration of a multi-engine microarrayer assembly for use with aspirating deposit elements in accordance with one embodiment of the invention.

With reference to FIG. 14, another embodiment of a multiple deposition engine microarrayer assembly 610 is illustrated. In this embodiment, which uses solid pins, pens, or aspirating ink-jet devices within each deposit engine 615, two conveyor systems 623, 624 are used. The first conveyor 623 transfers substrate-holders 618 and the second conveyor 624 transfers fluid-reservoir holders 621 with fluid reservoirs 620 secured thereon or alternatively a fluid reservoir 620 that is not secured on a holder 621. In the illustrated embodiment, four deposition engines 615 are shown; however, any other number of deposition engines 615 can be concatenated to achieve a desired level of throughput.

Several methods exist for operating the assembly of FIG. 14. In one embodiment, four substrate-holders 618 are removed from the substrate-holder storage 670a and installed in the four engines 615a, 615b, 615c, 615d via the robotic conveyor system 623. Next, the first fluid-reservoir holder 621 holding a fluid-reservoir 620 is removed from the fluid-reservoir holder storage 683a and installed, via the robotic conveyor 624, in the deposit engine 615a. All fluid samples in the first fluid-reservoir 620 are deposited on all the substrates 516 on the first substrate-holder 518. The first fluid-reservoir holder 621 is then transferred to the deposit engine 615b, via the robotic conveyor 624, and a second fluid-reservoir holder 621 is installed, from the fluid-reservoir holder storage 683a into the deposit engine 615a. Now both the deposit engine 615a and the deposit engine 615b operate to deposit all fluid samples from the respective fluid-reservoirs 620 onto all the substrates 616 on the respective substrate-holders 618. After the completion of spotting operations, the first fluid-reservoir holder 621 is transferred to the deposit engine 615c, the second fluid-reservoir holder 621 is transferred to the deposit engine 615b, and a new third fluid-reservoir holder 621 is installed in the deposit engine 615a, via the robotic conveyor 624. The engines 615a, 615b, 615c operate to deposit all fluid samples from the respective fluid-reservoirs 620 onto all the substrates 616 on the respective substrate-holders 618. The same process is repeated to spot from a fourth fluid-reservoir 620 and so on. As a further step, the first fluid-reservoir holder 621 holding the first fluid-reservoir 620 is transferred into the fluid-reservoir holder storage 683b as the fluid-reservoirs 620 continue to pass down the line of deposition engines 615. The sequence of passing the fluid-reservoirs holders 621 from engine to engine continues until all the fluid-reservoir holders 621 are transferred to the fluid-reservoir holder storage 683b. At this point, the four substrate-holders 618 installed in the four engines 615 have received all fluid samples on all of their respective substrates 616. Therefore, the substrate-holders 619 are removed from the deposit engines 615 and transferred to the substrate-holder storage 670b, and four fresh substrate-holders 618 are loaded into the deposit engines 615 via the robotic conveyor 623. The process described above is then repeated, but with the fluid-reservoir holders 621 now moving from fluid-reservoir holder storage 683b to fluid-reservoir holder storage 683a.

In another embodiment, rather than passing fluid-reservoirs 621 between deposit engines 615 as just described, substrates 616 or substrate holders 619 are passed between the deposit engines 615, and the fluid reservoirs 620 or fluid reservoir holders 621 are initially loaded into the engines 615.

Deposition operations of the arrayer engines in a multi-engine assembly such as that described can be performed synchronously or asynchronously. In synchronous operation, the printheads, substrate-holder supports, and fluid-reservoir holder supports in each deposition engine move in unison to deposit fluid on the substrates. In asynchronous operation, the deposition actions involving any motion of printheads, substrates or microplates within an engine are independently controlled. However, the deposition engines remain coordinated with respect to starting and ceasing deposition operations and transferring of fluid-reservoir holders and substrate-holders between engines and storage centers. Various other components may be shared between the engines, such as a computer control system and operator interfaces, a cover, a heating, cooling, and humidification control system, air filters, vacuums, water supplies, and pressure supplies.

The multi-deposit engine microarrayer assemblies described above may include any of the features earlier described, for instance, one, two or four independently mobile printheads.

In further embodiments, the above microarrayer assemblies 10, 210, 310, 410, 510, 610 may include a variety of other features. For instance, in one embodiment, a sensor is included for sensing the presence or absence of a substrate-holder within the receptacle (or bay) of a substrate-holder storage, or within a microarrayer, or within a deposition engine of a multi-engine microarrayer. The sensor can be of any type including, but not limited to, optical, capacitive, inductive, magnetic, infra-red, radio frequency or electro-magnetic. A sensor based on the making or breaking of an electrical circuit may also be used. Similar sensors may be used for sensing the presence or absence of fluid-reservoirs or fluid-reservoir holders in the microarrayer assemblies. In another embodiment, a sensor may be included for sensing the height of fluid within each well of a fluid reservoir. The presence of fluid heights outside a desired specified range may adversely effect the fluid capture by the deposition element and the consistency of fluid droplet deposition on the substrates. The sensor can be of any type including, but not limited to, optical (direct measurement using modulated transmission, or indirect measurement using physical displacement of a beam reflected from the fluid surface at an angle other than perpendicular incidence), and infra-red or radio frequency.

Another use for the microarrayers described above is to produce cell arrays. Cell arrays are composed of individual cells (or small quantities of cells) deposited in ordered arrays upon a substrate such as a glass slide or a multi-well target plate. Whereas the deposited volume and the size of the printheads used to produce cell arrays may be larger than that used for genomic or proteomic microarrays, such arrays may be generated by the techniques and methods disclosed herein and are included with the scope of the present invention.

vi) Spotting a Binding Agent on a Substrate:

Microarray substrates used for the capture of biological materials are usually coated over their entire surface with a material that binds biological molecules. Typically, a certain first set of biological molecules are spotted onto the coating in specific spot locations to bind to the coating in those locations. A sample of biological material under test is then effectively washed over the set of spots such that biological interactions between the set of molecules first spotted and the sample can be identified by locating the attachment of the sample to the substrate. It is common, however, in genomic and proteomic microarray experiments for the sample to also bind to the slide coating in an undesired, non-specific manner (i.e. not related to a particular genome sequence or fold structure).

A potential solution for this problem is to only place the "binding agent" material on the slide in the location where the first set of biological molecules are to be placed. The rest of the substrate's surface can be left bare, or with a coating of material that will inhibit or suppress non-specific binding. Using this concept, the binding agent can be deposited on the substrate in spot locations that are later re-spotted with the set of biological molecules. Some of the microarrayer embodiments herein described, in particular a) the ability to accurately position substrates repeatedly under a printhead using a substrate-holder that is positioned in a known location in a plane and b) the provision and use of multiple printheads, may be used to realize the above technique. Using the architectures described, a series of materials having different functions, may be spotted onto the same location on a substrate. It is also possible to deposit the sample only at the locations of the first set of biological molecules, instead of washing it over the entire array, resulting in significant reduction in the amount of sample required 2) Tissue Arrayer Embodiments The embodiments described in the foregoing for the dispensing of fluid droplets in the form of microarrays are readily adapted to an apparatus for the deposition of semi-solid or solid tissue samples in ordered arrays.

Figure 15:
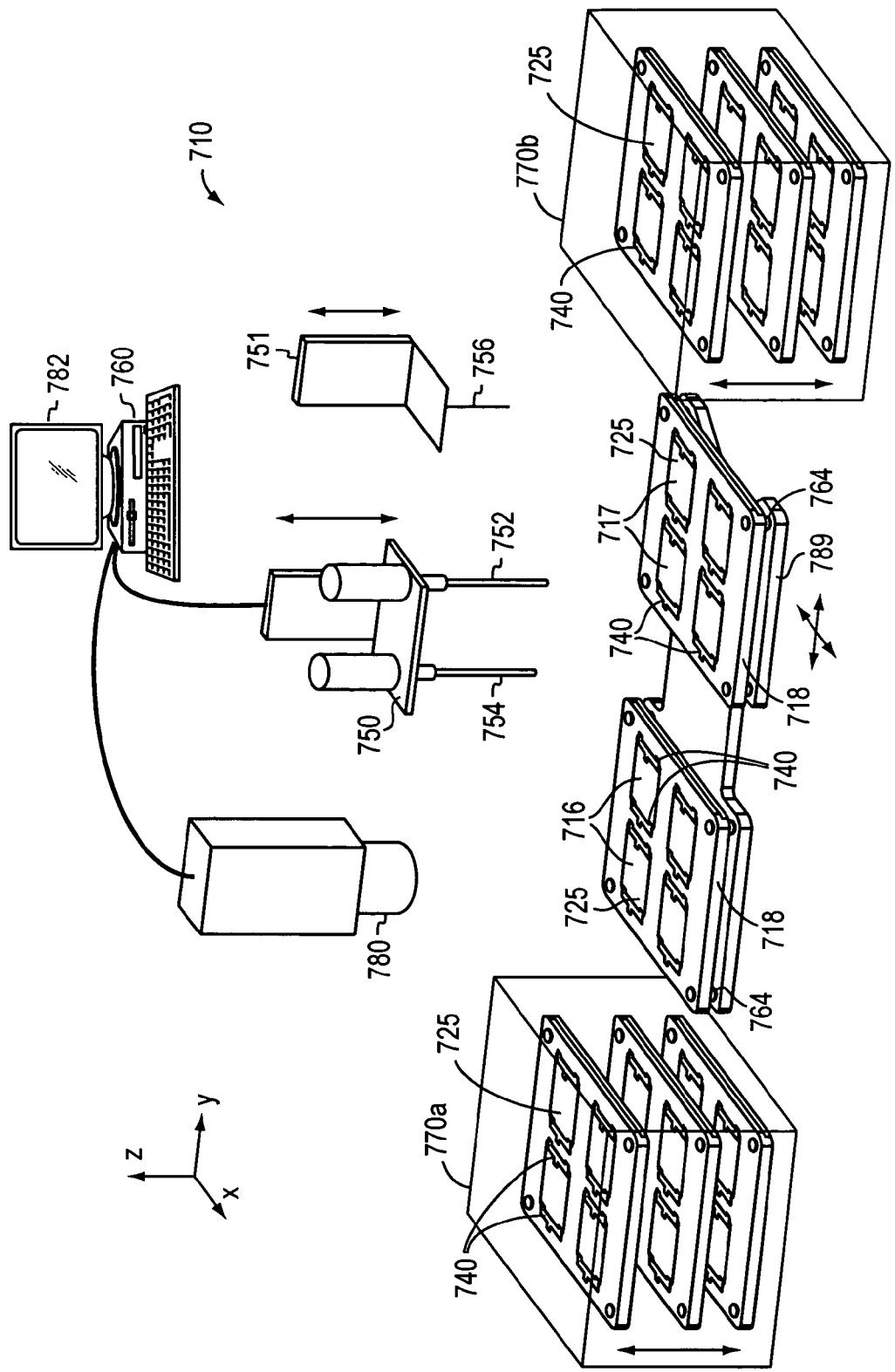
FIG. 15 is a schematic perspective view of a tissue arrayer in accordance with one embodiment of the invention.

With reference to FIG. 15, in one embodiment of a tissue arrayer 710, donor and receiver blocks 716, 717, for example, made of paraffin, are mounted in a block-holders 718 that include top-referencing to maintain the top of the blocks 716, 717 in a known, consistent plane. The system is similar to that described in FIG. 3 for use with substrates. The top surface of the paraffin blocks are pressed from below against a reference surfaces 740 (or reference elements), of the block-holders 718 that are machined and/or constructed to ensure that the top surface 725 of each block 716, 717 is in a desired plane, and that the block's top surface 725 is substantially coplanar with that of every other block 716, 717 held by the block-holder 718, if more than one block 716, 717 is installed in the holder 718. The block 716, 717 is held against the block-holder's reference surfaces 740 by means of spring clips or other locking mechanisms with resilient or biasing members. In another embodiment, a removable block-mounting fixture similar to that described in FIGS. 4A-4C for use with substrates is provided for use with donor and receiver blocks 716, 717. One advantage of using top-referencing as described is that the donor and receiver blocks 716, 717 are repeatably located in the block-holder 718 at each loading. This facilitates consistent and accurate removal of tissue cores from the donor-block 716 and consistent and accurate placement of tissue cores in the receiver block 717.

In another embodiment, the block-holders 718 include inserts designed to rest upon datums disposed on a mobile block-holder support 789. The referencing systems previously described for use with the microarrayer substrate holder, the substrate-holder support, the fluid-reservoir holder, and the fluid-reservoir holder are also applicable to the block-holder 718 and the block-holder support 789 and will therefore not be further described. The referencing system permits installation of the block-holders 718 onto the mobile block-holder supports 789 of the tissue arrayer 710 in a predictable, repeatable manner such that the top surfaces 725 of the donor and receiver blocks 716, 717 may be located accurately within a known plane with respect to a coring head 750.

In one embodiment, overall block-holder and block-holder support system position accuracy is within ±0.02" in the x, y, and z-axes. In a preferred embodiment, overall block-holder and block-holder support system position accuracy is within ±0.002" in the z-axis and within ±0.01" in the x and y axes. In a more preferred embodiment, overall block-holder and block-holder support system position accuracy is within ±0.0002" in the z-axis and within ±0.001" in the x and y axes.

Similar to the microarrayer architectures described earlier, the use of block holders 718 and block-holder supports 789 that include a referencing system as described may be beneficially combined with block-holder storages 770a, 770b for temporally storing a multiplicity of block-holders 718 and the blocks 716, 717 thereon (either donor blocks or recipient blocks). In another embodiment, a conveyor system for removing and delivering block-holders 718 from and to the block-holder storages 770a, 770b may be included. In these embodiments, since manual loading/unloading of blocks 716, 717 from the section of the arrayer dedicated to coring/core-deposition is eliminated, many sources of error resulting from frequent human access to the coring area are minimized or eliminated.

Another benefit of the present invention is that block-holders 718 are readily loaded into, and removed from, the coring/deposition area of the tissue arrayer 710 without loss of positional accuracy (i.e. all properly prepared block-holders 718, when mounted on the block-holder support 719, will have their top surfaces 725 in the same plane, and at the same location and orientation.)

Another benefit produced by various embodiments of the invention is that the number of blocks 716, 717 that can be processed by the tissue arrayer 710 is limited only by the number of blocks 716, 717 on each block-holder 718 and the available number of block-holders 718 in the block-holder storages 770a, 770b. Moreover, in one embodiment, block-holders 718 can be removed from, and added to, the block-holder storages 770a, 770b while coring/core-depositions are underway on an active block-holder 718 loaded in the coring/deposition area of the arrayer 710. This facilitates continuous operation of the tissue arrayer 710.

Another benefit derived from various embodiments of the invention is that relatively small block-holders 718, holding, for example, 2 to 10 paraffin blocks 716, 717 can be used, since the number of blocks 716, 717 that can be processed is limited only by the capacity of the block-holder storage 770 and not the size of the block-holder 718. The use of smaller block-holders 718 enables the size of the deposition area and the volume of the tissue arrayer 710 to be reduced.

In another embodiment, scalable tissue arrayer designs are possible, since the size and functions of the coring/core-deposition equipment is no longer tied to the number of blocks 716, 717 that can be processed. For instance, embodiments using multi-engine tissue arrayers, using the principles discussed earlier for multi-engine microarrayers, can be developed.

With reference to FIG. 15, an embodiment of an automated tissue arrayer 710 is illustrated. Both the donor blocks 716 and the receiver blocks 717 may be moved in any direction within a horizontal X-Y plane when disposed beneath the coring head 750. The coring head 750 is constrained to move in an axis perpendicular to the X-Y plane. The coring head 750 includes two coring needles 752, 754. The first needle 752 cores receiver volumes in the receiver-blocks 717, and the second needle 754 extracts the tissue cores from the donor block 716 and deposits them in the aforementioned receiver volumes in the receiver block 717. In one embodiment, paraffin cores removed from the receiver block 717 are deposited into the voids left after coring of the donor block 716 to help maintain the latter's structural integrity. In another embodiment, liquid or semi-solid paraffin, or other suitable material, is injected into the voids of the donor-block 716 to maintain the latter's structural integrity. In a further embodiment, a needle 756 for dispensing liquid or semi-solid paraffin is vertically mobile and is mounted on a second vertical axis 751, offset laterally from the coring head 750 that holds first and second needles 752, 754.

The first and second needles 752, 754 are mounted to a linear vertical stage that is controlled by a computer 760. The vertical stage has encoders (linear or rotary) to provide positional feedback. The position of the needles 752, 754 in the vertical axis for coring and deposition operations is determined by the computer 760 under closed loop control. The donor blocks 716 are top referenced and are mounted in block-holders 718. The donor block-holder 718 rests upon datums 764 disposed on a shared platen 789, as previously described. Similarly, the receiver-blocks 717 are top referenced and are mounted in the block-holders 718. In one embodiment, a conveyor moves donor block-holders 718 to and from a donor block-holder storage 770a. Similarly, in another embodiment, a conveyor moves receiver-block holders to and from a donor-block holder storage 770b.

In other embodiments in accordance with the invention, in the same way that separate, parallel planes of motion were used for the substrate-holder and the fluid-reservoir holder in the motion architectures disclosed for microarrayers, the donor and receiver-block holders 718 may also be so arranged with separate independent planes of motion. Moreover, the planes of motion of the donor and receiver block holders 718, when under the coring head 750, may also be perpendicular to the axis of motion of the coring head 750.

With continued reference to FIG. 15, in another tissue arrayer embodiment, a high resolution camera system 780 and a high resolution video display 782 are also included. In one embodiment the camera system 780 mounted within the tissue arrayer 710 and the high resolution display 782 are located in different locations, such that remote examination and targeting of core locations in the tissue sample is possible. The camera system 780 and the coring head 750 are securely mounted on the same fixed bridge such that a known fixed offset in X and Y dimensions exists between them. In one embodiment, a known reference mark or series of reference marks are provided within the camera system's 780 field of view to establish the distance of separation between the coring head 750 and the camera 780 and/or to correct for non-linearities in the video image.

As an example, the tissue arrayer 710 may be used as follows. As a first step the donor-block 716, mounted in a known plane on a donor block holder 718 is moved in the X-Y plane under the high-resolution camera system 780, which is mounted to provide an image of the top surface 725 of the donor-block 716. A high resolution image of the donor block's tissue sample is displayed on the high resolution monitor 782. In the next step, using an animated pointing device such as a computer mouse, an operator moves a pointer, such as a computer cursor on the high resolution monitor 782, over the image of the tissue sample, and designates locations on the sample from which tissue cores are to be taken. In some embodiments, desired coring locations on a multiplicity of donor-blocks 716 are specified, by removing them, in turn, from a donor-block holder storage 770a, defining coring locations, and returning them to the storage 770a. A computer system 760 is used to store the X-Y coordinates of the desired coring locations. In the next step, an operator initiates automatic coring operations, such that the donor blocks 716 are transported between the donor-block holder storage 770a and the coring area, and receiver blocks 717 are transported between the receiver block holder storage 770b and the coring area, until all coring and deposition actions are completed.

3) Fluidics Robots

Many of the inventions herein disclosed for dispensing fluid droplets in the form of microarrays are also directly applicable to the fluid dispensing requirements of fluidics robots. Fluid dispensing applications handled by fluidic robots may include, for example:

a) dispensing fluid from external reservoirs into arrays of smaller receptacles, such as micro-centrifuge tubes or microplates;

b) transferring fluid from one fluid reservoir mounted on the robot's platen to another reservoir, e.g. dispensing the contents of a centrifuge tube into the wells of a microplate;

c) transferring fluid from the wells of one microplate to the same or different wells of another microplate;

d) dividing fluid samples from one microplate into multiple microplates with the same distribution, (such action is commonly known as "replication" of microplates);

e) dividing fluid samples from one microplate into multiple microplates with a different distribution;

f) transferring fluids from microplates with a less dense arrangement of wells to microplates with a denser arrangement of wells (e.g. transfers from four 96-well microplates to one 384-well microplates, or from four 384-well microplates to one 1536-well microplate) (such actions are commonly known as "compression" of microplates);

g) transferring fluids from microplates with a denser arrangement of wells to microplates with a less dense arrangement of wells (e.g. transfers from one 1536-well microplate to four 384-well microplates, or from one 384-well microplate to four 96-well microplates) (such actions are commonly known as "expansion" of microplates);

h) transferring fluids from particular wells of one or more microplates to a new microplate (such actions are commonly known as "re-arraying" or "cherry picking");

i) compressing plates, where, for example, the contents of four 96-well microplates are combined onto one 384-well microplate; and j) preparing assays, wherein several fluids are dispensed into a vessel (such as the well of a microplate) for the purpose of causing a chemical or biological reaction.

Figure 16:
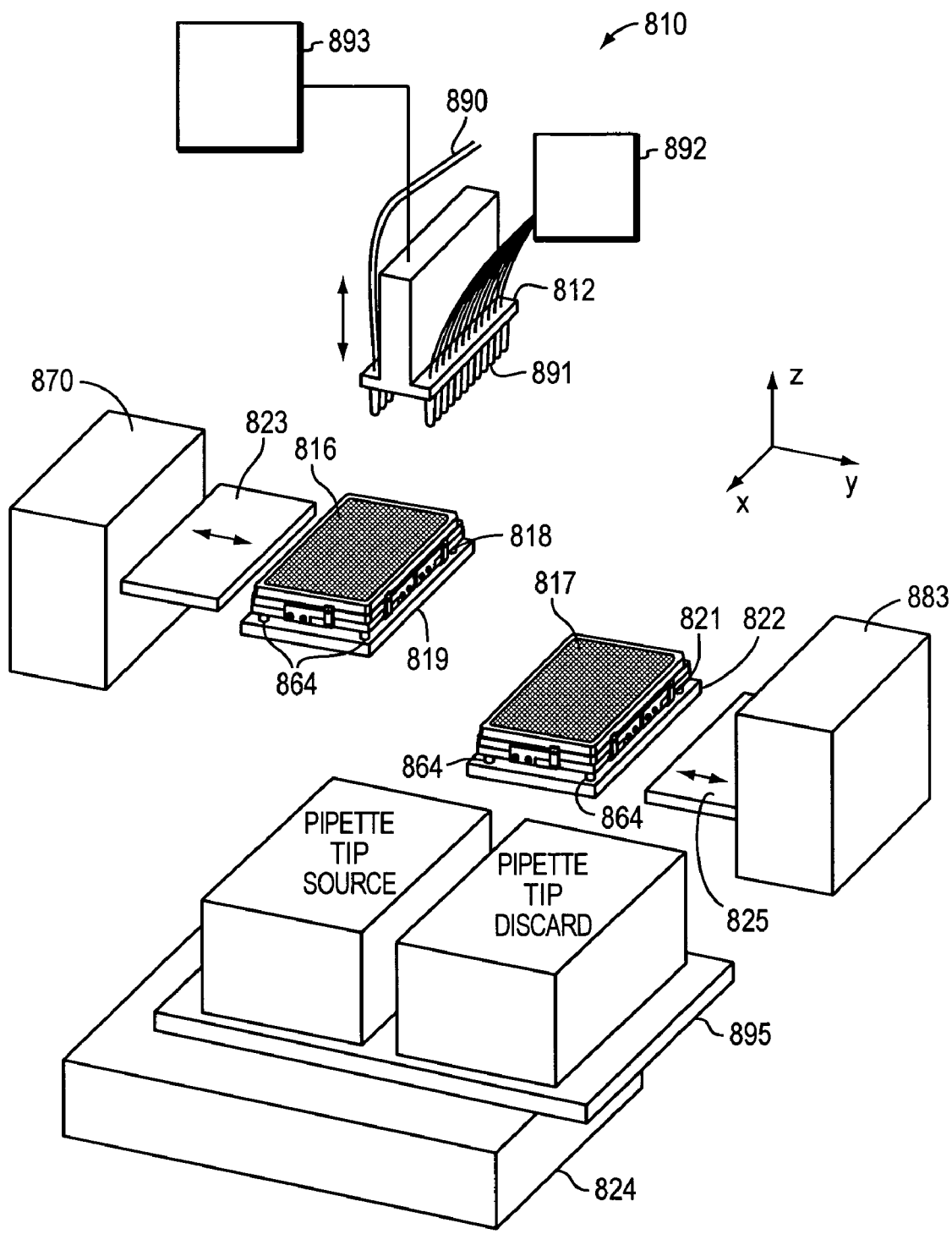
FIG. 16 is a schematic perspective view of a fluidics robot in accordance with one embodiment of the invention.

With reference to FIG. 16, one embodiment of a fluidic robot 810 is illustrated. The robot 810 includes a dispensing head 812 that is mobile in a vertical axis. In one embodiment, the dispensing head 812 includes dispensing tubes 890 connected to external fluid reservoirs (not shown). In another embodiment, the dispensing head 812 includes pipette tips 891 for aspirating and dispensing fluid from local source reservoirs 816, 817. The dispensing tubes and the pipette tips 891 may be moveable relative to each other in at least one of an x-axis or y-axis to accommodate a variety of well separations (i.e. the center-to-center distance between wells) on source and target reservoirs 816, 817. In one embodiment, a vacuum source 892 is provided to aspirate fluids from the fluid reservoirs. Similarly, a pressure source may be provided to eject fluid from the dispensing head 812.

The robot also includes a source-reservoir 816 mounted to a source-reservoir holder 818, the source-reservoir holder 818 including inserts for resting on datums 864 disposed on a source-reservoir holder support 819. The source-reservoir holder 818 may move in any direction within a plane perpendicular to the axis of motion of the dispensing head 812 when disposed beneath the dispensing head 812. A conveyor 823 may be used to extract source-reservoir holders 816 from a source-reservoir holder storage 870 and to return them thereto.

Similarly, the robot 810 also includes a target-reservoir 817 mounted to a target-reservoir holder 821, the target reservoir holder 821 including inserts for resting on datums 864 disposed on a target reservoir holder support 822. The target-reservoir holder 821 may move in any direction within a plane perpendicular to the axis of motion of the dispensing head 821 and displaced from, but parallel to, the plane of motion of the source reservoir holder 819. A conveyor 825 may be used to extract target-reservoir holders 819 from a target-reservoir holder 883 and return them thereto.

The referencing systems previously described for use with the microarrayer substrate holder, the substrate-holder support, the fluid-reservoir holder, and the fluid-reservoir holder support are also applicable to the source-reservoir holder 818, the source-reservoir holder support 819, the target-reservoir holder 821, and the target-reservoir holder support 822 and will therefore not be further described. The referencing system permits installation of the holders 818, 821 onto the mobile reservoir holder supports 819, 822 of the fluidics robot 810 in a predictable, repeatable manner.

In one embodiment, overall holder and holder support system position accuracy is within ±0.02" in the x, y, and z-axes. In a preferred embodiment overall holder and holder support system position accuracy is within ±0.002" in the z-axis and within ±0.01 " in the x and y axes. In a more preferred embodiment, overall holder and holder support system position accuracy is within ±0.0002" in the z-axis and within ±0.001" in the x and y axes.

The use of standardized holders that may be repeatably and accurately loaded into the fluidics robot 810 in a known position within a known plane, reduces the need to manually reconfigure the dispensing assemblies of the robot 810 for different operating conditions. As a corollary, the need for human access to the dispensing area of the machine is minimized, reducing the potential for human error. Moreover, the system facilitates the conversion of the robot 810 from one transfer operation to another. For instance, to change the transfer operation being conducted by the robot 810, a user places the new source reservoir 816 and target reservoir 817 in the storages 870, 883, and updates the computer control system 893 of the fluidic robot 810 to inform the computer 893 of the type of fluid reservoirs 816, 817 being held in the storages 870, 883, their locations, and the type of transfer operation to be conducted.

In another embodiment in accordance with the invention, to avoid cross-contamination between fluid samples, disposable pipette tips 891 are used (which are then discarded after pipetting of that sample is completed). Alternatively, in another embodiment, a wash station 824 is provided to wash the pipette tips 891 before a new fluid sample is aspirated. In many instances, both a washing station 824 and disposable pipette tips 891 are provided. With continued reference to FIG. 16, a pipette tip replacement assembly is illustrated. The assembly includes a mobile pipette-tip support 895 that holds disposable pipette tips 891 that may be supplied to the dispensing head 812. The pipette-tip support 895 may also hold a bin for discarded pipette tips 891. The mobile pipette-tip holder 895 can move in any direction within a plane parallel to those of the source reservoir holder 818 and the target reservoir holder 821, but is vertically displaced from both. In a further embodiment, a pipette-tip-tray storage is included, from which a plurality of pipette-tip trays 895 may be retrieved that containing a wide range of tip sizes and types.

In another embodiment, a plurality of dispensing heads are included in the fluidics robot. Each dispensing head is independently mobile and is restricted to travel in a vertical axis, the axes being spaced apart. The apparatus may be used, for example, in situations where a wide range of pipette tip sizes are required for transfer operations. In this situation, each dispensing head may accommodate dispensers that accept a different range of pipette-tip sizes. In another example, each of the dispensing heads may accommodate a different range of well-to-well spacings. As another example, one head of the assembly may be designed for colony picking, such that colonies of cells grown on a growth media in a container can be extracted and dispensed into other reservoirs, such as the well of a microplate.

In other embodiments, devices that further process the assays that have been prepared may be added to the system 810. For example, the source reservoir 816 or the target reservoir 817 may be transferred to one or more various devices, including, but not limited to:

a) a device for supporting polymerase chain reactions via timed heating and cooling actions,
    b) a device for maintaining timed exposure to a specific temperature and/or humidity (for instance for a hybridization reaction, a re-hydration step or a cooling step to slow a reaction),
    c) a device for timed heating and cooling at other than ambient air pressure,
    d) a device for centrifugation of the fluid samples,
    e) a device for vacuum filtering of fluids (including vacuum filtering in a well-plate format),
    f) a device for filtering of plasmids by magnetic beads (including magnetic bead filtering in a well-plate format),
    g) a device for shaking and stirring,
    h) a device for producing optical images of the dispensed or deposited material,
    i) a device for detecting the presence of substances based on adsorption, or
    j) a scanner for producing images of concentrations of tags attached to biological entities, such tags being detectable due to radio-active emission, florescent emission following laser illumination, or optical scattering (such as that for minute optical scatterers known as quantum dots).

In one embodiment, fluid dispensing operation can continue in the dispensing area of the assembly while other holders 818, 821 are being processed in the additional devices.

4) Identification and Tracking Adaptations

In other embodiments of the foregoing microarrayer, tissue arrayer and fluid dispensing systems, the use of one or more of the following elements may be included to improve their overall performance or utility. These elements also can be beneficially used in other instruments for the generation, dispensing, processing, sampling, scanning and examination of deposited fluid, semi-solid or solid samples.

For instance, in various embodiments, a means of identification may be provided on one or more of the apparatuses that are loaded into or removed from, any of the assemblies earlier described. As an example, some of the elements that may effectively receive such identification means include:

a) the microarray substrates, such as glass slides,
    b) the microarray substrate-holders,
    c) the microarray fluid reservoirs, such as microplates,
    d) the microarray fluid-reservoir holders,
    e) the tissue arrayer donor blocks,
    f) the tissue arrayer donor-block holders,
    g) the tissue arrayer receiver blocks,
    h) the tissue arrayer receiver-block holders,
    i) the fluidics robot source-reservoirs, such as microplates,
    j) the fluidics robot source-reservoir holders,
    k) the fluidics robot target-reservoirs,
    l) the fluidics robot target-reservoir holders, and
    m) the fluidic robot pipette-tip holders.

The identification allows the element to be recognized and/or its progress tracked and correlated with information recorded elsewhere on the processes that have been applied to that element. For example, tracking a unique identification code on a microarray slide permits that slide to be located within a collection of slides. If the microarrayer control computer records the details of the fluid samples deposited on that slide, and where they are deposited, both the slide and the information on its data contents is easily retrieved. As another example, pipette-tip holders of different types and sizes of may be automatically recognized and appropriately chosen by the fluidic robot. Similarly, the fluidics robot may autonomously recognize the type of fluid reservoirs placed in the various receptacle of the storage hotel and retrieve them accordingly. Several means exist to provide identification of these elements including, but not limited to:

I. placement, on the element, of a bar code that can be optically scanned by non-contact means,
    II. placement, on the element, of a radio-frequency identification (RFID) transponder that is programmed with a unique code, that can be read by a RFID interrogator by non-contact means,
    III. placement, on the element, of a semi-conductor memory device that is programmed with a unique code, that can be read by a electrical sensor by direct electrical contact, and
    IV. placement, on the element, of a semi-conductor memory device that is programmed with a unique code, that can be read over an optical, infra-red or radio-frequency communication to an external sensor.

In other embodiments, a means of storing identification, content and process data is provided on one or more of those elements that are loaded into, or removed from, any of the assemblies described herein. The local storage on an element of both identification and content information may provide various advantages. For example, the contents of a microplate retrieved from a stack of similar plates otherwise identical in appearance can be unambiguously identified. As another example, a microarrayer can sense and internally record the information on the content of each well location from which fluid is sampled; this information can be transferred, by the microarrayer, to the local data recording associated with the substrate onto which the material is deposited (or the substrate-holder). As another example, a fluidics robot preparing an assay in the well of a target reservoir can sense the contents of all contributing source fluid reservoirs and record all information on the local data storage of the target reservoir. In yet another example with the fluidics robot, the polymerase chain reaction (PCR) protocol applied to particular fluid samples in a microplate may be recorded in the local data storage of the reservoir and passed along with the sample in all subsequent processing. Many similar uses for the local data storage exist and are included within the scope of the present invention. Several means exist to provide identification of these elements including, but not limited to:

I. placement, on the element, of a radio-frequency identification (RFID) transponder that is dynamically programmable with information on the element, that can be read by a RFID interrogator by non-contact means, II. placement, on the element, of a semi-conductor memory device that is dynamically programmable with information about the element, that can be read by a electrical sensor by direct electrical contact, and III. placement, on the element, of a semi-conductor memory device that is dynamically programmable with information about the element, that can be read over an optical, infra-red or radio-frequency communication to an external sensor.

Other embodiments incorporating the concepts disclosed herein may be used without departing from the spirit and scope of the invention. The described embodiments are to be considered in all respects as only illustrative and not restrictive.

What is claimed is:

1. A microarrayer assembly for depositing minute droplets of fluid on a substrate comprising:
    a deposit element for depositing minute droplets of fluid onto a surface of a substrate;
    a substrate holder support; and
    a removable substrate-holder for holding at least one substrate, the substrate-holder comprising a means for precisely and repeatably positioning the substrate-holder on the substrate-holder support, wherein the means comprises a datum plane defined by at least three datums:
        a first datum for engaging the substrate-holder and for restricting movement of the substrate-holder along an x-axis and a mutually orthogonal y-axis, and defining a first point in a z-axis, the z-axis mutually orthogonal to the x-axis and the y-axis;
        a second datum for engaging the substrate-holder and for at least partially locating the substrate-holder along at least one of the x-axis and the y-axis and defining a second point in the z-axis; and
        a third datum for engaging the substrate-holder and defining a third point in the z-axis.

2. The microarrayer assembly of claim 1 wherein the first datum comprises at least a portion of a sphere for engaging a conical recess formed in the substrate-holder.

3. The microarrayer assembly of claim 1 wherein the second datum is engageable with a linear recess formed in the substrate-holder.

4. The microarrayer assembly of claim 1, further comprising:
    a removable fluid-reservoir for holding at least one fluid; and
    a fluid reservoir holder support, the removable fluid-reservoir comprising an apparatus for repeatably positioning the removable fluid-reservoir on the fluid-reservoir support.

5. The microarrayer assembly of claim 1 further comprising:
    a removable fluid-reservoir holder for holding a removable fluid-reservoir; and
    a fluid-reservoir holder support, the fluid-reservoir holder comprising an apparatus for precisely and repeatably positioning the removable fluid-reservoir holder on the fluid-reservoir holder support.

6. The microarrayer assembly of claim 4, further comprising:
    a fluid-reservoir holder support motion stage for moving the fluid-reservoir holder support; and
    a substrate holder support motion stage for moving the substrate holder support, wherein the fluid-reservoir holder support motion stage and the substrate holder support motion stage are adapted for movement in at least one dimension, wherein the fluid-reservoir holder support motion stage moves in unison with the substrate-holder support motion stage.

7. The microarrayer assembly of claim 1 wherein the deposit element comprises a solid pin.

8. The microarrayer assembly of claim 4, further comprising a fluid-reservoir storage and an apparatus for moving the removable fluid-reservoir between the fluid-reservoir storage and the fluid-reservoir support.

9. The microarrayer assembly of claim 8, further comprising a sensor to determine presence of a fluid-reservoir in a bay of the fluid-reservoir storage.

10. The microarrayer assembly of claim 1, further comprising a substrate-holder storage and an apparatus for moving the removable substrate-holder between the substrate-holder storage and the substrate-holder support.

11. The microarrayer assembly of claim 10, further comprising a sensor to determine presence of a substrate-holder in a bay of the substrate-holder storage.

12. The microarrayer assembly of claim 1 further comprising:
    a deposit element motion stage for moving the deposit element, wherein the deposit element is constrained to move along a z-axis during a deposition procedure; and
    a substrate-holder support motion stage for moving the substrate-holder support, wherein the substrate-holder support is constrained to move in a plane substantially perpendicular to the z-axis during a deposition procedure.

13. The microarrayer assembly of claim 4 further comprising:
    a deposit element motion stage for moving the deposit element, wherein the deposit element is constrained to move along a z-axis during a deposition procedure; and
    a fluid-reservoir support motion stage for moving the fluid-reservoir support, wherein the fluid-reservoir support is constrained to move in a plane substantially perpendicular to the z-axis during a deposition procedure.

14. The microarrayer assembly of claim 13, further comprising a substrate-holder support motion stage for moving the substrate-holder support, wherein a fluid-reservoir support plane of motion is parallel to and displaced from a substrate-holder support plane of motion during a deposition procedure.

15. The microarrayer assembly of claim 14 wherein the fluid-reservoir support motion stage is moveable independently of but in coordination with the substrate-holder motion stage and the deposit element motion stage.

16. The microarrayer assembly of claim 4 wherein the removable fluid-reservoir is a multi-well plate having 96 wells or a multiple thereof.

17. The microarrayer assembly of claim 1, further comprising a substrate, wherein the substrate comprises a multi-well plate.

18. The microarrayer assembly of claim 1, further comprising:
    a first deposit element, wherein the deposit element comprises the first deposit element;
    a second deposit element;
    a first printhead for holding the first deposit element; and
    a second printhead for holding the second deposit element, each printhead for holding at least one deposit element.

19. The microarrayer assembly of claim 1, wherein the removable substrate-holder comprises:
    a top surface and a bottom surface spaced from the top surface;

an aperture extending at least partially between the top surface and the bottom surface, an intersection of the aperture and the top surface defining a perimeter; and at least three reference surfaces proximate the perimeter and extending from the perimeter and defining a reference plane, the reference surfaces adapted to engage a top surface of the substrate when the substrate is disposed in the aperture.

20. The microarrayer assembly of claim 19, further comprising means to bias the substrate against the at least three reference surfaces.

21. The microarrayer assembly of claim 1, further comprising a sensor to measure a distance from the deposit element to a top surface of the substrate.

22. The microarrayer assembly of claim 21, further comprising a motion control system to dynamically adjust a motion of the deposit element in response to the sensor measurement to deposit the minute droplet of fluid onto the substrate without the deposit element contacting the substrate.

23. The microarrayer assembly of claim 5, further comprising:
a fluid reservoir;
a barcode reader; and
a barcode reader-readable label secured to at least one of the fluid-reservoir holder and the fluid-reservoir.

24. The microarrayer assembly of claim 10 wherein the apparatus is adapted to:
move the substrate-holder in a vertical direction within the substrate-holder storage to dispose the removable substrate-holder on the substrate holder support; and
move the substrate-holder support in a horizontal direction to retract the substrate-holder support from the substrate-holder storage.

25. The microarrayer assembly of claim 10 wherein the removable substrate-holder is adapted for at least one of being removed from and added to the substrate-holder storage during active fluid capture and droplet deposition operations.

26. The microarrayer assembly of claim 4, wherein the fluid-reservoir comprises a tracking device, the tracking device comprising at least one of:
a barcode;
a radio-frequency identification (RFID) transponder programmed with a unique code readable by an RFID interrogator by non-contact means; and
a semi-conductor memory device programmed with a unique code that is readable by at least one of an electric sensor and an external sensor that is in communication with the semi-conductor memory device through at least one of optical, infra-red, and radio-frequency communication.

27. The microarrayer assembly of claim 5 comprising a means for locally storing and updating information on at least one of the fluid reservoir and the fluid-reservoir holder, the means comprising at least one of:
a dynamically programmable radio-frequency identification (RFID) transponder mounted on at least one of the substrate, the substrate-holder, the fluid reservoir, and the fluid-reservoir holder, the transponder readable by an RFID interrogator by non-contact means; and
a dynamically programmable semi-conductor memory device mounted on at least one of the fluid reservoir and the fluid-reservoir holder, the semi-conductor memory device readable by at least one of electrical contact and an external sensor that is in communication with the semi-conductor memory device through at least one of optical, infra-red, and radio-frequency communication.

28. The microarrayer assembly of claim 1, wherein the means for precisely and repeatably positioning the removable substrate-holder on the substrate-holder support system exhibits a position accuracy within ±0.002" in a z-axis and within ±0.01" in x and y axes.

29. The microarrayer assembly of claim 1, wherein the means for precisely and repeatably positioning the removable substrate-holder on the substrate-holder support system exhibits a position accuracy within ±0.001" in a z-axis and within ±0.005" in x and y axes.

30. The microarrayer assembly of claim 1, wherein the means for precisely and repeatably positioning the removable substrate-holder on the substrate-holder support system exhibits a position accuracy within ±0.002" in a z-axis and within ±0.01" in x and y axes.

31. The microarrayer assembly of claim 1, further comprising:
a substrate positioned on the removable substrate-holder;
a barcode reader; and
a barcode reader-readable label secured to at least one of the removable substrate-holder and the substrate.

32. The microarrayer assembly of claim 1, further comprising:
a substrate positioned on the removable substrate-holder, wherein the substrate comprises a tracking device, the tracking device comprising at least one of:
a barcode;
a radio-frequency identification (RFID) transponder programmed with a unique code readable by an RFID interrogator by non-contact means; and
a semi-conductor memory device programmed with a unique code that is readable by at least one of an electric sensor and an external sensor that is in communication with the semi-conductor memory device through at least one of optical, infra-red, and radio-frequency communication.

33. The microarrayer assembly of claim 1 comprising a means for locally storing and updating information on at least one of the substrate and the substrate-holder, the means comprising at least one of:
a dynamically programmable radio-frequency identification (RFID) transponder mounted on at least one of the substrate and the substrate-holder, the transponder readable by an RFID interrogator by non-contact means; and
a dynamically programmable semi-conductor memory device mounted on at least one of the substrate and the substrate-holder, the semi-conductor memory device readable by at least one of electrical contact and an external sensor that is in communication with the semi-conductor memory device through at least one of optical, infra-red, and radio-frequency communication.

34. The microarrayer assembly of claim 1 wherein the substrate-holder support further comprises means for restraining the substrate-holder against the substrate holder support.

35. The microarrayer assembly of claim 34 wherein the means for restraining is selected from the group consisting of a magnet, an electromagnet, an electrostatic device, a vacuum device, and a mechanical device.

36. The microarrayer assembly of claim 1, further comprising a second deposit element and an apparatus for moving the deposit element and the second deposit element cooperatively.

37. The microarrayer assembly of claim 36, wherein the deposit element comprises a first printhead and the second deposit element comprises a second printhead.

38. The microarrayer assembly of claim 37, wherein the first printhead moves independently from the second printhead.

39. A microarrayer assembly for depositing minute droplets of fluid on a substrate comprising:
- a deposit element for depositing minute droplets of fluid onto a surface of a substrate;
- a substrate holder support comprising a first datum, a second datum, and a third datum; and
- a removable substrate-holder for holding at least one substrate, the substrate-holder comprising an apparatus for precisely and repeatably positioning the substrate-holder on the substrate-holder support, wherein the apparatus for precisely and repeatably positioning the substrate-holder on the substrate-holder support comprises:
  - a first element for mating with the first datum disposed on the substrate-holder support, and for restricting movement of the removable substrate-holder along an x-axis and a mutually orthogonal y-axis and defining a first point in a z-axis, the z-axis mutually orthogonal to the x-axis and the y-axis;
  - a second element for mating with the second datum disposed on the substrate-holder support, and for at least partially locating the removable substrate-holder along at least one of the x-axis and the y-axis while defining a second point in the z-axis; and
  - a third element for mating with the third datum disposed on the substrate-holder support and defining a third point in the z-axis.

40. The microarrayer assembly of claim 39, wherein the first element forms a conical recess for mating with the first datum.

41. The microarrayer assembly of claim 39 wherein at least two of the first element, the second element, and the third element are adjustable along the z-axis.

42. A microarrayer assembly for depositing minute droplets of fluid on a substrate comprising:
- a deposit element for depositing minute droplets of fluid onto a surface of a substrate;
- a removable substrate-holder for holding at least one substrate, the substrate-holder comprising an apparatus for precisely and repeatably positioning the substrate-holder on a substrate-holder support;
- a fluid reservoir holder support comprising a first datum, a second datum, and a third datum; and
- a removable fluid-reservoir holder for holding a removable fluid-reservoir, the fluid-reservoir holder comprising an apparatus for precisely and repeatably positioning the removable fluid-reservoir holder on the fluid-reservoir holder support, wherein the apparatus for repeatably positioning the removable fluid-reservoir holder on the fluid-reservoir holder support comprises:
  - a first element for mating with the first datum disposed on the fluid-reservoir holder support, and for restricting movement of the removable fluid-reservoir holder along an x-axis and a mutually orthogonal y-axis and defining a first point in a z-axis, the z-axis mutually orthogonal to the x-axis and the y-axis;
  - a second element for mating with the second datum disposed on the fluid-reservoir holder support, and for at least partially locating the removable fluid-reservoir holder along at least one of the x-axis and the y-axis while defining a second point in the z-axis; and
  - a third element for mating with the third datum disposed on the fluid-reservoir holder support and defining a third point in the z-axis.

43. The microarrayer assembly of claim 42 wherein the first element forms a conical recess for mating with the first datum.

44. The microarrayer assembly of claim 42 wherein at least two of the first element, the second element, and the third element are adjustable along the z-axis.

45. A microarrayer assembly for depositing droplets of fluid on a substrate comprising:
- a deposit element for depositing minute droplets of fluid onto a surface of a substrate;
- a removable substrate-holder for holding at least one substrate, the substrate-holder comprising an apparatus for precisely and repeatably positioning the substrate-holder on a substrate-holder support;
- a fluid reservoir support; and
- a removable fluid-reservoir for holding at least one fluid, the removable fluid-reservoir comprising an apparatus for repeatably positioning the removable fluid-reservoir on the fluid-reservoir support, wherein the fluid-reservoir support comprises:
  - a first datum for engaging the removable fluid-reservoir and for restricting movement of the removable fluid-reservoir along an x-axis and a mutually orthogonal y-axis, and defining a first point in a z-axis, the z-axis mutually orthogonal to the x-axis and the y-axis;
  - a second datum for engaging the removable fluid-reservoir and for at least partially locating the removable fluid-reservoir along at least one of the x-axis and the y-axis and defining a second point in the z-axis; and
  - a third datum for engaging the removable fluid-reservoir and defining a third point in the z-axis.

46. The microarrayer assembly of claim 45 wherein the first datum comprises at least a portion of a sphere for engaging a conical recess disposed on the removable fluid-reservoir.

47. The microarrayer assembly of claim 45 wherein the second datum is engageable with a linear recess disposed on the removable fluid-reservoir.

48. A microarrayer assembly for depositing minute droplets of fluid on a substrate comprising:
- a deposit element for depositing minute droplets of fluid onto a surface of a substrate;
- a substrate holder support; and
- a removable substrate-holder for holding at least one substrate, the substrate-holder comprising an apparatus for precisely and repeatably positioning the substrate-holder on the substrate-holder support, wherein the removable substrate-holder further comprises a removable substrate-mounting fixture, the substrate-mounting fixture including a locking element for securing the substrate-mounting fixture into the removable substrate-holder, the substrate-mounting fixture for holding at least one substrate.

49. A microarrayer assembly for depositing minute droplets of fluid on a substrate comprising:
- a plurality of deposition engines operating cooperatively, each deposition engine comprising a deposit element for depositing minute droplets of fluid onto a surface of a substrate;
- a substrate-holder; and
- a support for holding the substrate-holder, the support comprising a means for precisely and repeatably positioning the substrate-holder on the support, wherein the means for precisely and repeatably positioning the substrate holder on the support comprises:
  - a first datum for engaging the substrate-holder and for restricting movement of the substrate-holder along an x-axis and a mutually orthogonal y-axis, and defining a first point in a z-axis, the z-axis mutually orthogonal to the x-axis and the y-axis;

a second datum for engaging the substrate-holder and for at least partially locating the substrate-holder along at least one of the x-axis and the y-axis and defining a second point in the z-axis; and a third datum for engaging the substrate-holder and defining a third point in the z-axis.

50. The microarrayer assembly of claim 49, further comprising a substrate positioned on the substrate-holder and a substrate conveyor for moving the substrate-holder from a first deposition engine to a second deposition engine.

51. The microarrayer assembly of claim 49, further comprising a fluid reservoir positioned on the fluid reservoir-holder and a fluid reservoir conveyor for moving the fluid reservoir-holder from a first deposition engine to a second deposition engine.

52. A method for depositing minute droplets of fluid on a substrate comprising:
    providing a deposit element;
    providing a substrate;
    providing a substrate-holder;
    providing a substrate holder support;
    loading the substrate on the substrate holder;
    loading the substrate-holder onto the substrate-holder support, the substrate-holder comprising a means for precisely and repeatably positioning the substrate-holder on the substrate-holder support, wherein the means for precisely and repeatably positioning the substrate holder on the support comprises:
        a first datum for engaging the substrate-holder and for restricting movement of the substrate-holder along an x-axis and a mutually orthogonal y-axis, and defining a first point in a z-axis, the z-axis mutually orthogonal to the x-axis and the y-axis;
        a second datum for engaging the substrate-holder and for at least partially locating the substrate-holder along at least one of the x-axis and the y-axis and defining a second point in the z-axis; and
        a third datum for engaging the substrate-holder and defining a third point in the z-axis;
    providing fluid to the deposit element, the deposit element moveable relative to the substrate-holder; and
    transferring a droplet of fluid from the deposit element to the substrate.

53. A microarrayer assembly for depositing minute droplets of fluid on a substrate comprising:
    a deposit element for depositing minute droplets of fluid onto a surface of a substrate;
    a substrate-holder support; and
    a removable substrate-holder for holding at least one substrate, the substrate-holder comprising a means for precisely and repeatably positioning the substrate-holder on the substrate-holder support, wherein the substrate-holder support comprises a datum plane defined by at least three datums:
        a first datum for engaging the substrate-holder and for restricting movement of the substrate-holder along an x-axis and a mutually orthogonal y-axis, and defining a first point in a z-axis, the z-axis mutually orthogonal to the x-axis and the y-axis;
        a second datum for engaging the substrate-holder and for at least partially locating the substrate-holder along at least one of the x-axis and the y-axis and defining a second point in the z-axis; and
        a third datum for engaging the substrate-holder and defining a third point in the z-axis.

54. A microarrayer assembly for depositing minute droplets of fluid on a substrate comprising:
    a plurality of deposition engines operating cooperatively, each deposition engine comprising a deposit element for depositing minute droplets of fluid onto a surface of a substrate;
    a removable substrate-holder for holding at least one substrate; and
    a substrate conveyor for moving the removable substrate-holder from a first deposition engine to a second deposition engine, the substrate-holder comprising a means for precisely and repeatably positioning the substrate-holder on the substrate conveyor, wherein the means for precisely and repeatably positioning the substrate holder on the substrate conveyor comprises:
        a first datum for engaging the substrate-holder and for restricting movement of the substrate-holder along an x-axis and a mutually orthogonal y-axis, and defining a first point in a z-axis, the z-axis mutually orthogonal to the x-axis and the y-axis;
        a second datum for engaging the substrate-holder and for at least partially locating the substrate-holder along at least one of the x-axis and the v-axis and defining a second point in the z-axis; and
        a third datum for engaging the substrate-holder and defining a third point in the z-axis.

55. The microarrayer assembly of claim 54 further comprising a fluid reservoir-holder and a fluid reservoir conveyor for moving the fluid reservoir-holder from a first deposition engine to a second deposition engine.

56. The microarrayer assembly of claim 54, wherein at least one of the deposition engines further comprises an inkjet deposition device.

57. The microarrayer assembly of claim 54, wherein at least one of the deposition engines further comprises a solid pin deposition device.

58. The microarrayer assembly of claim 54, wherein at least one of the deposition engines further comprises a quill pin deposition device.

59. A microarrayer assembly for depositing minute droplets of fluid on a substrate comprising:
    a deposit element for depositing minute droplets of fluid onto a surface of a substrate;
    a fluid-reservoir holder support; and
    a fluid-reservoir holder comprising a means for precisely and repeatably positioning the fluid-reservoir holder on the fluid-reservoir holder support, wherein the means for precisely and repeatedly positioning the fluid-reservoir holder on the fluid-reservoir holder support comprises:
        a first raised edge disposed on the fluid-reservoir holder support;
        a first spring clip disposed on the fluid-reservoir holder support for biasing the fluid-reservoir holder against the first raised edge and for restricting the movement of the fluid-reservoir holder along an x-axis;
        a second raised edge disposed on the fluid-reservoir holder support and perpendicular to the first raised edge; and
        a second spring clip disposed on the fluid-reservoir holder support for biasing the fluid-reservoir holder against the second raised edge and for restricting the movement of the fluid-reservoir holder along a y-axis orthogonal to the x-axis.

60. The microarrayer assembly of claim 59, wherein the means for precisely and repeatably positioning the fluid-reservoir holder on the fluid-reservoir holder support comprises:
    a datum for engaging the fluid-reservoir holder and for restricting movement of the fluid reservoir holder relative to the fluid-reservoir holder support.

61. The microarrayer assembly of claim 60, wherein the means for precisely and repeatably positioning further comprises a magnet to bias the fluid-reservoir holder relative to the fluid-reservoir holder support.

62. A microarrayer assembly for depositing minute droplets of fluid on a substrate comprising:
    a deposit element for depositing minute droplets of fluid onto a surface of a substrate;
    a substrate holder support; and
    a removable substrate-holder for holding at least one substrate, the substrate-holder comprising a means for precisely and repeatably positioning the substrate-holder on the substrate-holder support, wherein the means for precisely and repeatedly positioning the substrate-holder on the substrate-holder support comprises:
        a first element for mating with a first datum disposed on the substrate-holder support, and for restricting movement of the removable substrate-holder along a first axis while defining a first point on the z-axis, wherein the first axis defines at least one of an x-axis and a y-axis;
        a second element for mating with a second datum disposed on the substrate-holder support, and for restricting movement of the removable substrate-holder along the first axis while defining a second point on the z-axis; and
        a third element for mating with a third datum disposed on the substrate-holder support, and for restricting movement of the removable substrate-holder along the second axis while defining a third point on the z-axis, wherein the second axis is orthogonal to the first axis.

63. The microarrayer assembly of claim 62, wherein the means for precisely and repeatedly positioning the substrate-holder on the substrate-holder support further comprises a fourth element for mating with a fourth datum disposed on the substrate-holder support, and for restricting movement of the removable substrate-holder along the second axis while defining a fourth point on the z-axis.

64. The microarrayer assembly of claim 62, wherein each of the first element, the second element, the third element, and the fourth element comprises a linear groove disposed on the substrate-holder.

65. A microarrayer assembly for depositing minute droplets of fluid on a substrate comprising:
    a deposit element for depositing minute droplets of fluid onto a surface of a substrate;
    a substrate holder support; and
    a removable substrate-holder for holding at least one substrate, the substrate-holder comprising a means for precisely and repeatably positioning the substrate-holder on the substrate-holder support, wherein the means for precisely and repeatedly positioning the substrate-holder on the substrate-holder support comprises:
        a first groove disposed on the substrate-holder, the first groove comprising an axis;
        a first datum disposed on the substrate-holder support, wherein the first datum is adapted for mating with the first groove and for restricting movement of the substrate-holder along an x-axis;
        a surface disposed on the substrate-holder support, wherein the surface is orthogonal to the axis of the first groove and the surface restricts movement of the substrate-holder along a y-axis orthogonal to the x-axis; and
        a biasing means to urge the substrate-holder against the surface.

66. The microarrayer assembly of claim 65, wherein the biasing means comprises a spring.

67. A microarrayer assembly for depositing minute droplets of fluid on a substrate comprising:
    a deposit element for depositing minute droplets of fluid onto a surface of a substrate;
    a substrate holder support; and
    a removable substrate-holder for holding at least one substrate, the substrate-holder comprising a means for precisely and repeatably positioning the substrate-holder on the substrate-holder support, wherein the means for precisely and repeatedly positioning the substrate-holder on the substrate-holder support comprises:
        a flat bottom surface disposed on the substrate-holder;
        a flat upper surface disposed on the substrate-holder support for engaging the planar bottom surface of the substrate-holder and for defining a position on a z-axis;
        a first surface disposed on the substrate-holder support and orthogonal to the planar upper surface, wherein the first surface restricts movement of the substrate-holder along an x-axis orthogonal to the z-axis; and
        a second surface disposed on the substrate-holder and orthogonal to both the planar upper surface and the first surface, wherein the second surface restricts movement of the substrate-holder along a y-axis mutually orthogonal to the x-axis and the z-axis.

68. The microarrayer assembly of claim 67, wherein the means for precisely and repeatedly positioning the substrate-holder on the substrate-holder support further comprises a biasing means to urge the substrate-holder against the first surface and the second surface.

* * * * *

UNITED STATES PATENT AND TRADEMARK OFFICE
CERTIFICATE OF CORRECTION

PATENT NO. : 7,585,463 B2 Page 1 of 1
APPLICATION NO. : 10/972792
DATED : September 8, 2009
INVENTOR(S) : Austin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1009 days.

Signed and Sealed this

Fourteenth Day of September, 2010

David J. Kappos
*Director of the United States Patent and Trademark Office*